US012174184B2

(12) United States Patent
Dahl et al.

(10) Patent No.: US 12,174,184 B2
(45) Date of Patent: Dec. 24, 2024

(54) TARGET INTERFERENCE SUPPRESSED ANTI-DRUG ANTIBODY ASSAY

(71) Applicant: Hoffmann-La Roche Inc., Little Falls, NJ (US)

(72) Inventors: Uwe Dahl, Mannheim (DE); Gregor Jordan, Gröbenzell (DE); Roland Staack, Munich (DE); Miriam Moheysen-Zadeh, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 1152 days.

(21) Appl. No.: 16/763,435

(22) PCT Filed: Nov. 27, 2018

(86) PCT No.: PCT/EP2018/082664
§ 371 (c)(1),
(2) Date: May 12, 2020

(87) PCT Pub. No.: WO2019/105916
PCT Pub. Date: Jun. 6, 2019

(65) Prior Publication Data
US 2020/0300852 A1    Sep. 24, 2020

(30) Foreign Application Priority Data

Nov. 29, 2017   (EP) .................... 17204316

(51) Int. Cl.
*G01N 33/543* (2006.01)
*G01N 33/53* (2006.01)

(52) U.S. Cl.
CPC ....... *G01N 33/54393* (2013.01); *G01N 33/53* (2013.01); *G01N 2400/10* (2013.01)

(58) Field of Classification Search
CPC .................... G01N 33/53; G01N 2400/10
See application file for complete search history.

(56) References Cited

U.S. PATENT DOCUMENTS

| | | | |
|---|---|---|---|
| 4,160,019 | A | 7/1979 | Bjorklund |
| 4,699,783 | A | 10/1987 | Terman et al. |
| 10,036,745 | B2 | 7/2018 | Inganäs et al. |
| 2008/0214795 | A1 | 9/2008 | Ramanan et al. |
| 2010/0041063 | A1 | 2/2010 | Essig et al. |
| 2015/0226758 | A1 | 8/2015 | Grabert et al. |

FOREIGN PATENT DOCUMENTS

| | | | |
|---|---|---|---|
| AU | 2011244240 A1 | 12/2012 | |
| CN | 102633876 A | 8/2012 | |
| CN | 103674657 A | 3/2014 | |
| JP | 2015200055 A | 11/2015 | |
| RU | 2110276 C1 | 5/1998 | |
| WO | 2004043233 A2 | 5/2004 | |
| WO | WO-2008031532 A1 * | 3/2008 | .......... C07K 16/065 |
| WO | 2009022001 A1 | 2/2009 | |
| WO | 2015000865 A1 | 1/2015 | |
| WO | 2015123315 A1 | 8/2015 | |

OTHER PUBLICATIONS

Mleczko ("Limitation of tuning the antibody-antigen reaction by changing the value of pH and its consequence of hyperthermia" J. Biochem. 2016 159:421-427 (Year: 2016).*
The English translation of the Notice of Allowance, mailed on Jun. 8, 2023, in the related Korean Appl. No. 10-2020-7018546.
The English translation of the Chinese Office Action, mailed on Feb. 27, 2023, in the related Chinese Appl. No. 201880077471.9.
The Chinese Office Action, mailed on Sep. 21, 2023, in the related Chinese Appl. No. 201880077471.9.
Seiji Kageyama et al., "An improved method for detecting antigens in the blood of HIV carriers," Progress in Microbiology and Immunology, 1989, vol. 4, pp. 62-65. (The English abstract included.).
Zhang et al., "A ferritin time-resolved immunoassay based on nanometer nuropium core-ferritin," Current Immunology, 2017, vol. 37, Issue (1), pp. 20-24. (The English abstract included.).
The English translation of the Japanese Office Action, mailed on Oct. 3, 2023, in related Japanese Appl. No. 2022-165211.
The International Search Report and Written Opinion, mailed on Jan. 14, 2019, in the corresponding PCT Appl. No. PCT/EP2018/082664.
Moxness M et al: "Immunogenicity Testing by Electrochemiluminescent Detection for Antibodies Directed against Therapeutic Human Monoclonal Antibodies", Clinical Chemistry, vol. 51, No. 10, Sep. 1, 2005 (Sep. 1, 2005), pp. 1983-1985, XP003019464.
Patton A et al: "An acid dissociation bridging ELISA for detection of antibodies directed against therapeutic proteins in the presence of antigen", Journal of Immunological Methods, vol. 304, No. 1-2, Sep. 1, 2005 (Sep. 1, 2005), pp. 189-195, XP027659212.
Zoghbi Jad et al: "A breakthrough novel method to resolve the drug and target interference problem in immunogenicity assays", Journal of Immunological Methods, vol. 426, Nov. 2015 (Nov. 2015), pp. 62-69, XP002785311.

(Continued)

*Primary Examiner* — Changhwa J Cheu

(57) ABSTRACT

Herein is reported an immunoassay for quantifying the amount of anti-drug antibody, which anti-drug antibody can specifically bind to a drug antibody, which drug antibody can specifically bind to a therapeutic target, in a serum or plasma sample comprising the steps of a) incubating the serum or plasma sample at a pH value that is about the pI value of the target, and optionally removing formed precipitate after the incubation, b) incubating the serum or plasma sample obtained in step a) at a pH value of about 2, and optionally centrifuging the incubated sample to remove formed precipitate, c) adjusting the pH value to about 7.4, adding capture antibody conjugated to a first member of a binding pair and tracer antibody conjugated to a detectable label to the serum or plasma sample obtained in step b) and incubating the mixture to form a capture antibody-anti-drug antibody-tracer antibody-complex, d) quantifying the complex formed in step c) and thereby quantifying the amount of anti-drug antibody in the serum or plasma sample.

33 Claims, 18 Drawing Sheets

Specification includes a Sequence Listing.

(56) References Cited

OTHER PUBLICATIONS

Llinares-Tello F et al.,: "THU0166 Usefullness of the acid dissociation in immunogenicity detection in patients in treatment with anti-TNF drugs", BMJ, vol. 73, No. suppl, 2, 11, pp. 237-238, Jun. 2014 (Jun. 11, 2014), XP002785312.

Uwe Wessels et al: "Detection of antidrug antibodies against human therapeutic antibodies lacking Fc-effector functions by usage of soluble Fc[gamma] receptor I", Bioanalysis, vol. 8, No. 20, Oct. 1, 2016 (Oct. 1, 2016), pp. 2135-2145, XP055538060.

Lee et al., "Bioanalytical Approaches to Quantify • Total" and "Free" Therapeutic Antibodies and Their Targets: Technical Challenges and PK/PD Applications Over the Course of Drug Development, AAPS J, Mar. 2011; 13(1), pp. 99-110.

Salimi-Moosavi et al., "Novel approaches using alkaline or acid/guanidine treatment to eliminate therapeutic antibody interference in the measurement of total target ligand," Journal of Pharmaceutical and Biomedical Analysis, vol. 51, Issue 5, Apr. 6, 2010, pp. 1128-1133.

Smith et al., "Detection of antibodies against therapeutic proteins in the presence of residual therapeutic protein using a solid-phase extraction with acid dissociation (SPEAD) sample treatment prior to ELISA," Regul Toxicol Pharmacol, Dec. 2007;49(3):pp. 230-237.

Bourdage et al., "An Affinity Capture Elution (ACE) assay for detection of anti-drug antibody to monoclonal antibody therapeutics in the presence of high levels of drug," J Immunol Methods, Oct. 31, 2007;327(1-2):10-7.

Moxness et al., "Development and Validation of Radioligand Binding Assays to Measure Total IgA, IgE, IgG, IgM Insulin Antibodies in Human Serum," Ann N Y Acad Sci, Nov. 2003;1005: pp. 265-268.

Kelley et al., "Theoretical Considerations and Practical Approaches to Address the Effect of Anti-drug Antibody (ADA) on Quantification of Biotherapeutics in Circulation," AAPS J, Jul. 2013;15(3): pp. 646-658.

Davis et al., "A novel method for quantitative measurement of a biomarker in the presence of a therapeutic monoclonal antibody directed against the biomarker," J Pharm Biomed Anal, Nov. 4, 2008;48(3): pp. 897-901.

Collet-Brose et al., "Evaluation of Multiple Immunoassay Technology Platforms to Select the Anti-Drug Antibody Assay Exhibiting the Most Appropriate Drug and Target Tolerance, " J Immunol Res. 2016; Article ID: 5069678, pp. 1-15.

The English translation of the Japanese Office Action, mailed on Oct. 15, 2021, in the related Japanese Appl. No. 2020-529507.

Kubiak et al., "Storage Conditions of Conjugated Reagents Can Impact Results of Immunogenicity Assays," J Immunol Res., vol. 2016; pp. 1-10, Jul. 10, 2016.

* cited by examiner

TARGET INTERFERENCE SUPPRESSED ANTI-DRUG ANTIBODY ASSAY

CROSS-REFERENCE TO RELATED APPLICATIONS

This application is a National Stage Application of PCT/EP2018/082664 filed Nov. 27, 2018, which claims priority from European Patent Application No. 17204316.8, filed on Nov. 29, 2017. The priority of said PCT and European Patent Application are claimed. Each of prior mentioned applications is hereby incorporated by reference herein in its entirety.

The current invention is in the field of anti-drug antibody assays. Herein is reported an anti-drug antibody assay with reduced interference from the target of the therapeutic drug.

BACKGROUND OF THE INVENTION

Moxness, M., et al. (Ann. N. Y. Acad. Sci. USA 1005 (2003) 265-268) reported a radioligand binding assays for total and Ig classes of insulin antibodies (IAB). Test and control sera first were acidified to dissociate bound insulin, and charcoal was added to adsorb the serum insulin. After neutralization, the charcoal with bound insulin was removed from the serum by centrifugation. For each assay, insulin-extracted serum samples were incubated with radiolabeled insulin in the presence and absence of high levels of unlabeled insulin to determine nonspecific binding and total binding, respectively. Thus, Moxness et al. reported a comparison of two ADA assay protocols wherein overnight incubation and acid dissociation were compared.

Patton, A., et al. (J. Immunol. Meth. 304 (2005) 189-195) reported a bridging ELISA that uses a covalently coupled high density antigen surface combined with an acid dissociation step to allow for antibody detection in the presence of antigen in human serum, i.e. without prior removal of excess antigen. Thus, Patton et al. reported an assay protocol in which the excess antigen is not removed prior analysis of the therapeutic antibody. The authors compare the acid pretreated samples with non-pretreated samples, but otherwise identical assay procedure.

Lee, J. W., et al. (AAPS J. 13 (2011) 99-110) report that the predominant driver of bioanalysis in supporting drug development is the intended use of the data. Reliable methodologies for measurements of mAb and its antigen ligand (L) in circulation are crucial for the assessment of exposure-response relationships in support of efficacy and safety evaluations, and dose selection. Ligand-binding assays (LBA) are widely used for the analysis of protein biotherapeutics and antigen ligands (L) to support pharmacokinetics/pharmacodynamics (PK/PD) and safety assessments. For monoclonal antibody drugs (mAb), in particular, which non-covalently bind to L, multiple forms of mAb and L can exist in vivo, including free mAb, free L, and mono- and/or bivalent complexes of mAb and L. Given the complexity of the dynamic binding equilibrium occurring in the body after dosing and multiple sources of perturbation of the equilibrium during bioanalysis, it is clear that ex vivo quantification of the forms of interest (free, bound, or total mAb and L) may differ from the actual ones in vivo. LBA reagents and assay formats can be designed in principle to measure the total or free forms of mAb and L. However, confirmation of the forms being measured under the specified conditions can be technically challenging.

Kelly, M., et al. (AAPS J., 15 (2013) 646-658) report that one area that has been getting increasing attention recently is in the assessment of "free" and "total" analyte and the impact of the assay format on those assessments. The authors provide a critical review of available literature and prospectively explore methods to mitigate the potential impact of anti-drug antibody on PK assay measurement. Furthermore, the methods for increasing drug tolerance in ADA (anti-drug antibody) assays could be re-purposed for assessing or increasing ADA tolerance in PK assays, usually with a preparatory step to break up the immune complex and extract the drug. It must be noted that implementation of such challenging manipulations would not be considered routine for late-stage clinical bioanalysis, but would provide valuable information early on in the investigative stage of method development to pharmacokinetics for their interpretation. Ultimately, any extraction process used to help quantitate drug would likely result in a "total" assessment.

Davis, R. A., et al. (J. Pharm. Biomed. Anal. 48 (2008) 897-901) reported a method for quantifying total (free plus bound) biomarker concentration in the presence of high levels of therapeutic MoAb using a single non-competing MoAb in a capture/acid elution format. This assay has the capability to accurately detect and quantitate circulating ng/ml biomarker levels in the presence of 200µ/ml or more of therapeutic MoAb.

Salimi-Moosavi, H., et al. (J. Pharm. Biomed. Anal. 51 (2010) 1128-1133) reported alkaline and acid/guanidine treatment approaches to dissociate the protein binding and preferentially denature the ThA. The neutralized antigen proteins can be determined by ELISA. These methods provide reproducible measurements of total antigen protein without ThA interference. Serum samples, standards and QCs containing antigen protein and ThA were treated with alkaline buffer (pH>13) containing casein or acid/guanidine buffer (pH<1). Total antigen proteins for two different ThA systems were successfully measured and interferences were completely eliminated by the treatments. These methods were successfully applied to analysis in pre-clinical serum samples.

Smith, H. W., et al. (Regul. Toxicol. Pharmacol. 49 (2007) 230-237) disclosed the detection of antibodies against therapeutic proteins in the presence of residual therapeutic protein using a solid-phase extraction with acid dissociation (SPEAD) sample treatment prior to ELISA.

An affinity capture elution (ACE) assay for detection of anti-drug antibody to monoclonal antibody therapeutics in the presence of high levels of drug was disclosed by Bourdage, J. S., et al. (J. Immunol. Meth. 327 (2007) 10-17).

Zoghbi, J., et al. (J. Immunol. Meth. 426 (2015) 62-69 disclosed a breakthrough novel method to resolve the drug and target interference problem in immunogenicity assays comprising four components for detection of total ADA (free ADA and drug bound ADA) in the presence of drug in patient samples: (1) use excess drug to saturate free ADA to form drug bound ADA as drug:ADA complexes, (2) precipitate the complex using an agent such as PEG, (3) acid dissociate ADA from drug and immobilize (capture) free ADA (and free drug) under acidic conditions (without neutralization) onto a large capacity surface, and (4) detect free ADA (not the captured drug) using specific anti-human Ig detection reagent.

An affinity capture elution (ACE) assay for detection of anti-drug antibody to monoclonal antibody therapeutics in the presence of high levels of drug was disclosed by Bourdage, J. S., et al. (J. Immunol. Meth. 327 (2007) 10-17).

The current anti-drug antibody (ADA) assay gold standard is the bridging assay with the drug on both sides of a formed complex which is detected. This seems to be the appropriate assay format to detect ADA isotypes and ADA specificity.

Collet-Brose, J., et al., (J. Immunol. Res., Article ID 5069678 (2016)) disclosed the evaluation of multiple immunoassay technology platforms to select the anti-drug antibody assay exhibiting the most appropriate drug and target tolerance. The aim of this study was, at the assay development stage and thus with an appropriate degree of rigor, to select the most appropriate technology platform and sample pretreatment procedure for a clinical ADA assay.

WO 2008/031532 disclosed an antibody binding specifically to Cynomolgus IgG characterized by not binding to Human IgG, and a method for the immunological determination of an immune complex (DA/ADA complex) of a drug antibody (DA) and an antibody against said drug antibody (anti-drug antibody, ADA) in a sample of a monkey species using a double antigen bridging immunoassay. Herein a specific anti-cynomolgus monkey IgG that does not cross bind to human IgG is used, whereby this assay can't be used to analyze human samples. Additionally, the presence of soluble therapeutic target will not result in a false positive signal in the assay as reported in WO 2008/031532.

WO 2015/123315 disclosed assays for detecting the presence or amount of an anti-drug antibody comprising a precipitation step resulting in a precipitation of immune-complexes (drug with ADA) followed by an acidification of the precipitate resulting in a release of ADA from the complexes and an acidic adsorption of the ADA to a surface for a final setup of measurable complexes.

Llinares-Tello, F., et al. (BMJ 73 (2014) THU0166) disclosed the usefulness of the acid dissociation in immunogenicity detection in patients in treatment with anti-TNF drugs in a standard ADA assay.

SUMMARY OF THE INVENTION

Herein is reported an anti-drug antibody assay wherein the masking of the anti-drug antibody by the (therapeutic) target of the drug is reduced or even eliminated.

Herein is reported an anti-drug antibody assay which is especially useful for samples comprising the drug, its target and anti-drug antibodies, wherein the interference of the (therapeutic) target of the drug is reduced or even eliminated.

The invention is based, at least in part, on the finding that an incubation step performed at the pI of the target or at an acidic pH value prior to the detection of the anti-drug antibody can be used to reduce the interference from the target of the therapeutic antibody (drug) present in a serum or plasma sample in an anti-drug antibody (detection) assay. The assay according to the current invention is especially useful either if the target of the therapeutic drug tends to aggregate and causes thereby non-specific binding, or/and if the target is bivalent/multivalent and thereby normally resulting in a false positive signal in the assay.

The invention is based, at least in part, on the finding that interference of soluble (therapeutic) target of the drug (therapeutic antibody) present in the sample to be analyzed in an immunoassay can be reduced or even eliminated by using two or more acid dissociation steps in the assay procedure.

The invention is based, at least in part, on the finding that the precipitation/aggregation properties of the soluble (therapeutic) target can be used in the presence of ADA and drug to reduce interference of the soluble (therapeutic) target in an immunoassay. The generally used acidification to a low pH values sill result in a high (background) signal resulting in a loss in sensitivity (see e.g. FIG. 18). It has been found that to improve the soluble target deactivation step/reduce target interference it is not necessary to include a precipitation of immune-complexes in the assay procedure. It has been found that an improvement in assay sensitivity/reduction of soluble (therapeutic) target interference in an immunoassay can be achieved by acidification and neutralization without any separation and/or resuspension of the precipitate.

The invention is based, at least in part, on the finding that an acid treatment step can be used to remove, i.e. precipitate, the soluble target (e.g. at/near to its iso-electric point). Using said acid treatment step to remove soluble (therapeutic) target in the sample and to reduce target interference in an immunoassay makes the method according to the current invention generally applicable. Without being bound by this theory it is assumed that the method according to the current invention is more suitable for the analysis of clinical samples with unknown immune response as the soluble (therapeutic) target can be assumed to be present at comparable amounts in different individuals.

The invention is based, at least in part, on the finding that an incubation at the pI of the soluble target is advantageous for improving the performance of an immunoassay, e.g. in reducing target interference or in improving assay sensitivity.

One aspect according to the current invention is an immunoassay for detecting and/or determining and/or quantifying the amount of anti-drug antibody, which anti-drug antibody can specifically bind to a drug antibody, which drug antibody can specifically bind to a therapeutic target, in a serum or plasma sample with reduced target interference comprising the following steps (in the following order):
  a) incubating an immobilized capture antibody with a serum or plasma sample comprising drug, target and anti-drug antibody, to form a capture antibody-anti-drug antibody complex,
  b) washing the complex formed in step a) with a buffer comprising a sugar and a detergent, which has a pH value of about the pI of the target,
  c) incubating for 12 to 24 hours the washed complex of step b) with a tracer antibody conjugated to a (detectable) label to form a capture antibody-anti-drug antibody-tracer antibody complex, (and)
  d) detecting and/or determining and/or quantifying the amount of anti-drug antibody by determining the (detectable) label in the complex formed in step c).

In one embodiment the drug is an antibody (drug antibody).

In one embodiment the tracer antibody and the capture antibody is the drug antibody.

In one embodiment the immunoassay comprises a capture antibody, a tracer antibody and a detection antibody, wherein the capture antibody is the drug conjugated to a first member of a binding pair, the tracer antibody is the drug antibody conjugated to a detectable label and the detection antibody, which is further conjugated to an enzyme, is an antibody specifically binding to the detectable label.

In one embodiment the capture antibody and/or the tracer antibody is independently of each other selected from the group consisting of complete/full length drug antibody, F(ab')2, Fab and scFv of the drug antibody. In one embodiment the capture antibody and the tracer antibody are each a full length drug antibody, or a F(ab')2 of the drug antibody, or a Fab of the drug antibody.

In one embodiment the sugar is a monosaccharide, a disaccharide or a trisaccharide. In one embodiment the sugar is a disaccharide. In one embodiment the sugar is selected from the group of disaccharides consisting of saccharose, lactose, maltose, iso-maltose, and trehalose. In one preferred embodiment the sugar is saccharose.

In one embodiment the sugar has a concentration of about 6.5 wt-%.

In one embodiment the sugar is saccharose at a concentration of about 6.5 wt-%.

In one embodiment the detergent is a non-ionic detergent. In one embodiment the detergent is selected from the group of detergents consisting of polyalkylene glycol ether (trade name Brij), polyoxyethylene sorbitane monoesters (trade name Tween), octylphenol ethoxylate (trade name Trion or Nonident), octyl-beta-glycoside, n-fatty acid-N-methyl-D-glucamide (trade name MEGA), and N,N'-bis-(3-D-gluconamidopropyl) cholamide (tradename CHAP). In one preferred embodiment the detergent is polyethylene glycol dodecyl ether.

In one embodiment the sugar is saccharose and the detergent is polyethylene glycol dodecyl ether.

In one embodiment the incubation is for 14 to 20 hours. In one embodiment the incubating is for 15 to 17 hours. In one embodiment the incubating is for about 16 hours.

In one embodiment the sugar is saccharose, the detergent is polyethylene glycol dodecyl ether and the incubating is for 15 to 17 hours.

In one embodiment the first member of a binding pair is selected from the group consisting of hapten, antigen and hormone. In one embodiment the binding pair is an antigen/antibody pair or a hapten/anti-hapten antibody pair.

In one embodiment the binding pair is selected from the group consisting of biotin/(strept)avidin, theophylline/anti-theophylline antibody, 5-bromo-desoxy-uridine/anti-5-bromo-deoxy-uridine antibody, digoxigenin/anti-digoxigenin antibody, and helicar/anti-helical antibody. In one embodiment the binding pair is biotin and (strept)avidin.

In one embodiment the drug is an anti-C5 antibody and the target is human C5.

In one embodiment the sugar is saccharose, the detergent is polyethylene glycol dodecyl ether, the drug is an anti-C5 antibody, and the target is human C5.

In one embodiment the sugar is saccharose, the detergent is polyethylene glycol dodecyl ether, the drug is an anti-C5 antibody, the target is human C5 and the buffer has a pH value of about 5.5 or about 5.0.

In one embodiment the sample is a human sample (human serum or plasma sample).

One aspect as reported herein is an immunoassay for detecting and/or determining and/or quantifying the amount of anti-drug antibody, which anti-drug antibody can specifically bind to a drug antibody, which drug antibody can specifically bind to a therapeutic target, in a serum or plasma sample with reduced target interference comprising the following steps:
  a) incubating the serum or plasma sample at a pH value that is about the pI value of the target, and optionally removing formed precipitate after the incubation,
  b) incubating the serum or plasma sample obtained in step a) at a pH value of about 2, and optionally centrifuging the incubated sample to remove formed precipitate,
  c) adjusting the pH value to about 7.4, adding capture antibody conjugated to a first member of a binding pair and tracer antibody conjugated to a detectable label to the serum or plasma sample obtained in step b), and incubating the mixture to form a capture antibody-anti-drug antibody-tracer antibody-complex, (and)
  d) measuring and/or determining and/or quantifying the complex formed in step c) and thereby detecting and/or determining and/or quantifying the amount of anti-drug antibody in the serum or plasma sample.

In one embodiment the step of measuring and/or determining and/or quantifying the capture antibody-anti-drug antibody-tracer antibody-complex (step d)) comprises the steps of
  d1) incubating the serum or plasma sample obtained in step c) with the second member of the binding pair conjugated to a solid surface to capture the capture antibody-anti-drug antibody-tracer antibody-complex, and optionally washing the surface,
  d2) detecting and/or determining and/or quantifying the amount of anti-drug antibody by determining the detectable label in the complex formed in step d1).

In one embodiment the incubation at about the pI value of the target is at a pH value in the range of 0.5 pH units below the pI of the target to 0.5 pH units above the pI value of the target.

In one embodiment the incubating in step a) is with agitation.

In one embodiment the incubating in step a) is for 1.5 to 2.5 hours. In one preferred embodiment the incubating in step a) is for about 2 hours.

In one embodiment the incubating in step b) is for about 5 min.

In one embodiment the incubating in step d) is for about 60 min.

In one embodiment the tracer antibody and the capture antibody is the drug antibody.

In one embodiment the immunoassay comprises a capture antibody, a tracer antibody and a detection antibody, wherein the capture antibody is the drug conjugated to a first member of a binding pair, the tracer antibody is the drug antibody conjugated to a detectable label and the detection antibody, which is conjugated to an enzyme, is an antibody specifically binding to the detectable label.

In one embodiment the capture antibody and/or the tracer antibody is independently of each other selected from the group consisting of complete/full length drug antibody, F(ab')2, Fab and scFv of the drug antibody. In one embodiment the capture antibody and the tracer antibody are each a full length drug antibody, or a F(ab')2 of the drug antibody, or a Fab of the drug antibody.

In one embodiment the first member of a binding pair is selected from the group consisting of hapten, antigen and hormone. In one embodiment the binding pair is an antigen/antibody pair or a hapten/anti-hapten antibody pair.

In one embodiment the binding pair is selected from the group consisting of biotin/(strept)avidin, theophylline/anti-theophylline antibody, 5-bromo-desoxy-uridine/anti-5-bromo-deoxy-uridine antibody, digoxigenin/anti-digoxigenin antibody, and helicar/anti-helical antibody. In one embodiment the binding pair is biotin and (strept)avidin.

In one embodiment the drug is an anti-C5 antibody and the target is human C5. In one embodiment the pH value in step a) is in the range of pH 4.7 to pH 5.5. In one preferred embodiment the pH value in step a) is about pH 5.0 or about pH 5.5.

In one embodiment the immunoassay for detecting and/or determining and/or quantifying the amount of anti-drug antibody, which anti-drug antibody can specifically bind to a drug antibody, which drug antibody is an anti-C5 antibody that can specifically bind to human C5, in a serum or plasma sample with reduced target interference comprises the following steps:

a) incubating the serum or plasma sample at a pH value in the range of 4.7 to 5.5 for 1.5 to 2.5 hours, and optionally removing formed precipitate after the incubation, b) incubating the serum or plasma sample obtained in step a) at a pH value of about 2 for about 5 minutes, and optionally centrifuging the incubated sample to remove formed precipitate, c) adjusting the pH value to about 7.4, adding capture drug antibody conjugated to biotin and tracer drug antibody conjugated to digoxigenin to the serum or plasma sample obtained in step b) and incubating the mixture to form a capture antibody-anti-drug antibody-tracer antibody-complex, d) incubating the serum or plasma sample obtained in step c) with (strept)avidin conjugated to a solid surface to capture the capture antibody-anti-drug antibody-tracer antibody-complex, and optionally washing the surface, (and)

e) detecting and/or determining and/or quantifying the amount of anti-drug antibody by determining the digoxigenin in the complex formed in step d) by incubating with an anti-digoxigenin antibody conjugated to horseradish peroxidase and thereafter incubation with HPPA or TMB, and thereby detecting and/or determining and/or quantifying the amount of anti-drug antibody in the serum or plasma sample (correlating the formed complex to the amount of the ADA in the sample).

In one embodiment of all aspects the sample is from an animal. In one embodiment the animal is selected from a human being and an experimental animal. In one embodiment the sample is from an animal to which the drug had been administered prior to obtaining the sample. In one embodiment the sample is from a patient in need of a treatment with the drug to which the drug had been administered prior to obtaining the sample. In no case is the sample re-applied to a living being after the method as reported herein had been performed therewith.

In one embodiment of all aspects the sample is a human sample (human serum or plasma sample).

In one embodiment of all aspects the complexes are non-covalent complexes.

Generally, an immunoassay comprises the following steps:

a) immobilizing the capture antibody on a solid surface, and optionally washing the surface after the immobilization step to remove unbound and non-specifically bound capture antibody, b) incubating the immobilized capture antibody of step a) with a serum or plasma containing sample, which optionally has been diluted to have a concentration of the anti-drug antibody within the detection range of the immunoassay, to form a capture antibody-anti-drug antibody-complex, and optionally washing the surface after the incubation step to remove unbound and non-specifically bound sample, c) incubating the capture antibody-anti-drug antibody-complex of step b) with a labelled tracer antibody to form a capture antibody-anti-drug antibody-tracer antibody complex, and optionally washing the surface after the incubation step to remove unbound and non-specifically bound tracer antibody, d) incubating the capture antibody-anti-drug antibody-tracer antibody complex of step c) with an antibody specifically binding to the label of the tracer antibody conjugated to an enzyme to form a capture antibody-anti-drug antibody-tracer antibody-detection antibody complex, and optionally washing the surface after the incubation step to remove unbound and non-specifically bound detection antibody, e) incubating the capture antibody-anti-drug antibody-tracer antibody-detection antibody complex of step d) with a colorless substrate of the enzyme that upon action of the enzyme on the substrate is converted to a colored reaction product and determining the optical density after a predefined period of time, (and)

f) correlating the optical density determined in step e) with a calibration curve and thereby determining the amount of anti-drug antibody in the sample.

DETAILED DESCRIPTION OF THE INVENTION

For the analysis of therapeutic antibodies (drug or short D) as well as the respective antibodies against the therapeutic antibody (anti-drug antibody or short ADA) in samples of in vitro or in vivo origin a respective assay is necessary.

The ADA binds to its antigen (in vitro and in vivo), i.e. the therapeutic antibody/drug, and an equilibrium between free ADA and free drug, respectively, as well as mono- and di-complexed drug (assuming a bivalent monospecific drug) is formed. This equilibrium is dynamic, i.e. the change of the concentration of one component taking part in this equilibrium also changes the concentrations of all other components taking part in this equilibrium.

While the fraction of free, i.e. not bound, ADA correlates to the availability of drug for binding and binding capacity of ADA to its antigen, i.e. drug, in vivo, the determination of total ADA can be used to characterize the interaction between ADA and drug.

For full pharmacokinetic evaluation of a drug, e.g., the knowledge of ADA concentration, either free, i.e. drug-binding competent or in complex with the drug, in the systemic circulation is important. Free ADA can be evaluated as potential biomarker.

An assay for determining ADA in a sample can be interfered if the antigen of the drug is present in the sample. For pharmacokinetic evaluation the ADA fraction, which can bind or is bound to the drug, is important.

The terms "therapeutic antibody" and "drug" are used interchangeably herein. These terms are used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

In certain embodiments, the drug is a monospecific antibody. In one embodiment the drug is a monospecific, bivalent antibody. In one preferred embodiment the drug is a monoclonal, monospecific, bivalent antibody.

In certain embodiments, the drug is a multispecific antibody, e.g. a bispecific antibody. Multispecific antibodies are monoclonal antibodies that have binding specificities for at least two different antigens. In certain embodiments, one of the binding specificities is for a first antigen and the other is for a different second antigen. In certain embodiments, bispecific antibodies may bind to two different epitopes of the same antigen. Bispecific antibodies can be prepared as full length antibodies or antibody fragments. In one embodiment the antibody is a bispecific antibody, which specifically binds to a first and a second antigen. In one embodiment the bispecific antibody has i) a first binding specificity that specifically binds to a first antigen or a first epitope on an antigen, and ii) a second binding specificity that specifically binds to a second antigen or a second epitope on the (same) antigen. In one embodiment the second epitope on the same antigen is a non-overlapping epitope. In one embodiment the antibody is a bispecific, bivalent antibody. In one preferred embodiment the antibody is a monoclonal, bispecific, bivalent antibody.

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

The terms "anti-C5 antibody" and "an antibody that (specifically) binds to C5" refer to an antibody that is capable of binding C5 with sufficient affinity such that the antibody is useful as a diagnostic and/or therapeutic agent in targeting C5. In one embodiment, the extent of binding of an anti-C5 antibody to an unrelated, non-C5 protein is less than about 10% of the binding of the antibody to C5. In certain embodiments, an anti-C5 antibody binds to an epitope of C5 that is conserved among C5 from different species. In one preferred embodiment C5 is human C5.

The term "C5", as used herein, encompasses any native C5 from any vertebrate source, including mammals such as primates (e.g., humans and monkeys) and rodents (e.g., mice and rats). Unless otherwise indicated, the term "C5" refers to a human C5 protein having the amino acid sequence shown in SEQ ID NO: 30 and containing the beta chain sequence shown in SEQ ID NO: 31. The term encompasses "full-length", unprocessed C5 as well as any form of C5 that results from processing in the cell. The term also encompasses naturally occurring variants of C5, e.g., splice variants or allelic variants. The amino acid sequence of an exemplary human C5 is shown in SEQ ID NO: 30 ("wild-type" or "wt" C5). The amino acid sequence of an exemplary beta chain of human C5 is shown in SEQ ID NO: 31. The amino acid sequences of exemplary MG1, MG2 and MG1-MG2 domains of the beta chain of human C5 are shown in SEQ ID NO: 32, 33, and 34, respectively. The amino acid sequences of exemplary cynomolgus monkey and murine C5 are shown in SEQ ID NO: 35 and 96, respectively. Amino acid residues 1-19 of SEQ ID NOs: 30, 31, 34, 35, and 96 correspond to a signal sequence that is removed during processing in the cell and is thus missing from the corresponding exemplary amino acid sequence.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Monoclonal antibodies and their constant domains contain a number of reactive amino acid side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of antibodies is the aliphatic ε-amine of the amino acid lysine. In general, nearly all antibodies contain abundant lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and 6-amine groups of amino acids to form amide linkages. The anhydride rings open to create multivalent, metal-chelating arms able to bind tightly to metals in a coordination complex.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio)propionamido] hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodo-acetamides. Maleimides react rapidly at slight acidic to neutral pH.

Another common reactive group in antibodies are carboxylic acids. Antibodies contain carboxylic acid groups at the C-terminal position and within the side chains of aspartic acid and glutamic acid. The relatively low reactivity of carboxylic acids in water usually makes it difficult to use these groups to selectively modify polypeptides and antibodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic s-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment region (Fc-region) of an antibody, conjugation can be achieved through site-directed modification of the carbohydrate away from the antigen-binding site. A Schiffs base intermediate is formed, which can be reduced to an alkyl amine through the reduction of the intermediate with sodium cyanoborohydride (mild and selective) or sodium borohydride (strong) water-soluble reducing agents.

The conjugation of a tracer and/or capture and/or detection antibody to its conjugation partner can be performed by different methods, such as chemical binding, or binding via a binding pair. The term "conjugation partner" as used herein denotes e.g. solid supports, polypeptides, detectable labels, members of specific binding pairs. In one embodiment the conjugation of the capture and/or tracer and/or detection antibody to its conjugation partner is performed by chemically binding via N-terminal and/or s-amino groups (lysine), s-amino groups of different lysines, carboxy-, sulfhydryl-, hydroxyl-, and/or phenolic functional groups of the amino acid backbone of the antibody, and/or sugar alcohol groups of the carbohydrate structure of the antibody. In one embodiment the capture antibody is conjugated to its conjugation partner via a binding pair. In one preferred embodiment the capture antibody is conjugated to biotin and immobilization to a solid support is performed via solid support immobilized avidin or streptavidin. In one embodiment the capture antibody is conjugated to its conjugation partner via a binding pair. In one preferred embodiment the tracer antibody is conjugated to digoxigenin by a covalent bond as detectable label.

The term "sample" includes, but is not limited to, any quantity of a substance from a living thing or formerly living thing. Such living things include, but are not limited to, humans, mice, monkeys, rats, rabbits, and other animals. In one embedment the sample is obtained from a monkey, especially a cynomolgus monkey, or a rabbit, or a mouse, or rat, or a human. In one preferred embodiment the sample is a human sample. Such substances include, but are not limited to, in one embodiment whole blood, plasma or serum from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

Chromogens (fluorescent or luminescent groups and dyes), enzymes, NMR-active groups or metal particles, haptens, e.g. digoxigenin, are examples of "detectable labels". The detectable label can also be a photoactivatable crosslinking group, e.g. an azido or an azirine group. Metal chelates which can be detected by electrochemiluminescence are also preferred signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138. For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a binding pair. Examples of suitable binding pairs are antigen/antibody, biotin or biotin analogues such as aminobiotin, iminobiotin or desthiobiotin/avidin or Streptavidin, sugar/lectin, nucleic acid or nucleic acid analogue/complementary nucleic acid, and receptor/ligand, e.g., steroid hormone receptor/steroid hormone. In one preferred embodiment the first binding pair members comprise hapten, antigen and hormone. In one-preferred embodiment the hapten is selected from the group consisting of digoxin, digoxygenin and biotin and analogues thereof. The second partner of such binding pair, e.g. an antibody, Streptavidin, etc., usually is labeled to allow for direct detection, e.g., by the labels as mentioned above.

The term "immunoassay" denotes any technique that utilizes specifically binding molecules, such as antibodies, to capture and/or detect a specific target for qualitative or quantitative analysis. In general, an immunoassay is characterized by the following steps: 1) immobilization or capture of the analyte and 2) detection and measuring the analyte. The analyte can be captured, i.e. bound, on any solid surface, such as e.g. a membrane, plastic plate, or some other solid surface.

Immunoassays can be performed generally in three different formats. One is with direct detection, one with indirect detection, or by a sandwich assay. The direct detection immunoassay uses a detection (or tracer) antibody that can be measured directly. An enzyme or other molecule allows for the generation of a signal that will produce a color, fluorescence, or luminescence that allow for the signal to be visualized or measured (radioisotopes can also be used, although it is not commonly used today). In an indirect assay a primary antibody that binds to the analyte is used to provide a defined target for a secondary antibody (tracer antibody) that specifically binds to the target provided by the primary antibody (referred to as detector or tracer antibody). The secondary antibody generates the measurable signal. The sandwich assay makes use of two antibodies, a capture and a trace (detector) antibody. The capture antibody is used to bind (immobilize) analyte from solution or bind to it in solution. This allows the analyte to be specifically removed from the sample. The tracer (detector) antibody is used in a second step to generate a signal (either directly or indirectly as described above). The sandwich format requires two antibodies each with a distinct epitope on the target molecule. In addition, they must not interfere with one another as both antibodies must be bound to the target at the same time.

Embodiments of the Method According to the Invention

Drug interference in an ADA assay is a generally known phenomenon, but not the interference of the target of the drug in an ADA assay.

Generally, after acid dissociation a neutralization step follows the acid or base dissociation to allow binding partners to bridge anew causing the interference factor if still in solution to re-bind as well, maintaining the issue.

Many approaches have been used to mitigate this problem such as acid or base dissociation, competitive inhibition of interference using specific antibodies, removal of the interference factors, solid phase extraction with acid dissociation (SPEAD), affinity capture elution (ACE) and many others. The use of acid dissociation in a bridging assay has shown some improvement in drug tolerance for the detection of ADA (see e.g. Moxness, M., et al., Clin. Chem. 51. (10), 1983; Patton, A., et al., J. Immunol. Methods 304 (2005) 189).

PEG precipitation of the target molecule or immune complex is size (or molecular weight, MW) based and PEG concentration dependent. The higher the PEG concentrations, the lower MW targets it will precipitate. To reduce the precipitation of non-specific serum proteins such as albumin and immunoglobulin, a low concentration of PEG is used to precipitate large MW drug:ADA immune complexes. Using the principle of precipitation, coupled with acid dissociation and capturing on high capacity surface under acidic conditions (preventing the binding partners from re-binding), allows specific detection of ADA or drug or drug target using specific detection reagents.

Acid dissociation is used commonly to disrupt drug-ADA-complexes and, thus, to release ADA from said immune-complexes. The released (free) ADA can form complexes with the detection antibody in a subsequent step. The acid dissociation step can shorten the overall assay time compared to a classical ADA assay (without acid dissociation step). Generally, the focus is on comparable sensitivity.

In general, a standard ADA assay bears the disadvantage of a long incubation time for forming the new equilibrium between the ADA and the reagents in the presence of residual drug. If a short incubation time is applied only a low drug tolerance can be obtained (=low sensitivity with residual drug).

The formation of the measurable complexes takes time and is depending on the association rate constant of the ADA to the reagents. For the standard ADA assay the dissociation rate constant of the immune-complexes is the time limiting step. For this reason, longer incubation times (commonly overnight) are applied to the incubation of the sample and reagents.

Thus, acid dissociation is predominantly a complex dissociation procedure.

One aspect according to the current invention is an immunoassay for detecting and/or determining and/or quantifying the amount of anti-drug antibody, which anti-drug antibody can specifically bind to a drug antibody, which drug antibody can specifically bind to a therapeutic target, in a serum or plasma sample comprising the following steps:
  a) incubating an immobilized capture antibody with a serum or plasma sample comprising drug, target and anti-drug antibody, to form a capture antibody-anti-drug antibody complex,
  b) washing the complex formed in step a) with a buffer comprising a sugar and a detergent, which has a pH value of about the pI of the target,
  c) incubating for 12 to 24 hours the washed complex of step b) with a labelled tracer antibody to form a capture antibody-anti-drug antibody-tracer antibody complex, (and)
  d) detecting and/or determining and/or quantifying the amount of anti-drug antibody by determining the detectable label in the complex formed in step c).

In one embodiment the sugar is saccharose, the detergent is polyethylene glycol dodecyl ether, the drug is an anti-C5 antibody, the target is human C5 and the buffer has a pH value of about 5.5.

One aspect according to the current invention is an immunoassay for detecting and/or determining and/or quantifying the amount of anti-drug antibody, which anti-drug antibody can specifically bind to a drug antibody, which drug antibody can specifically bind to a therapeutic target, in a serum or plasma sample comprising the following steps:
  a) incubating the serum or plasma sample at a pH value that is about the pI value of the target, and optionally removing formed precipitate after the incubation,
  b) incubating the serum or plasma sample obtained in step a) at a pH value of about 2, and optionally centrifuging the incubated sample to remove formed precipitate,
  c) adjusting the pH value to about 7.4, adding capture antibody conjugated to a first member of a binding pair and tracer antibody conjugated to a detectable label to the serum or plasma sample obtained in step b) and incubating the mixture to form a capture antibody-anti-drug antibody-tracer antibody-complex, (and)
  d) measuring and/or determining and/or quantifying the complex formed in step c) and thereby detecting and/or determining and/or quantifying the amount of anti-drug antibody in the serum or plasma sample.

In one embodiment the step of measuring and/or determining and/or quantifying the capture antibody-anti-drug antibody-tracer antibody-complex (step d)) comprises the steps of d1) incubating the serum or plasma sample obtained in step c) with the second member of the binding pair conjugated to a solid surface to capture the capture antibody-anti-drug antibody-tracer antibody-complex, and optionally washing the surface, (and)

d2) detecting and/or determining and/or quantifying the amount of anti-drug antibody by determining the detectable label in the complex formed in step d1).

In one embodiment the immunoassay for detecting and/or determining and/or quantifying the amount of anti-drug antibody, which anti-drug antibody can specifically bind to a drug antibody, which drug antibody is an anti-C5 antibody that can specifically bind to human C5, in a serum or plasma sample comprises the following steps:

a) incubating the serum or plasma sample at a pH value in the range of 4.7 to 5.5 for 1.5 to 2.5 hours, and optionally removing formed precipitate after the incubation, b) incubating the serum or plasma sample obtained in step a) at a pH value of about 2 for about 5 minutes, and optionally centrifuging the incubated sample to remove formed precipitate, c) adjusting the pH value to about 7.4, adding capture drug antibody conjugated to biotin and tracer drug antibody conjugated to digoxigenin to the serum or plasma sample obtained in step b) and incubating the mixture to form a capture antibody-anti-drug antibody-tracer antibody-complex, d) incubating the serum or plasma sample obtained in step c) with (strept)avidin conjugated to a solid surface to capture the capture antibody-anti-drug antibody-tracer antibody-complex, and optionally washing the surface, (and)

e) detecting and/or determining and/or quantifying the amount of anti-drug antibody by determining the digoxigenin in the complex formed in step d) by incubating with an anti-digoxigenin antibody conjugated to horseradish peroxidase and thereafter incubation with HPPA or TMB, and thereby detecting and/or determining and/or quantifying the amount of anti-drug antibody in the serum or plasma sample.

The assay as reported herein addresses the interference of the target of a therapeutic drug in the measurement and/or determination and/or quantification of anti-drug antibodies in a serum or plasma sample.

Normally the interference from drug in the determination and/or measurement and/or quantification of anti-drug antibodies (ADA) in a serum or plasma sample has to be addressed. Measures therefore can be high specific sensitivity for the anti-drug antibody, influencing the equilibrium in the sample towards the free anti-drug antibody, dissociating ADA-drug complexes by sample pre-treatment, detecting ADA-drug complexes, or enriching ADA.

But the interference of the target of the drug in the sample is not addressed thereby. The immunoassay as reported herein is exemplified in the following with a therapeutic anti-C5 antibody. This is presented merely as an exemplification of the currently reported immunoassay and shall not be construed as a limitation of the current invention.

Human C5 has a serum concentration of approximately 70 µg/ml (approximately 368 nM).

Different sample dilutions (1:100, 1:1000), different capture antibody as well as tracer antibody concentration (500 ng/ml each, 1000 ng/ml each, 1500 ng/ml each, 2000 ng/ml each), different peroxidase concentrations (5 mU, 10 mU, 25 mU, 50 mU at 1000 ng/ml capture and tracer antibody concentration) were evaluated (see FIGS. 1 and 2). For all experiments an overnight sample incubation with reagents was performed.

The invention is based, at least in part, on the finding that the capture antibody and tracer antibody concentration should be at least 500 ng/ml whereby at 1500 ng/ml or more no further signal gain could be achieved.

But a rather high background is present.

In the presence of 1% (v/v) human serum non-specific binding could be observed. The blocking of the plate with BSA did not solve problem of non-specific binding.

without BSA:

|  | Bi/Dig cut-off | Bi/Dig individual | —/— | | Bi/— | | —/Dig | | Bi/Dig HPS cut-off | |
|---|---|---|---|---|---|---|---|---|---|---|
|  | | | neg./pos. relative to buffer cut-off | | | | | | | |
| HPS | 1631 | 2199 | 66 | 58 | 78 | 78 | 417 | 757 | 4061 | 4070 |
| | | 2198 | 83 | 83 | 68 | 72 | 108 | 126 | 1286 | 1302 |
| | | 2201 | 54 | 60 | 58 | 53 | 74 | 63 | 644 | 669 |
| | | 2195 | 59 | 58 | 53 | 51 | 98 | 88 | 3612 | 3763 |
| buffer | 84 | 2205 | 55 | 75 | 62 | 56 | 89 | 90 | 3591 | 3650 |
| | | 2202 | 53 | 54 | 72 | 51 | 283 | 289 | 5054 | 5200 |
| | | 2194 | 575 | 568 | 302 | 281 | 966 | 1053 | 7336 | 7444 |
| | | 2196 | 129 | 178 | 97 | 119 | 144 | 159 | 1336 | 1379 | with BSA:

|  | Bi/Dig cut-off | Bi/Dig individual | —/— | | Bi/— | | —/Dig | | Bi/Dig HPS cut-off | |
|---|---|---|---|---|---|---|---|---|---|---|
|  | | | neg./pos. relative to buffer cut-off | | | | | | | |
| HPS | 1690 | 2199 | 63 | 64 | 75 | 59 | 542 | 709 | 4024 | 3997 |
| | | 2198 | 89 | 96 | 73 | 85 | 112 | 129 | 1294 | 1286 |
| | | 2201 | 55 | 51 | 51 | 51 | 61 | 66 | 653 | 663 |
| | | 2195 | 60 | 54 | 47 | 56 | 79 | 91 | 3589 | 3660 |
| buffer | 71 | 2205 | 51 | 52 | 52 | 52 | 77 | 83 | 3621 | 3621 |
| | | 2202 | 64 | 54 | 59 | 60 | 271 | 265 | 5175 | 5192 |
| | | 2194 | 640 | 620 | 318 | 317 | 1060 | 1060 | 7549 | 7522 |
| | | 2196 | 152 | 157 | 100 | 110 | 152 | 178 | 1370 | 1380 |

It can be seen that even in the absence of the Bi/Dig reagents a high signal is obtained (column "−/−"). Beside others still non-specific binding of detection reagent can be seen (column "−/Dig").

By the addition of a detergent (Brij 35) a reduction of non-specific binding could be seen (see "−/−", "Bi/−" and "−/Dig" columns). In the absence of the detergent the cut-point (CP) was 10240 (approx. 2562 ng/ml) (see "Bi/Dig" column), whereas in the presence of the detergent the CP was 4708 (approx. 817 ng/ml) (see "Bi/Dig" column). But the variation coefficient (CV) of the individuals is high.

without detergent:

|  | Bi/Dig cut-off | Bi/Dig individual | −/− | | Bi/− | | −/Dig | | Bi/Dig HPS cut-off | |
|---|---|---|---|---|---|---|---|---|---|---|
|  | | | neg./pos. relative to buffer cut-off | | | | | | | |
| HPS | 1471 | 2199 | 195 | 198 | 98 | 86 | 992 | 1113 | 7045 | 6993 |
| | | 2198 | 167 | 179 | 66 | 62 | 185 | 209 | 1359 | 1388 |
| | | 2201 | 192 | 157 | 83 | 86 | 189 | 181 | 714 | 749 |
| | | 2195 | 256 | 184 | 63 | 63 | 355 | 393 | 4841 | 4805 |
| buffer | 216 | 2205 | 201 | 192 | 66 | 65 | 370 | 317 | 4431 | 4489 |
| | | 2202 | 153 | 172 | 78 | 86 | 620 | 584 | 6959 | 7110 |
| | | 2194 | 152 | 180 | 78 | 82 | 687 | 807 | 10557 | 10249 |
| | | 2196 | 230 | 243 | 81 | 89 | 241 | 197 | 1410 | 1219 | with detergent:

|  | Bi/Dig cut-off | Bi/Dig individual | −/− | | Bi/− | | −/Dig | | Bi/Dig HPS cut-off | |
|---|---|---|---|---|---|---|---|---|---|---|
|  | | | neg./pos. relative to buffer cut-off | | | | | | | |
| HPS | 1044 | 2199 | 66 | 65 | 65 | 71 | 160 | 167 | 3026 | 2975 |
| | | 2198 | 53 | 53 | 51 | 56 | 63 | 75 | 828 | 862 |
| | | 2201 | 63 | 55 | 58 | 54 | 63 | 66 | 470 | 489 |
| | | 2195 | 55 | 54 | 53 | 55 | 103 | 100 | 2456 | 2515 |
| buffer | 144 | 2205 | 54 | 53 | 52 | 54 | 94 | 99 | 2452 | 2431 |
| | | 2202 | 53 | 56 | 57 | 54 | 123 | 169 | 3498 | 3598 |
| | | 2194 | 55 | 58 | 58 | 55 | 173 | 145 | 4690 | 4648 |
| | | 2196 | 64 | 69 | 54 | 67 | 72 | 81 | 856 | 882 |

The exchange of the substrate for the detection enzyme can reduce the signal-to-noise (S/N) ratio.

with detergent and HPPA (3-(4-hydroxyphenyl) propionic acid):

|  | Bi/Dig cut-off | Bi/Dig individual | −/− | | Bi/− | | −/Dig | | Bi/Dig HPS cut-off | |
|---|---|---|---|---|---|---|---|---|---|---|
|  | | | neg./pos. relative to buffer cut-off | | | | | | | |
| HPS | 1044 | 2199 | 66 | 65 | 65 | 71 | 160 | 167 | 3026 | 2975 |
| | | 2198 | 53 | 53 | 51 | 56 | 63 | 75 | 828 | 862 |
| | | 2201 | 63 | 55 | 58 | 54 | 63 | 66 | 470 | 489 |
| | | 2195 | 55 | 54 | 53 | 55 | 103 | 100 | 2456 | 2515 |
| buffer | 144 | 2205 | 54 | 53 | 52 | 54 | 94 | 99 | 2452 | 2431 |
| | | 2202 | 53 | 56 | 57 | 54 | 123 | 169 | 3498 | 3598 |
| | | 2194 | 55 | 58 | 58 | 55 | 173 | 145 | 4690 | 4648 |
| | | 2196 | 64 | 69 | 54 | 67 | 72 | 81 | 856 | 882 | with detergent and TMB (3,3',5,5'-tetramethyl-benzidine):

|  | Bi/Dig | Bi/Dig | −/− | | Bi/− | | −/Dig | | Bi/Dig | |
|---|---|---|---|---|---|---|---|---|---|---|
| 50000 | 2.136 | 2.138 | 0.046 | 0.049 | 0.030 | 0.031 | 0.033 | 0.033 | 0.036 | 0.037 | 0.124 | 0.122 |
| 17857 | 1.126 | 1.119 | 0.043 | 0.047 | 0.029 | 0.029 | 0.029 | 0.029 | 0.032 | 0.031 | 0.048 | 0.050 |
| 6378 | 0.546 | 0.538 | 0.046 | 0.049 | 0.032 | 0.031 | 0.030 | 0.030 | 0.033 | 0.033 | 0.042 | 0.041 |
| 2278 | 0.313 | 0.310 | 0.045 | 0.048 | 0.028 | 0.030 | 0.030 | 0.029 | 0.033 | 0.033 | 0.100 | 0.099 |
| 813 | 0.162 | 0.162 | 0.029 | 0.033 | 0.028 | 0.028 | 0.029 | 0.027 | 0.033 | 0.032 | 0.092 | 0.092 |
| 291 | 0.084 | 0.092 | 0.029 | 0.033 | 0.029 | 0.030 | 0.030 | 0.026 | 0.035 | 0.035 | 0.127 | 0.127 |
| 104 | 0.068 | 0.060 | 0.028 | 0.032 | 0.028 | 0.029 | 0.030 | 0.028 | 0.034 | 0.035 | 0.154 | 0.158 |
| blank | 0.050 | 0.050 | 0.030 | 0.033 | 0.030 | 0.031 | 0.031 | 0.029 | 0.033 | 0.032 | 0.050 | 0.049 |

When using HPPA the cut-point (CP) was 4708 (approx. 817 ng/ml), whereas when using TMB the CP was 0.162 (approx. 845 ng/ml).

|  | HPPA pool blank | S/N | TMB pool blank | S/N |
|---|---|---|---|---|
| HPS buffer | 1389 178 | 7.8 | 0.044 0.023 | 1.9 |

To avoid long-term incubation (over-night incubation) an acid dissociation step was introduced. The method then comprises a 30-minute incubation at pH 2, followed by pH adjustment to pH 7.4, addition of the biotinylated capture antibody and the digoxigenylated tracer antibody and a one-hour incubation.

Based on 8 individual samples an average value of 4410 fluorescence units with a coefficient of variation of 9% was determined. The cut-point was 5059 fluorescent units (1915 ng/ml). Thus, the introduction of the acid dissociation step did not result in an improvement in sensitivity.

The presence of plasma or serum did not significantly change the assay characteristics. Human and NHP serum provide for similar assay results (see FIG. 3).

Horse and rabbit serum provide similar results as buffer. Horse and rabbit C5 are not cross reactive. The blank signal of C5 depleted human serum is comparable to buffer and signals by dilution 4 are lower than with human pool serum (see FIG. 4).

The assay performance was impaired by the increase of horse serum and thereby horse C5 content in the sample (see FIG. 5).

Likewise, an addition of human C5 causes an increase in the signal confirming that the assay interference stems from the target of the therapeutic antibody in the sample (see FIG. 6).

It has been found that calibration of a bridging assay is possible with both, C5 and control pAb, i.e. C5 is causing signals in the assay (see FIG. 7). Without being bound by this theory it is assumed that sticky C5 aggregates are causing the problem (see FIG. 8 (wash buffer pH 7.4) and FIG. 9 (wash buffer pH 5.5)).

It has been found that C5 and pAb both bind to the therapeutic drug. Higher Drug to C5 ratio results in lower responses indicating no non-specific binding (see BIAcore data in FIG. 10).

It has been found that C5 and pAb both bind to the therapeutic drug using a therapeutic drug pre-coated surface. After capturing of C5 the surface is capable to bind therapeutic drug suggesting a that free epitopes are still present, which is the case for aggregated C5 (see FIG. 11).

Based on these findings the method has been further adapted by using an enhanced was step of washing 6 times with a buffer of a pH value of 5.5. Without being bound by this theory this reduces the amount/quantity of captured aggregates.

results in 1% serum; S/N=7; cut-point=2429 FU (0.82 ng/ml)

| individual | average OD | concentration |
|---|---|---|
| 2199 | 2005 | >blank < 104 ng/ml |
| 2198 | 1364 | >blank < 104 ng/ml |
| 2201 | 374 | <blank |
| 2195 | 1050 | >blank < 104 ng/ml |
| 2205 | 970 | >blank < 104 ng/ml |
| 2202 | 1881 | >blank < 104 ng/ml |
| 2194 | 1593 | >blank < 104 ng/ml |
| 2196 | 2188 | >blank < 104 ng/ml | results in 0.1% serum; S/N=2; cut-point=2660 FU (0.84 ng/ml)

| individual | average OD | concentration |
|---|---|---|
| 2199 | 2670 | >blank < 104 ng/ml |
| 2198 | 1822 | >blank < 104 ng/ml |
| 2201 | 1187 | <blank |
| 2195 | 1507 | >blank < 104 ng/ml |
| 2205 | 1403 | >blank < 104 ng/ml |
| 2202 | 2148 | >blank < 104 ng/ml |
| 2194 | 1840 | >blank < 104 ng/ml |
| 2196 | 2262 | >blank < 104 ng/ml |

The S/N ratio lowers with dilution. The cut-point value and the lowest calibrator are similar in 1% and 0.1% serum containing samples. The cut-point was near 100 ng/ml for positive control in serum.

The assay was adapted to the findings as reported herein to reduce the formation of aggregates by performing an incubation at 4° C. incubation for about 16 hours (overnight), by the addition of 6.5 wt-% saccharose in assay buffer, and by the addition of the non-ionic detergent Brij 35.

The assay was further adopted by using a wash buffer with a pH value of 5.5 to reduce therapeutic drug to target, i.e. C5, interaction.

Based on the findings as outlined above a new assay format was established wherein the C5 aggregates present in the sample are removed prior to the determination and/or measurement and/or quantification of the anti-drug antibody in ta sample.

The new assay format as reported herein comprises a specific precipitation step wherein the target of the therapeutic antibody is precipitated at a pH value of about its pI value. In case of an anti-C5 antibody as therapeutic drug the target is human C5 and the precipitation is achieved by an incubation at a pH value in the range of 4.7 to 5.5. In one embodiment the incubation is at a pH value of about 5. In one preferred embodiment the incubation is at a pH value of about 5 for about 2 hours optionally with agitation.

The new assay format as reported herein comprises after the specific precipitation step an acid dissociation step. In this step, without being bound by this theory, the ADA (anti-anti-C5 antibody-antibody; anti-drug antibody) is dissociated from the precipitate. In one preferred embodiment the acid dissociation is by an incubation at a pH value of about 2 for about 5 minutes.

The new assay format as reported herein comprises optionally after the acid dissociation step a centrifugation step.

The new assay format as reported herein comprises after the acid dissociation step the step of adjusting the pH value of the sample to about 7.4, followed by the addition of the capture antibody and the tracer antibody with subsequent incubation. In one embodiment the capture antibody and the tracer antibody are the drug antibody. In one embodiment the capture antibody is conjugated to a first member of a binding pair. In one embodiment the binding pair is selected from biotin/(strept)avidin, hapten/anti-hapten antibody, nucleic acid/complementary nucleic acid, and ligand/ligand receptor. In one preferred embodiment the binding pair is biotin/(strept)avidin. In one preferred embodiment the capture antibody is conjugated to biotin. In one embodiment the tracer antibody is conjugated to a detectable label.

The new assay format as reported herein comprises after the incubation step with the capture and tracer antibody the immobilization of the capture antibody-anti-drug antibody-tracer antibody complex on a solid phase derivatized with the second member of the binding pair. In one preferred embodiment the second member of the binding pair is (strept)avidin.

The new assay format as reported herein comprises after the immobilization step the step of measuring and/or determining and/or quantifying the amount of the immobilized complex by incubating the immobilized complex with an antibody specifically binding to the detectable label conjugated to an enzyme catalyzing the conversion of a colorless substrate into a colored product followed by incubation with the colorless substrate of the enzyme, determination of the amount of formed colored product and correlating the amount of formed colored product with a calibration curve and thereby determining the amount of anti-drug antibody in the sample. In one embodiment the detectable label is a hapten. In one embodiment the hapten is selected from biotin, digoxigenin, theophylline and bromo desoxy uridine. In one preferred embodiment the detectable label is digoxygenin. In one preferred embodiment the enzyme is horseradish peroxidase. In one embodiment the colorless substrate is ABTS or HPPA or TMB. In one preferred embodiment the colorless substrate is TMB.

The results obtained with a method as reported herein (C5 precipitation approach) based on 30 individuals is presented in the following tables.

data of the calibration curve:

| concentration [ng/ml] | average [FU] | STDEV [FU] | CV [%] | calculated [ng/ml] | recovery [%] |
|---|---|---|---|---|---|
| 50000 | 41337 | 146 | 0.4 | 50054 | 100 |
| 17857 | 18883 | 151 | 0.8 | 19421 | 109 |
| 6378 | 7290 | 33 | 0.4 | 6107 | 96 |
| 2278 | 3010 | 91 | 3.0 | 2050 | 90 |
| 813 | 1475 | 16 | 1.1 | 827 | 102 |
| 291 | 774 | 9 | 1.2 | 347 | 119 |
| 104 | 340 | 4 | 1.2 | 96 | 93 |
| blank | 118 | 6 | 5.4 | | |

FU signals of the 30 individual samples:

| | | | |
|---|---|---|---|
| 102 | 103 | 116 | 132 |
| 133 | 98 | 96 | 97 |
| 105 | 100 | 99 | 113 |
| 112 | 112 | 101 | 102 |
| 114 | 122 | 115 | 109 |
| 116 | 123 | 130 | 112 |
| 136 | 131 | 133 | 116 |
| | 123 | | 133 |

| | |
|---|---|
| average | 114 |
| STDEV | 12.7 |
| CV | 11% |
| CP | 135 |

The new assay as reported herein has a suitable to high dynamic range, it is sensitive and addresses the interference from individual target levels present in the sample to be analyzed.

For the sample processing it is not required to remove the precipitate formed in the incubation step at about the pI of the target prior to the analysis. Without acid incubation step the interference is present (see FIG. 12):

| A: with centrifugation after acid treatment step (FIG. 12, 2) | |
|---|---|
| average | 114 |
| STDEV | 7.9 |
| CV | 7% |
| CP [FU] | 127 |
| CP [ng/ml] | 12 |
| B: without centrifugation after acid treatment step (FIG. 12, 1) | |
| average | 98 |
| STDEV | 9.3 |
| CV | 9% |
| CP [FU] | 113 |
| CP [ng/ml] | 17 |
| C: no acid incubation step (FIG. 12, 3) | |
| average | 3290 |
| STDEV | 4353 |
| CV | 132% |
| CP [FU] | 10428 |
| CP [ng/ml] | 2084 |

The calibration with positive control, long incubation time, and pH 5.5 wash is shown in FIG. 13. The average of 15 individuals is 119, the blank pool value is 123, and the cut-point is 135.

The calibration with polyclonal antibody, long incubation time, and pH 7.4 wash is shown in FIG. 14. The average of 15 individuals is 145, the blank pool value is 157, and the cut-point is 193.

The calibration with polyclonal antibody, short incubation time, and pH 5.5 wash is shown in FIG. 15. The average of 15 individuals is 124, the blank pool value is 115, and the cut-point is 247.

The calibration with polyclonal antibody in the presence of C5, 2-hour incubation at pH 5, and pH 5.5 wash is shown in FIG. 16.

The calibration with polyclonal antibody in the presence of C5, 2-hour incubation at pH 5, and pH 7.5 wash is shown in FIG. 17.

The calibration with polyclonal antibody in the presence of C5, 30-minute incubation at pH 2, and pH 5.5 wash is shown in FIG. 18 (ADA assay using acid dissociation according to the art).

Exemplary Drug Antibody for Specific Embodiments of the Invention

US 2016/0167054 discloses anti-C5 antibodies and methods of using the same. In some embodiments, an isolated anti-C5 antibody disclosed binds to an epitope within the beta chain of C5 with a higher affinity at neutral pH than at acidic pH.

C5 is a 181 kDa protein found in normal serum at approximately 71 μg/ml (0.4 μM). C5 is glycosylated with about 1.5-3% of its mass attributed to carbohydrate. Mature C5 is a heterodimer of 106 kDa alpha chain that is disulfide linked to 66 kDa beta chain. C5 is synthesized as a single chain precursor protein (pro-C5 precursor) of 1577 amino acids (see, e.g., U.S. Pat. Nos. 6,355,245 and 7,432,356). The pro-C5 precursor is cleaved to yield the beta chain as an amino terminal fragment and the a chain as alpha carboxyl terminal fragment. The alpha chain and the beta chain polypeptide fragments are connected to each other via a disulfide bond and constitute the mature C5 protein.

Mature C5 is cleaved into the C5a and C5b fragments during activation of the complement pathways. C5a is cleaved from the alpha chain of C5 by C5 convertase as an amino terminal fragment comprising the first 65 amino acids of the alpha chain. The remaining portion of mature C5 is fragment C5b, which contains the rest of the alpha chain disulfide bonded to the beta chain. Approximately 20% of the 11 kDa mass of C5a is attributed to carbohydrate.

C5a is an anaphylatoxin. C5b combines with C6, C7, C8 and C9 to form the membrane attack complex (MAC, C5b-9, terminal complement complex (TCC)) at the surface of the target cell. When sufficient numbers of MACs are inserted into target cell membranes, MAC pores are formed to mediate rapid osmotic lysis of the target cells.

Anaphylatoxins can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract granulocytes such as neutrophils, eosinophils, basophils and monocytes to the site of complement activation.

The activity of C5a is regulated by the plasma enzyme carboxypeptidase N that removes the carboxy-terminal arginine from C5a forming C5a-des-Arg derivative. C5a-des-Arg exhibits only 1% of the anaphylactic activity and polymorpho nuclear chemotactic activity of unmodified C5a.

While a properly functioning complement system provides a robust defense against infecting microbes, inappropriate regulation or activation of complement has been implicated in the pathogenesis of a variety of disorders including, e.g., rheumatoid arthritis (RA); lupus nephritis; ischemia-reperfusion injury; paroxysmal nocturnal hemoglobinuria (PNH); atypical hemolytic uremic syndrome (aHUS); dense deposit disease (DDD); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis (see, e.g., Holers et al., Immunol. Rev. 223 (2008) 300-316). Therefore, inhibition of excessive or uncontrolled activations of the complement cascade can provide clinical benefits to patients with such disorders, especially to patients with Paroxysmal nocturnal hemoglobinuria (PNH).

Eculizumab is a humanized monoclonal antibody directed against the complement protein C5, and the first therapy approved for the treatment of paroxysmal nocturnal hemoglobinuria (PNH) and atypical hemolytic uremic syndrome (aHUS) (see, e.g., Dmytrijuk et al., The Oncologist 13 (2008) 894-910). Eculizumab inhibits the cleavage of C5 into C5a and C5b by C5 convertase, which prevents the generation of the terminal complement complex C5b-9. Both C5a and C5b-9 cause the terminal complement-mediated events that are characteristic of PNH and aHUS (see also, WO 2005/065607, WO 2007/96586, WO 2008/060790, and WO 2010/054403). Several reports have described other anti-C5 antibodies. For example, WO 86/28707 described an anti-C5 antibody which binds to the alpha chain of C5 but does not bind to C5a, and blocks the activation of C5, while WO 2002/30886 described an anti-C5 monoclonal antibody which inhibits C5a formation. On the other hand, WO 2004/006653 described an anti-C5 antibody which recognizes the proteolytic site for C5 convertase on the alpha chain of C5, and inhibits the conversion of C5 to C5a and C5b. WO 2010/015608 described an anti-C5 antibody which has an affinity constant of at least 1×10E7 M−1. In one embodiment the drug is Eculizumab.

In some embodiments, the method is for the detection of an ADAs against an anti-C5 antibody binding to an epitope within the beta chain of C5. In some embodiments, the anti-C5 antibody binds to an epitope within the MG1-MG2 domain of the beta chain of C5. In some embodiments, the anti-C5 antibody binds to an epitope within a fragment consisting of amino acids 27-115 of the beta chain (SEQ ID NO: 31) of C5. In some embodiments, the anti-C5 antibody binds to an epitope within the beta chain (SEQ ID NO: 31) of C5 which comprises at least one fragment selected from the group consisting of amino acids 38-48, 61-67, and 98-101. In some embodiments, the anti-C5 antibody binds to an epitope within a fragment of the beta chain (SEQ ID NO: 31) of C5 which comprises at least one amino acid residue selected from the group consisting of Glu48, Asp51, His61, His63, Lys100, and His101 of SEQ ID NO: 31. In further embodiments, the antibody binds to C5 with a higher affinity at neutral pH than at acidic pH. In further embodiments, the antibody binds to C5 with a higher affinity at pH 7.4 than at pH 5.8. In another embodiment, the anti-C5 antibody binds to the same epitope as an antibody described in Table 1. In further embodiments, the antibody binds to the same epitope as an antibody described in Table 1 with a higher affinity at pH 7.4 than at pH 5.8. In a further embodiment, the anti-C5 antibody binds to the same epitope as an antibody described in Tables 2 or 3. In further embodiments, the antibody binds to the same epitope as an antibody described in Tables 2 or 3 with a higher affinity at pH 7.4 than at pH 5.8.

TABLE 1

| antibody | SEQ ID NO: | | | | | | | |
|---|---|---|---|---|---|---|---|---|
| | VH | VL | HVR-H1 | HVR-H2 | HVR-H3 | HVR-L1 | HVR-L2 | HVR-L3 |
| CFA0305 | 1 | 11 | 36 | 46 | 56 | 66 | 76 | 86 |
| CFA0307 | 2 | 12 | 37 | 47 | 57 | 67 | 77 | 87 |
| CFA0357 | 3 | 13 | 38 | 48 | 58 | 68 | 78 | 88 |
| CFA0501 | 4 | 14 | 39 | 49 | 59 | 69 | 79 | 89 |
| CFA0538 | 5 | 15 | 40 | 50 | 60 | 70 | 80 | 90 |
| CFA0590 | 6 | 16 | 41 | 51 | 61 | 71 | 81 | 91 |
| CFA0567 | 7 | 17 | 42 | 52 | 62 | 72 | 82 | 92 |
| CFA0573 | 8 | 18 | 43 | 53 | 63 | 73 | 83 | 93 |
| CFA0576 | 9 | 19 | 44 | 54 | 64 | 74 | 84 | 94 |

TABLE 2

| antibody | VH | HVR-H1 | HVR-H2 | HVR-H3 |
|---|---|---|---|---|
| 305L05 | 10 | 45 | 55 | 65 |
| 305L015 | 97 | 108 | 109 | 112 |
| 305L016 | 98 | 108 | 110 | 112 |
| 305L018 | 99 | 108 | 109 | 112 |
| 305L019 | 100 | 108 | 109 | 112 |
| 305L020 | 100 | 108 | 109 | 112 |
| 305L022 | 100 | 108 | 109 | 112 |
| 305L023 | 101 | 108 | 111 | 112 |

TABLE 3

| antibody | VL | HVR-L1 | HVR-L2 | HVR-L3 |
|---|---|---|---|---|
| 305L05 | 20 | 75 | 85 | 95 |
| 305L015 | 102 | 113 | 114 | 116 |
| 305L016 | 102 | 113 | 114 | 116 |
| 305L018 | 102 | 113 | 114 | 116 |
| 305L019 | 102 | 113 | 114 | 116 |
| 305L020 | 103 | 113 | 114 | 116 |
| 305L022 | 104 | 113 | 115 | 116 |
| 305L023 | 104 | 113 | 115 | 116 |

In certain embodiments, the anti-C5 antibody competes for binding to C5 with an antibody comprising a VH and VL pair selected from: (a) a VH of SEQ ID NO: 01 and a VL of SEQ ID NO: 11; (b) a VH of SEQ ID NO: 05 and a VL of SEQ ID NO: 15; (c) a VH of SEQ ID NO: 04 and a VL of SEQ ID NO: 14; (d) a VH of SEQ ID NO: 06 and a VL of SEQ ID NO: 16; (e) a VH of SEQ ID NO: 02 and a VL of SEQ ID NO: 12; (f) a VH of SEQ ID NO: 03 and a VL of SEQ ID NO: 13; (g) a VH of SEQ ID NO: 09 and a VL of SEQ ID NO: 19; (h) a VH of SEQ ID NO: 07 and a VL of SEQ ID NO: 17; (i) a VH of SEQ ID NO: 08 and a VL of SEQ ID NO: 18; and (j) a VH of SEQ ID NO: 10 and a VL of SEQ ID NO: 20.

In certain embodiments, the anti-C5 antibody is for use as a medicament. In one embodiment the anti-C5 antibody is used in treating a complement-mediated disease or condition which involves excessive or uncontrolled activation of C5. In additional embodiments, the anti-C5 antibody is used in treating diseases or disorders that include but are not limited to, paroxysmal nocturnal hemoglobinuria (PNH), age-related macular degeneration, myocardial infarction, rheumatoid arthritis, osteoporosis, osteoarthritis, and inflammation. The anti-C5 antibody is used to enhance the clearance of C5 from plasma.

In certain embodiments, the method is for the detection of ADAs against an anti-C5 antibody comprising a VH as in any of the embodiments provided above and a heavy chain constant region comprising the amino acid sequence of any one of SEQ ID NOs: 27, 28, 29, 105, 106, and 107. In certain embodiments, the method is for the detection of an anti-C5 antibody comprising a VL as in any of the embodiments provided above and a light chain constant region comprising the amino acid sequence of any one of SEQ ID NOs: 36, 37, and 38.

In certain embodiments, the method is for the detection of ADAs against an anti-C5 antibody that competes for binding to C5 with an antibody comprising a VH and VL pair selected from: (a) a VH of SEQ ID NO: 01 and a VL of SEQ ID NO: 11; (b) a VH of SEQ ID NO: 22 and a VL of SEQ ID NO: 25; (c) a VH of SEQ ID NO: 21 and a VL of SEQ ID NO: 24; (d) a VH of SEQ ID NO: 05 and a VL of SEQ ID NO: 15; (e) a VH of SEQ ID NO: 04 and a VL of SEQ ID NO: 14; (f) a VH of SEQ ID NO: 06 and a VL of SEQ ID NO: 16; (g) a VH of SEQ ID NO: 02 and a VL of SEQ ID NO: 12; (h) a VH of SEQ ID NO: 03 and a VL of SEQ ID NO: 13; (i) a VH of SEQ ID NO: 09 and a VL of SEQ ID NO: 19; (j) a VH of SEQ ID NO: 7 and a VL of SEQ ID NO: 17; (k) a VH of SEQ ID NO: 8 and a VL of SEQ ID NO: 18; (l) a VH of SEQ ID NO: 23 and a VL of SEQ ID NO: 26; and (m) a VH of SEQ ID NO: 10 and a VL of SEQ ID NO: 20.

In certain embodiments, the method is for the detection of ADAs against an anti-C5 antibody that competes for binding C5 with an antibody comprising a VH and VL pair selected from: (a) a VH of SEQ ID NO: 22 and a VL of SEQ ID NO: 25; (b) a VH of SEQ ID NO: 21 and a VL of SEQ ID NO: 24; (c) a VH of SEQ ID NO: 05 and a VL of SEQ ID NO: 15; (d) a VH of SEQ ID NO: 04 and a VL of SEQ ID NO: 14; (e) a VH of SEQ ID NO: 06 and a VL of SEQ ID NO: 16; (f) a VH of SEQ ID NO: 02 and a VL of SEQ ID NO: 12; (g) a VH of SEQ ID NO: 03 and a VL of SEQ ID NO: 13; (h) a VH of SEQ ID NO: 09 and a VL of SEQ ID NO: 19; (i) a VH of SEQ ID NO: 07 and a VL of SEQ ID NO: 17; (j) a VH of SEQ ID NO: 8 and a VL of SEQ ID NO: 18; (k) a VH of SEQ ID NO: 23 and a VL of SEQ ID NO: 26.

The following Examples, Sequences and Figures are provided to aid the understanding of the present invention, the true scope of which is set forth in the appended claims. It is understood that modifications can be made in the procedures set forth without departing from the spirit of the invention.

EXAMPLES

Example 1

Assay with Saccharose and Brij

Figure 1:
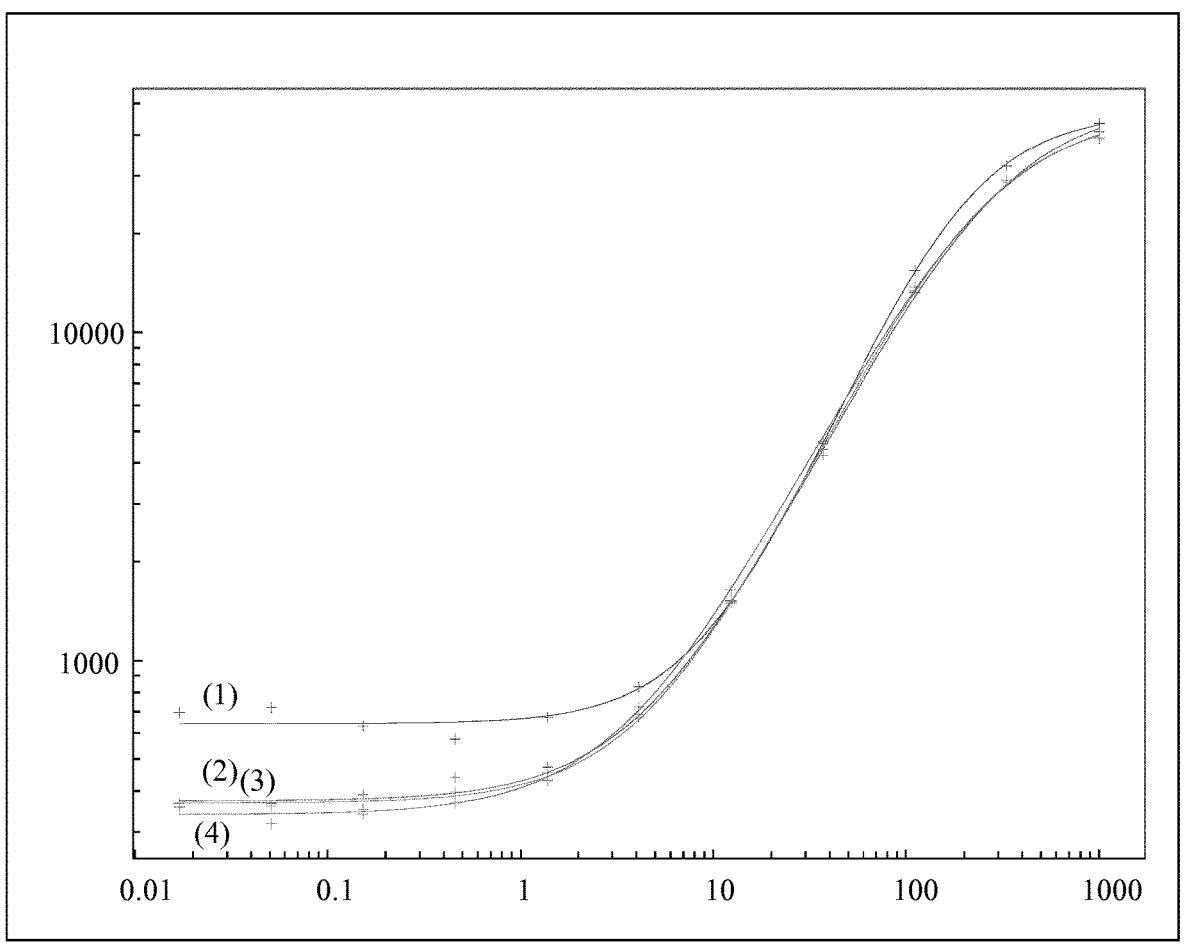
FIG. 1: Effect of different capture antibody as well as tracer antibody concentration ((1): 500 ng/ml each, (2): 1000 ng/ml each, (3): 1500 ng/ml each, (4): 2000 ng/ml each).
Figure 2:
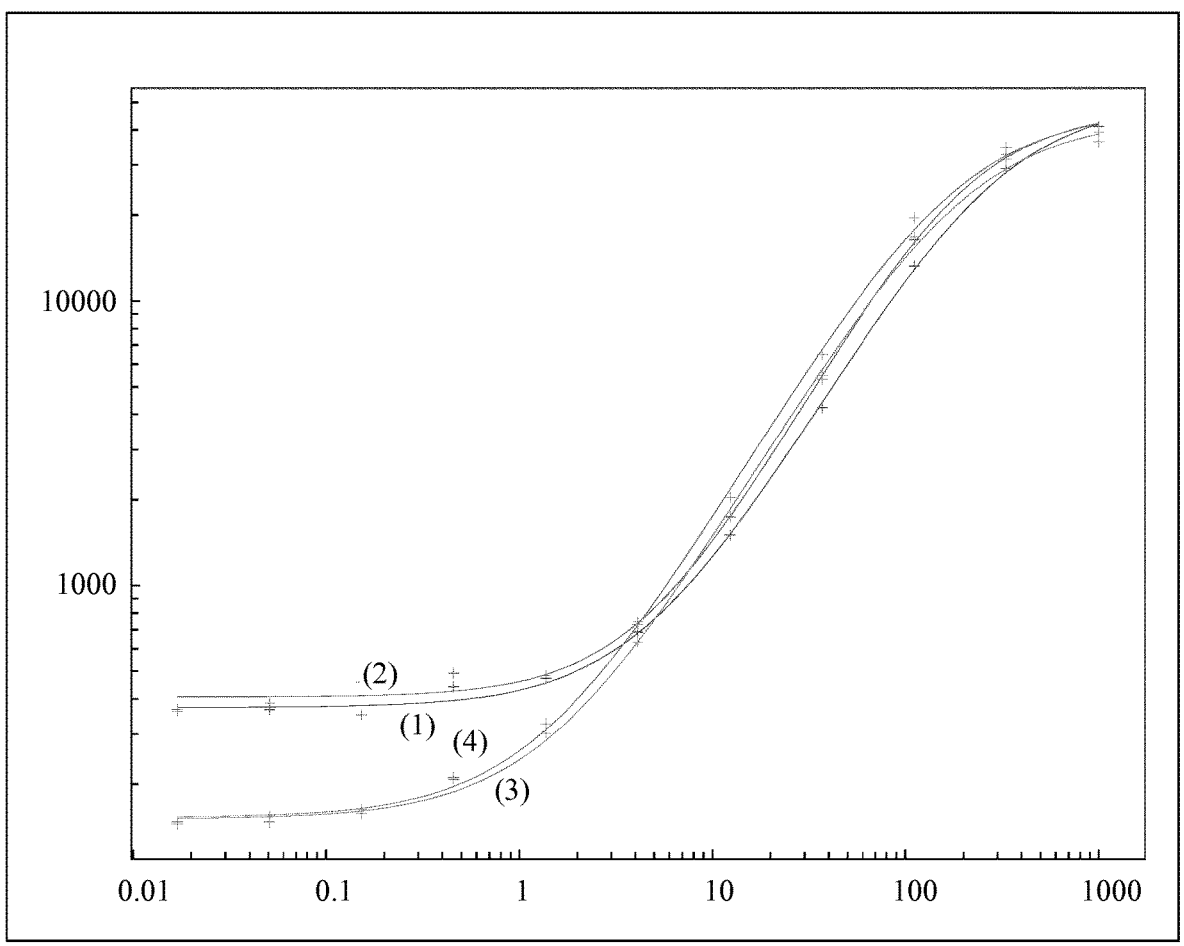
FIG. 2: Effect of different peroxidase concentrations ((1): 5 mU, (2): 10 mU, (3): 25 mU, (4): 50 mU at 1000 ng/ml capture and tracer antibody concentration).
Figure 3:
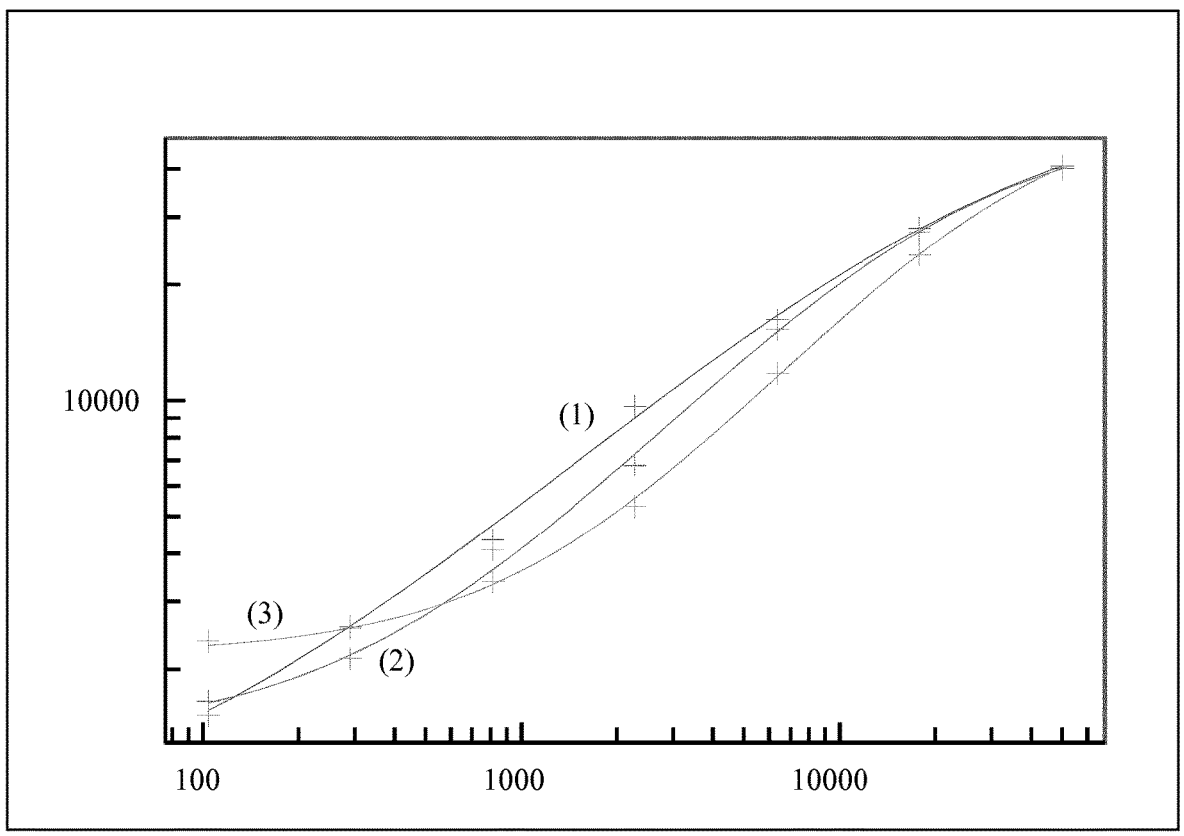
FIG. 3: Effect of Human and NHP serum ((1): human serum, (2): human plasma, (3): cynomolgus serum).
Figure 4:
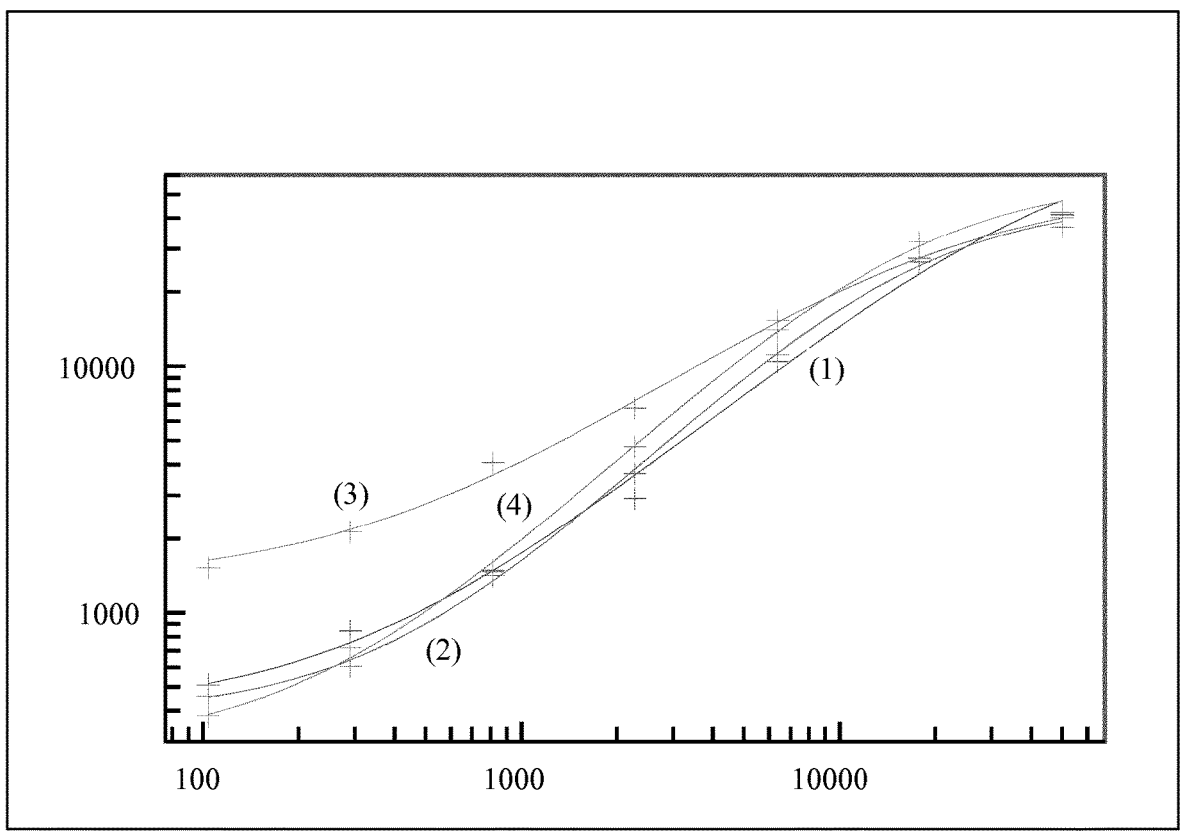
FIG. 4: Effect of horse (1), rabbit (2), C5 depleted human plasma (3) and buffer (4).
Figure 5:
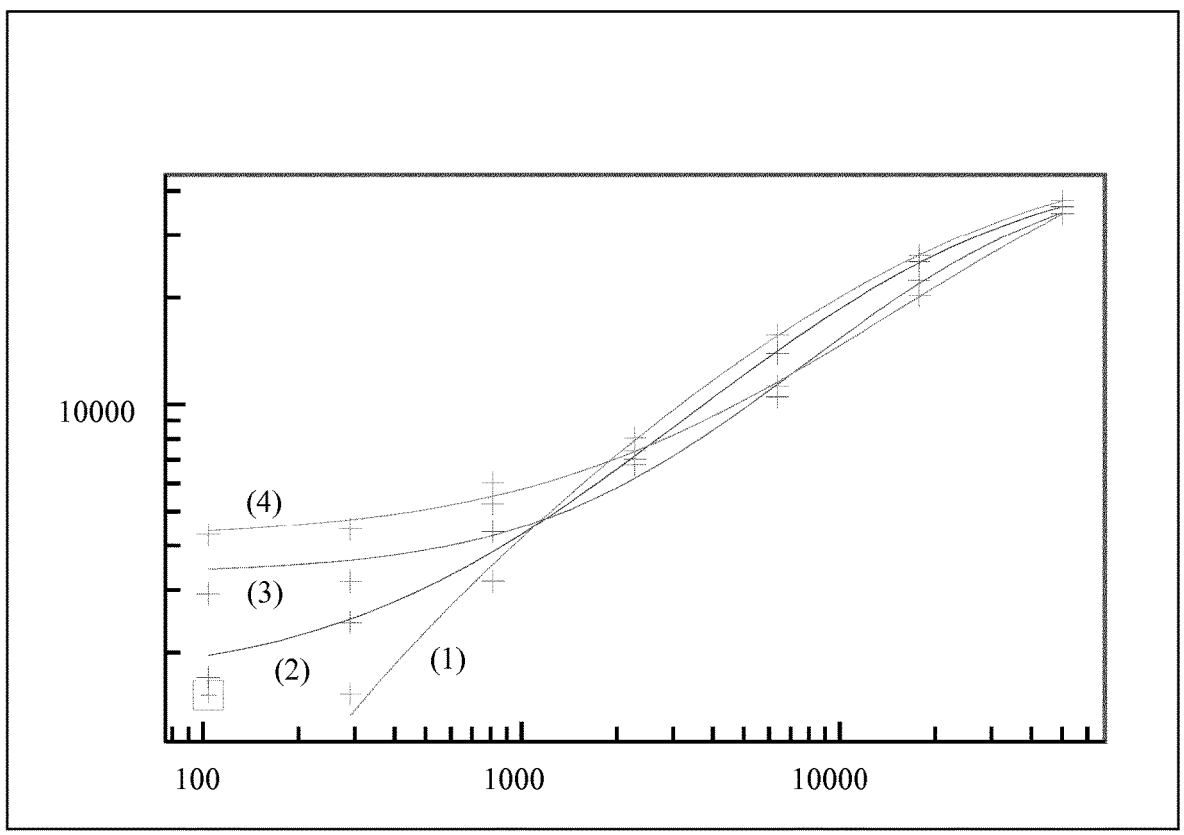
FIG. 5: The assay performance was impaired by the increase of horse serum and thereby horse C5 content in the sample (see FIG. 5) (1% human serum in 0% (1), 1% (2), 5% (3) or 10% (4) horse serum).
Figure 6:
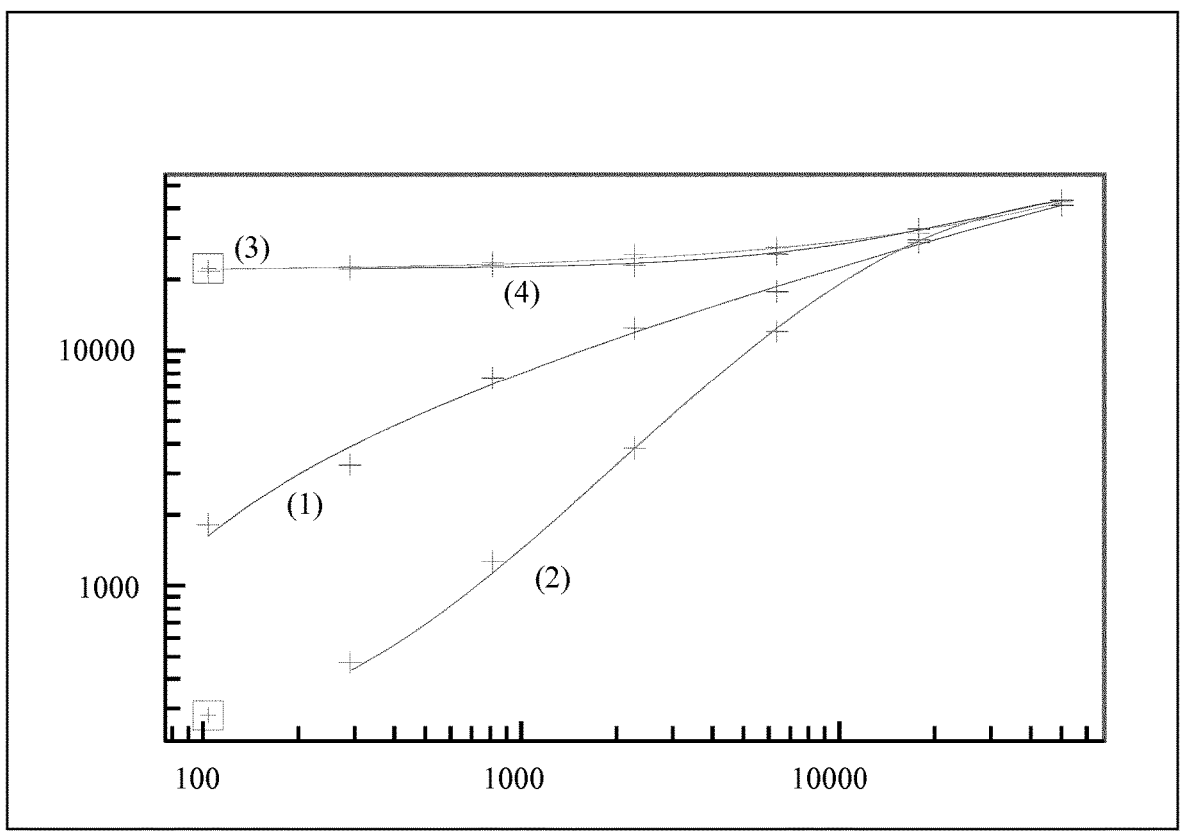
FIG. 6: Effect of human C5 on the assay (pAb+(1): human serum, (2): buffer+brij; (3): 500 ng/ml C5 in human serum, (4): 500 ng/ml C5 in buffer+brij).
Figure 7:
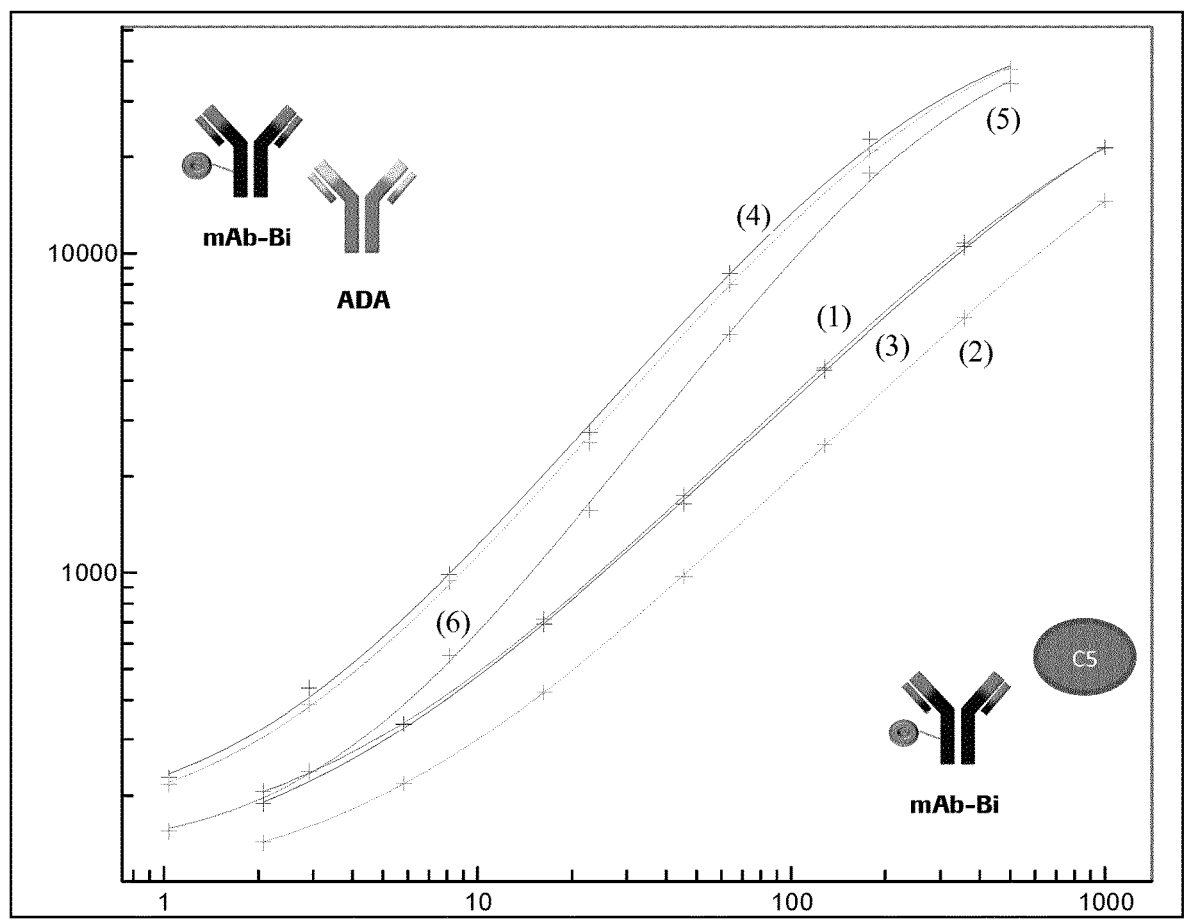
FIG. 7: Calibration of a bridging assay with C5 ((1): pH 7.4, (2): pH 5.5, (3): pH 8.0) and control pAb (anti-idiotypic antibody) ((4): pH 7.4, (5): pH 5.5, (6): pH 8.0).
Figure 8:
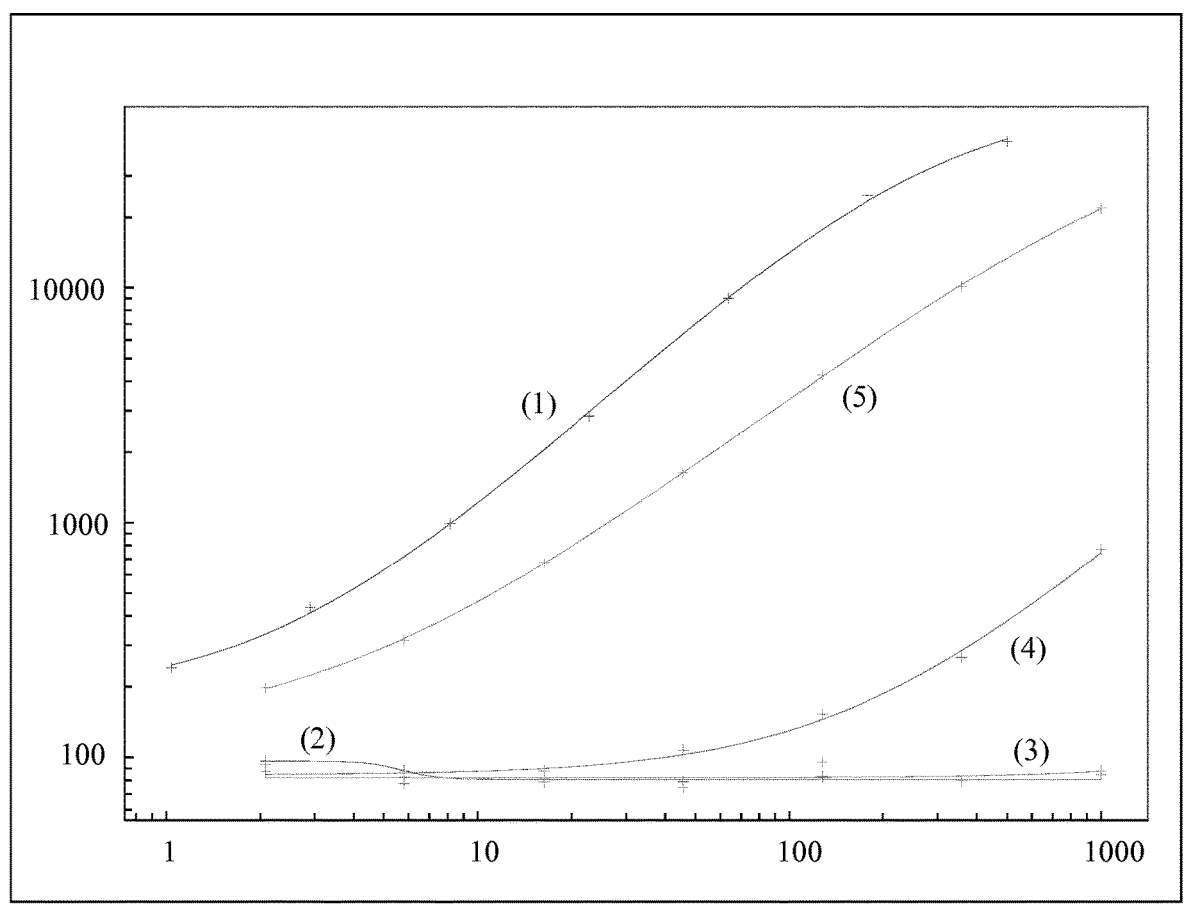
FIG. 8: Use of wash buffer pH 7.4 in the bridging assay (calibration with (1) pAb anti-idiotypic antibody and capture and tracer antibody, (2) C5 with no capture and no tracer antibody, (3) C5 with capture and no tracer antibody, (4) C5 with no capture but with tracer antibody, (5) C5 with capture and tracer antibody).
Figure 9:
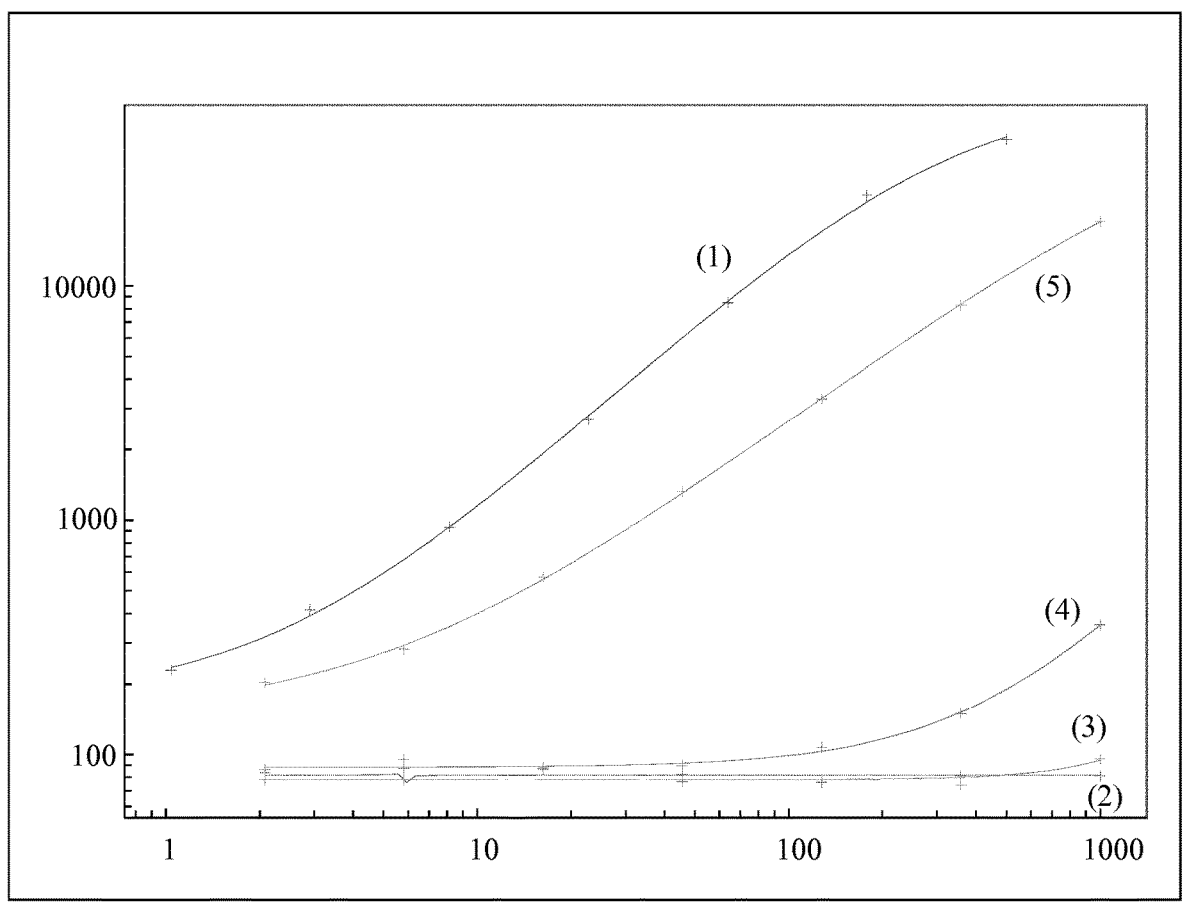
FIG. 9: Use of wash buffer pH 5.5 in the bridging assay (calibration with (1) pAb anti-idiotypic antibody and capture and tracer antibody, (2) C5 with no capture and no tracer antibody, (3) C5 with capture and no tracer antibody, (4) C5 with no capture but with tracer antibody, (5) C5 with capture and tracer antibody).
Figure 10:
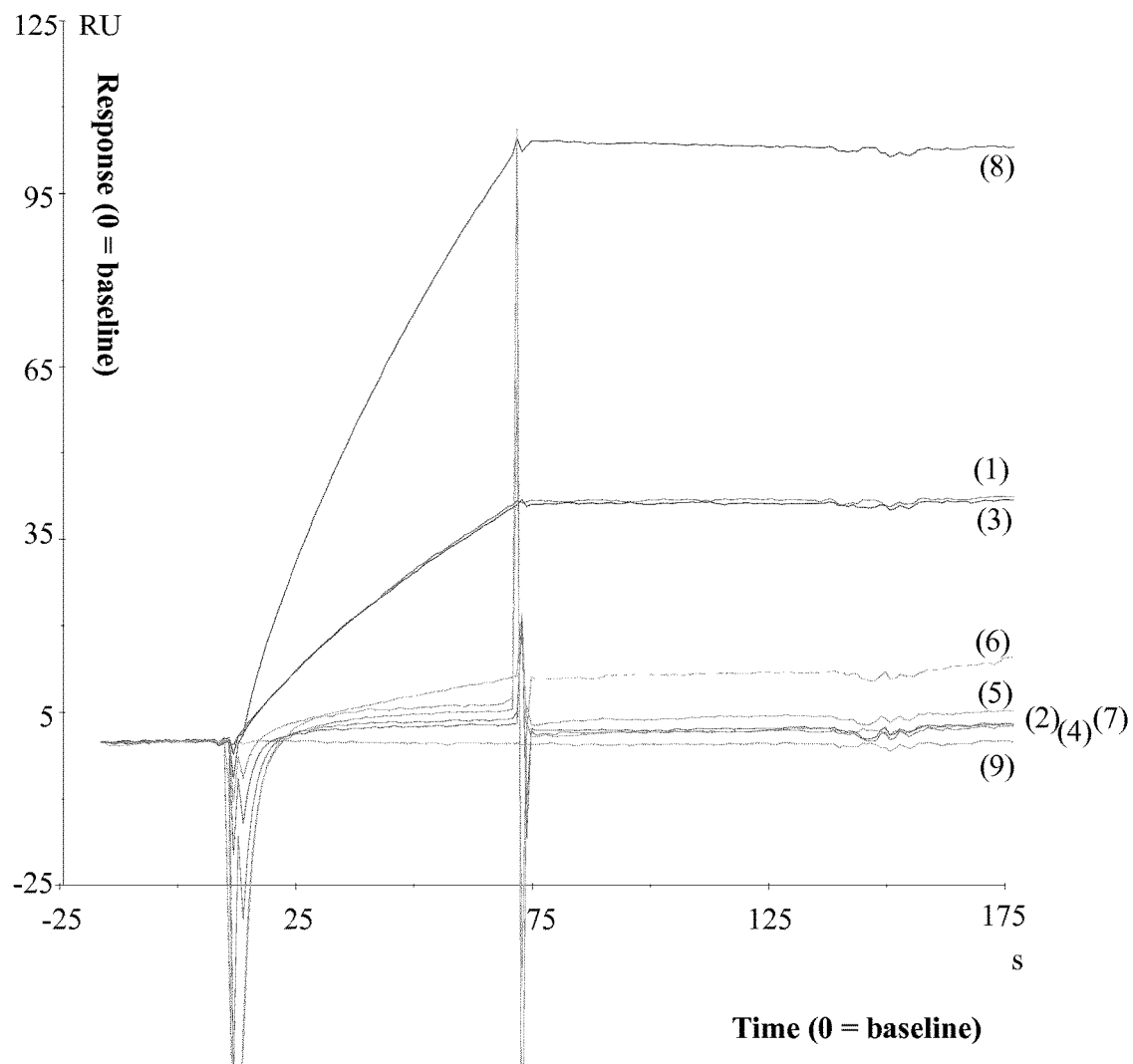
FIG. 10: Effect of drug to C5 ratio; adjusted SPR sensogram; (1): C5, (2): C5+pAb 100/100 nM, (3): C5+pAb 100/10 nM, (4): C5+pAb 100/250 nM, (5): C5+pAb 100/500 nM, (6): C5+pAb 100/50 nM, (7): mAb-C5, (8): pAb-anti-idiotypic-mAb C5, (9) buffer.
Figure 11:
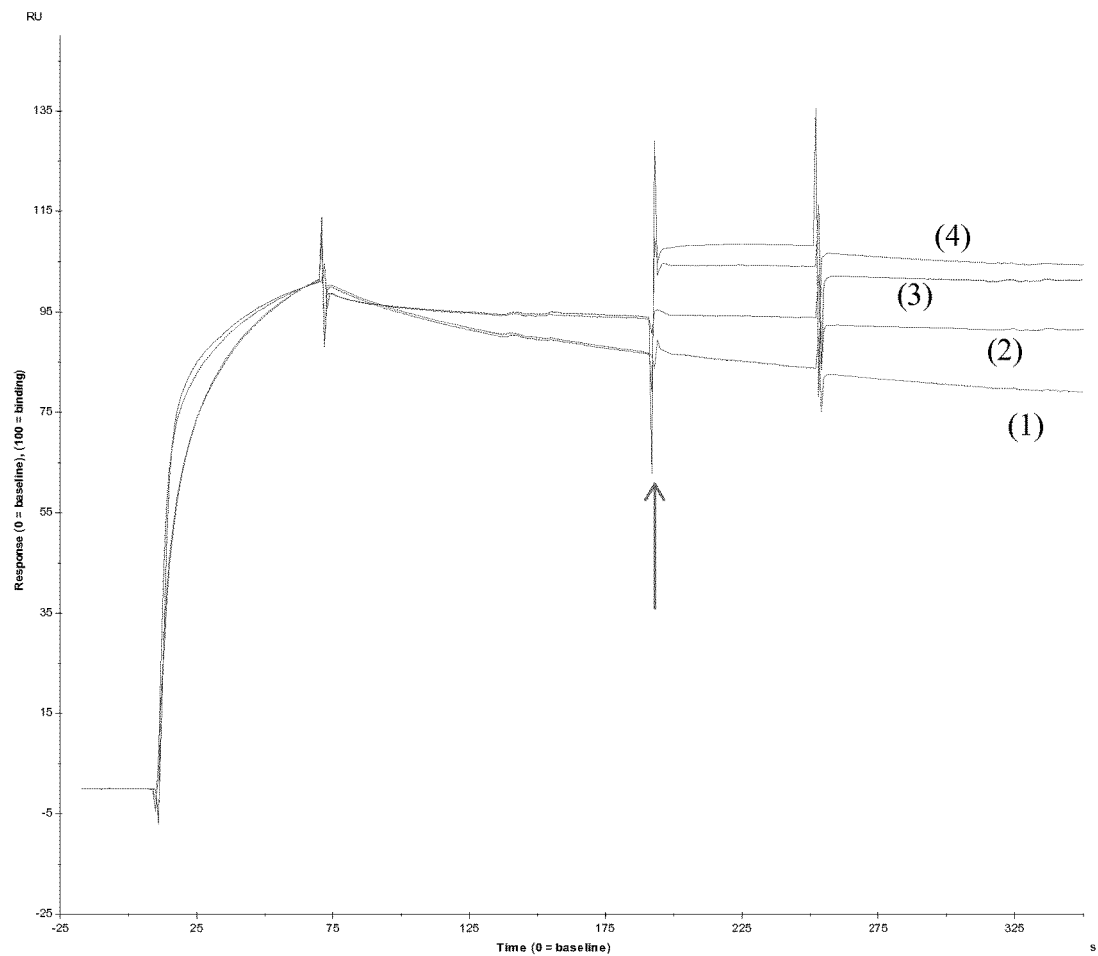
FIG. 11: Binding of pAb (green) and C5 (red) to a biotinylated drug coated surface followed by addition at time as indicated by arrow of buffer or tracer (1, 2)/digoxigenylated drug (3, 4).
Figure 12:
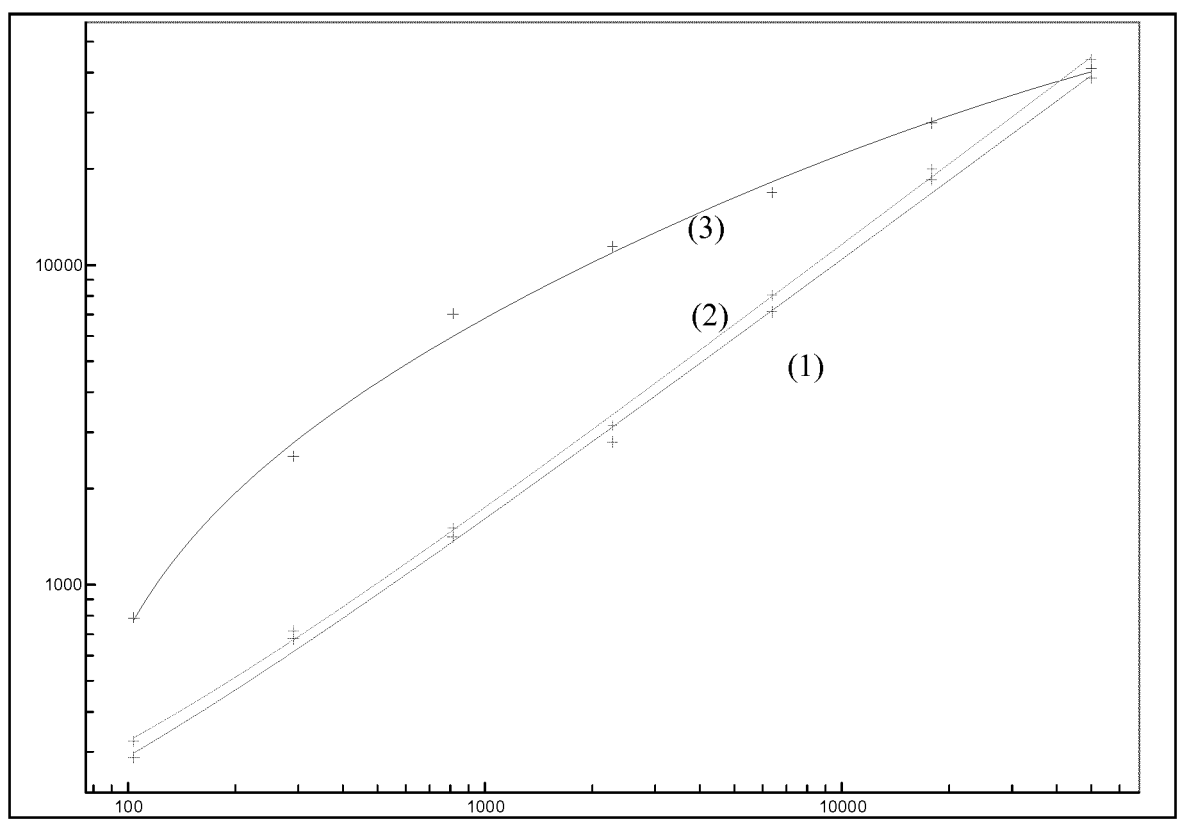
FIG. 12: Calibration of pAb in the bridging assay (1) without centrifugation (2) with centrifugation compared to a calibration without applying the acid incubation step (3).
Figure 13:
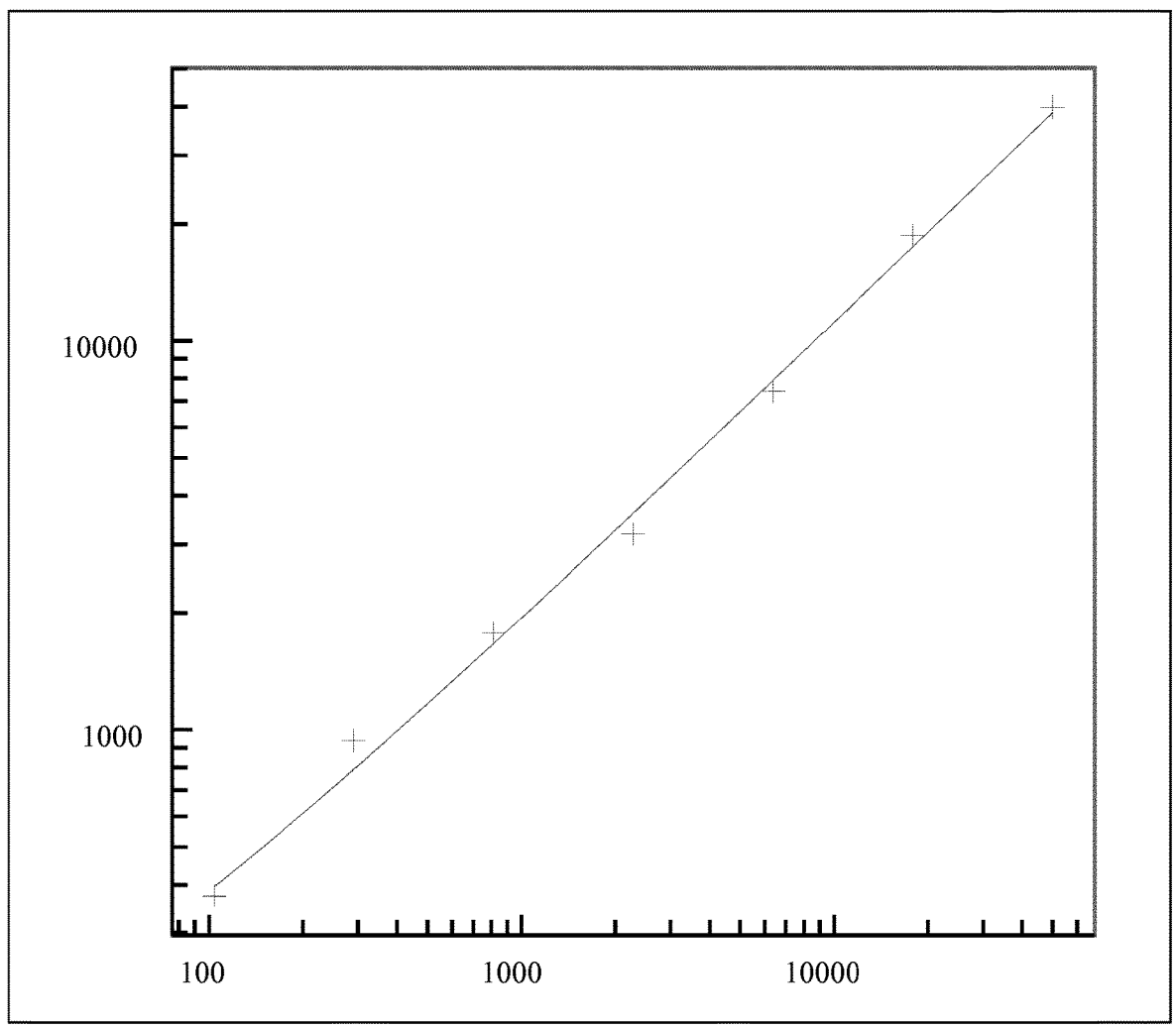
FIG. 13: Calibration with positive control, long incubation time, and pH 5.5 wash.
Figure 14:
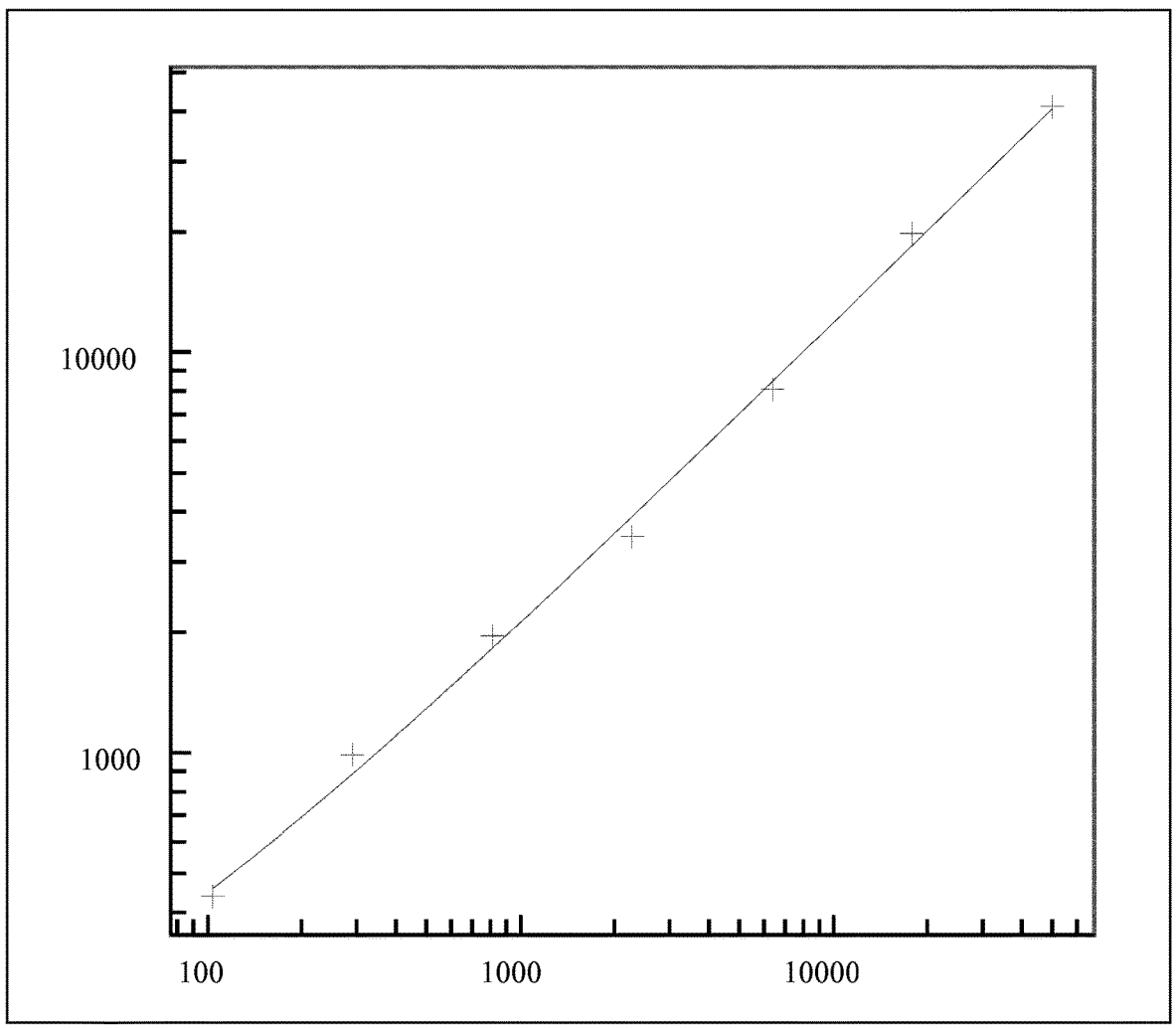
FIG. 14: Calibration with polyclonal antibody, long incubation time, and pH 7.4 wash.
Figure 15:
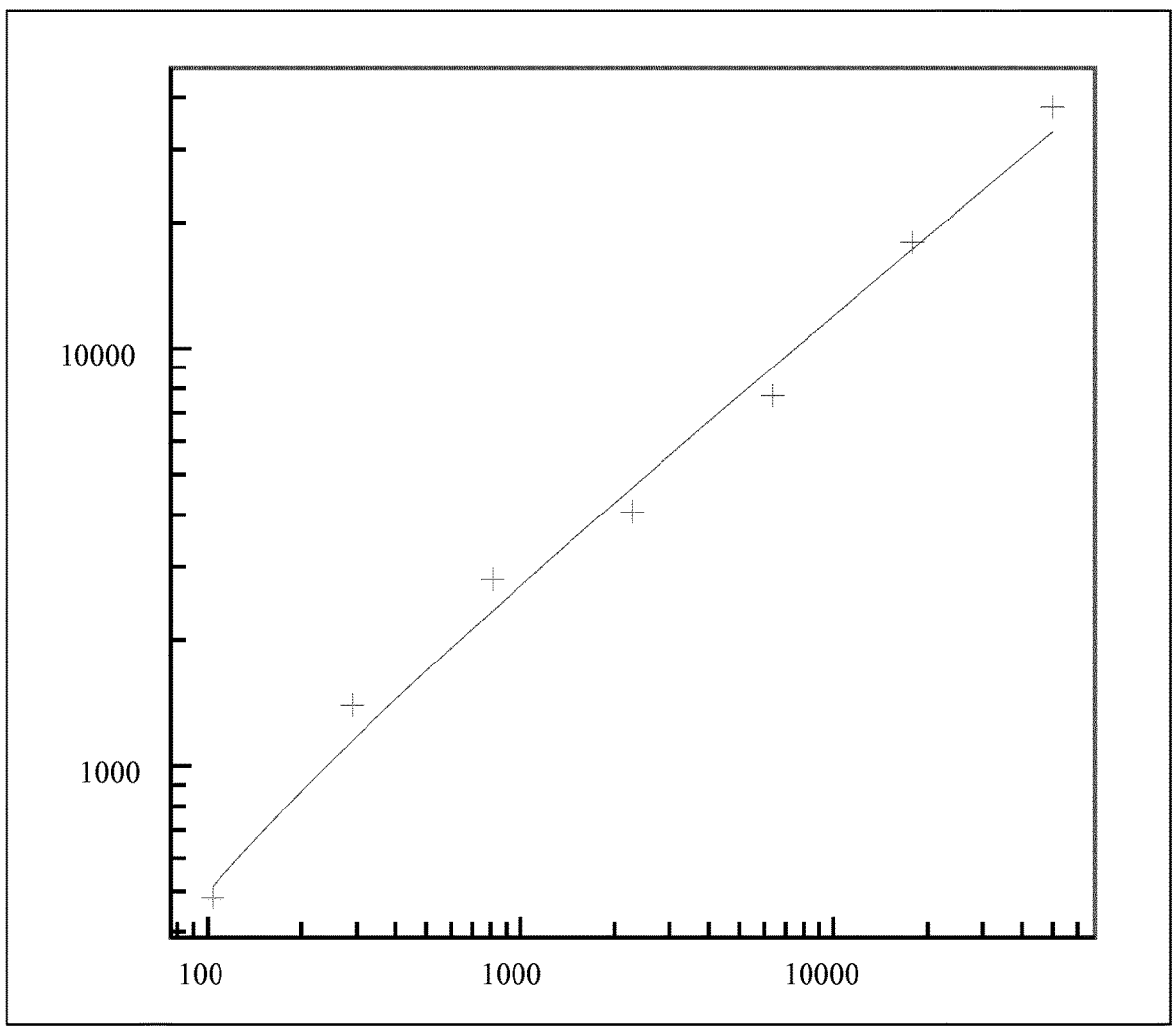
FIG. 15: Calibration with polyclonal antibody, short incubation time, and pH 5.5 Confidential wash.
Figure 16:
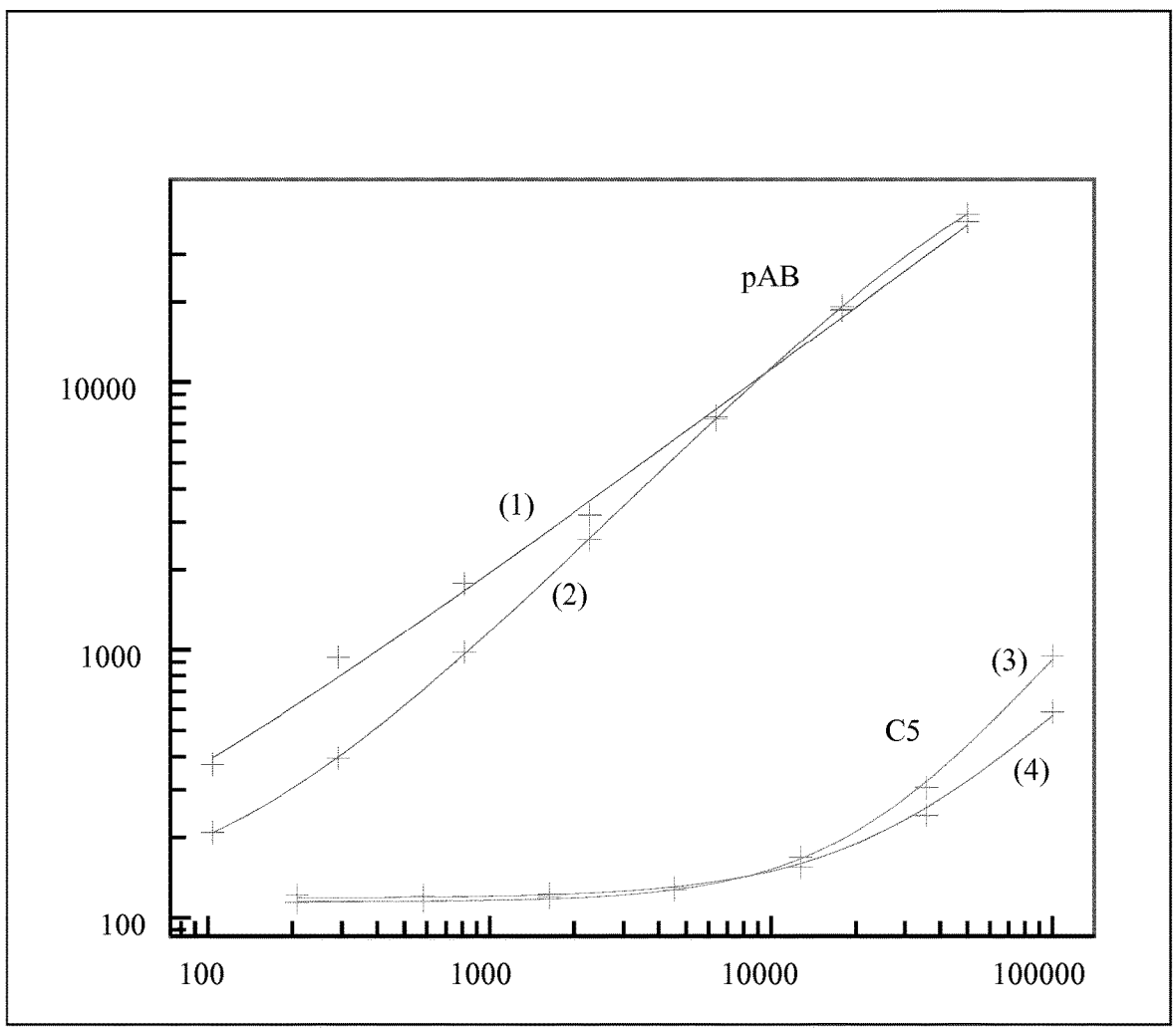
FIG. 16: Calibration with polyclonal antibody in the presence of serum (1), buffer (2), 2-hour incubation at pH 5, and pH 5.5 wash, calibration with C5 in the presence of serum (3), buffer (4), 2-hour incubation at pH 5, and pH 5.5 wash.
Figure 17:
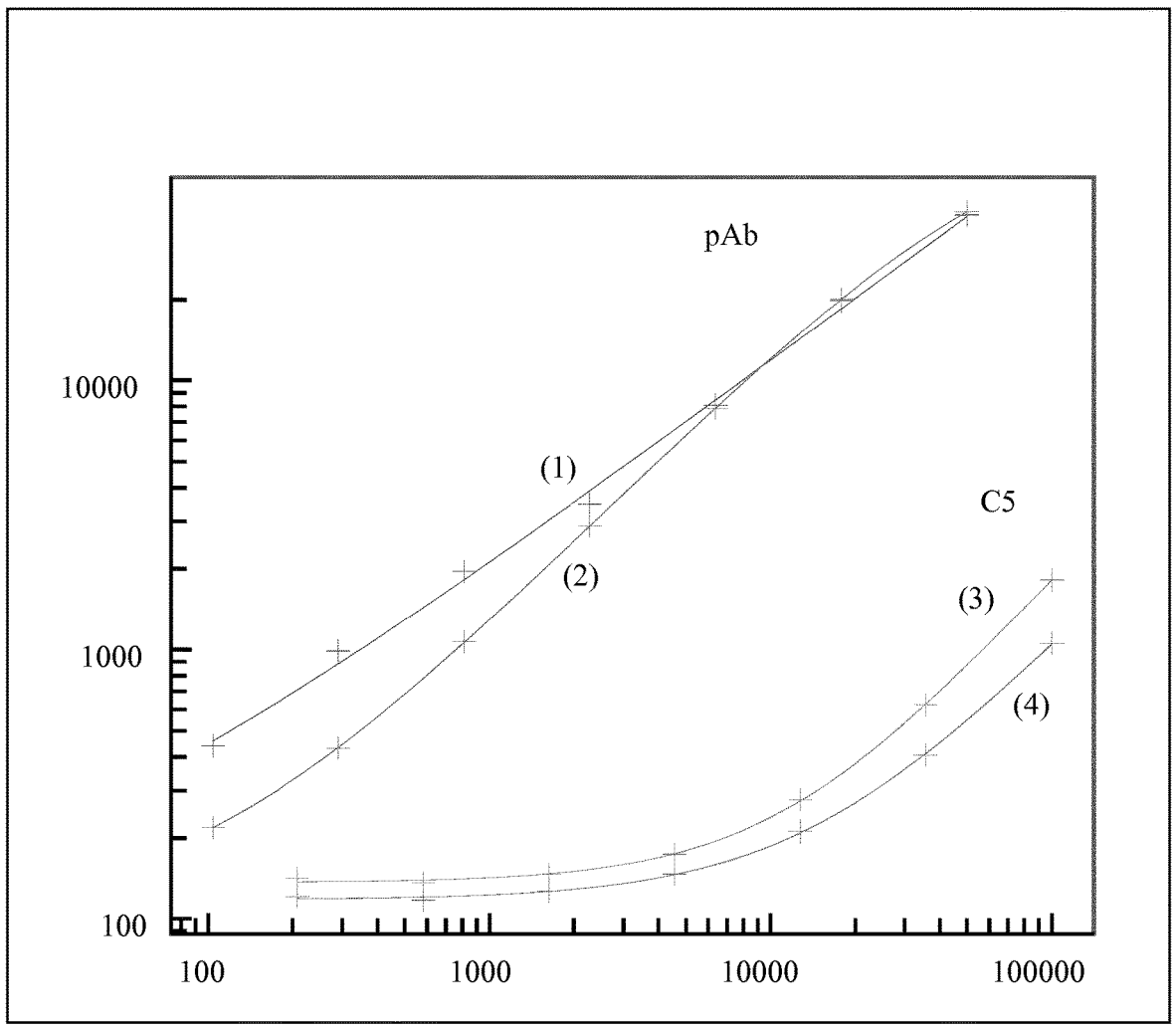
FIG. 17: Calibration with polyclonal antibody in the presence of serum (1), buffer (2), 2-hour incubation at pH 5, and pH 7.4 wash, calibration with C5 in the presence of serum (3), buffer (4), 2-hour incubation at pH 5, and pH 7.4 wash.
Figure 18:
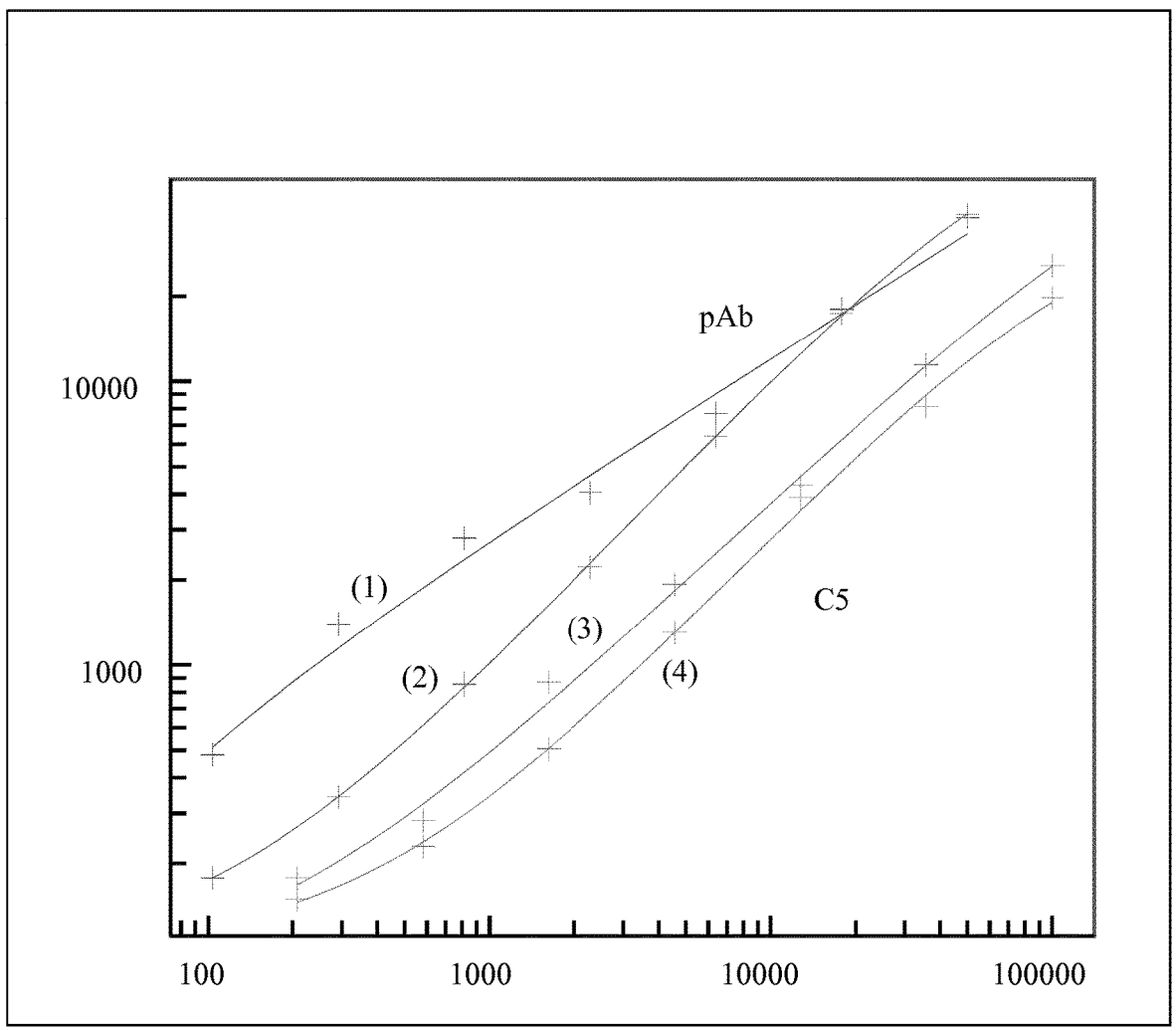
FIG. 18: Calibration with polyclonal antibody in the presence of serum (1), buffer (2), 0.5-hour incubation at pH 2, and pH 5.5 wash, calibration with C5 in the presence of serum (3), buffer (4), 0.5-hour incubation at pH 2, and pH 5.5 wash.

Biotinylated and digoxigenylated drug was incubated with 30 individual sera samples. For functionally testing of the used reagents (control) serum samples (pooled serum) were prepared with different concentrations of an artificial positive control standard, incubated and processed as the individual serum samples. The labelled drug concentrations were kept constant at 1000 ng/mL each. The final serum concertation in the assay was 1%. Formed immune complexes were transferred to a white Streptavidin (SA)-coated microtiter plate and incubated for 1 hour to immobilize the complexes via the biotin-labeled capture reagent. Following aspiration of the supernatant unbound substances were removed by repeated washings. Immobilized complexes were incubated with an anti-digoxigenin antibody conjugated to horseradish peroxidase (anti-digoxigenin-POD (poly)). Each step was performed with the same buffer by using either a PBS buffer with 6.5% saccharose or Roche universal buffer for ELISA with Brij 35 at a concentration of 0.5%. Finally, formed immobilized immune complexes were visualized by addition of oxidized HPPA solution, a fluorescent POD substrate. The emission was photometrically determined (Excitation at 320 nm, emission at 405 nm wave length) and set in relation to the positive control concentration in the sample. The CV of the individual serum samples are 29% (saccharose buffer assay) and 181% (Roche universal buffer with Brij).

Example 2

Assay with Acid Incubation Step

Individual serum samples (N=30) and artificial positive control samples were incubated for 2 hours with 10 mM acetate buffer pH 5.0. Thereafter the samples were incubated for 5 min with 0.1 M glycine hydrochloride pH 2.0. The acidified samples were mixed with biotinylated capture antibody and digoxigenylated detection antibody, neutralized with 0.5 M TRIS buffer pH 8.5 and incubated for 30 min at RT and 450 rpm on a microtiter plate shaker. The final serum assay concentration was 1%. Formed immune complexes were transferred to a Streptavidin (SA)-coated microtiter plate and incubated for 1 hour to immobilize the immune complexes via the biotin-labeled capture antibody. Following aspiration of the supernatant unbound substances were removed by repeated washings. Immobilized immune complexes were incubated with an anti-digoxigenin Fab fragment conjugated to horseradish peroxidase (Anti-Dig-POD). Formed immobilized immune complexes were visualized by addition of oxidized HPPA solution, a fluorescent POD substrate. The emission was photometrically determined (Excitation at 320 nm, emission at 405 nm wave length) and set in relation to the artificial positive control concentration in the serum sample. The artificial positive control provides a blank to noise ratio at 100 ng/mL in 100% serum of >3. The CV of the individual serum samples (N=30) is 7%.

Example 3

Assay with Low Serum Contend and No Acid Dissociation

Biotinylated and digoxigenylated drug was incubated with 32 individual sera at a final serum concentration of 1% and 0.1%. For functionally testing of the used reagents (control) serum samples (pooled serum) were prepared with different concentrations of an artificial positive control standard, incubated and processed as the individual serum samples. The labelled drug concentrations were kept constant at 1000 ng/mL each. Formed immune complexes were transferred to a white Streptavidin (SA)-coated microtiter plate and incubated for 1 hour to immobilize the complexes via the biotin-labeled capture reagent. Following aspiration of the supernatant unbound substances were removed by repeated washings. Immobilized complexes were incubated with an anti-digoxigenin antibody conjugated to horseradish peroxidase (anti-digoxigenin-POD (poly)). Finally, formed immobilized immune complexes were visualized by addition of oxidized HPPA solution, a fluorescent POD substrate. The emission was photometrically determined (Excitation at 320 nm, emission at 405 nm wave length) and was proportional to the positive control concentration in the sample. The artificial positive control indicates an assay sensitivity of ~100 ng/mL in 100% serum for the 1 and 0.1% assay. The CV of the individual serum samples are 74% (0.1% serum assay) and 65% (1% serum assay).

The invention claimed is:

1. An immunoassay for quantifying the amount of anti-drug antibody, which anti-drug antibody can specifically bind to a drug antibody, which drug antibody can specifically bind to a therapeutic target, in a serum or plasma sample with reduced target interference comprising the following steps:
   a) incubating an immobilized capture antibody with a serum or plasma sample comprising drug, target and anti-drug antibody, to form a capture antibody-anti-drug antibody complex,
   b) washing the complex formed in step a) with a buffer comprising a sugar and a detergent, which has a pH value of about the pI of the target,
   c) incubating for 12 to 24 hours the washed complex of step b) with a tracer antibody conjugated to a label to form a capture antibody-anti-drug antibody-tracer antibody complex,
   d) quantifying the amount of anti-drug antibody by determining the label in the complex formed in step c).

2. The immunoassay according to claim 1, wherein the tracer antibody and the capture antibody is the drug antibody.

3. The immunoassay according to claim 1, wherein the immunoassay comprises a capture antibody, a tracer antibody and a detection antibody, wherein the capture antibody is the drug conjugated to a first member of a binding pair, the tracer antibody is the drug antibody conjugated to a detectable label and the detection antibody is an antibody specifically binding to the detectable label conjugated to an enzyme.

4. The immunoassay according to claim 1, wherein the capture antibody and/or the tracer antibody is independently of each other selected from the group consisting of complete/full length drug antibody, F(ab')2, Fab and scFv.

5. The immunoassay according to claim 1, wherein the sugar is a monosaccharide, a disaccharide or a trisaccharide.

6. The immunoassay according to claim 1, wherein the sugar is selected from the group of disaccharides consisting of saccharose, lactose, maltose, iso-maltose, and trehalose.

7. The immunoassay according to claim 1, wherein the sugar has a concentration of about 6.5 wt-%.

8. The immunoassay according to claim 1, wherein the detergent is a non-ionic detergent.

9. The immunoassay according to claim 1, wherein the detergent is selected from the group of detergents consisting of polyalkylene glycol ether, polyoxyethylene sorbitane monoesters, octylphenol ethoxylate, octyl-beta-glycoside, n-fatty acid-N-methyl-D-glucamide, and N,N'-bis-(3-D-gluconamidopropyl) cholamide.

10. The immunoassay according to claim 1, the incubation is for 14 to 20 hours or for 15 to 17 hours.

11. The immunoassay according to claim 3, wherein the first member of the binding pair is selected from the group consisting of hapten, antigen and hormone.

12. The immunoassay according to claim 3, wherein the binding pair is selected from the group consisting of biotin/(strept)avidin, theophylline/anti-theophylline antibody, 5-bromo-desoxy-uridine/anti-5-bromo-deoxy-uridine antibody, digoxigenin/anti-digoxygenin antibody, and helicar/anti-helical antibody.

13. The immunoassay according to claim 1, wherein the drug is an anti-C5 antibody and the target is human C5.

14. The immunoassay according to claim 1, wherein the sugar is saccharose, the detergent is polyethylene glycol dodecyl ether, the drug is an anti-C5 antibody, the target is human C5 and the buffer has a pH value of about 5.5.

15. An immunoassay for quantifying the amount of anti-drug antibody, which anti-drug antibody can specifically bind to a drug antibody, which drug antibody can specifically bind to a therapeutic target, in a serum or plasma sample with reduced target interference comprising the following steps:
   a) incubating the serum or plasma sample at a pH value that is about the pI value of the target, and optionally removing formed precipitate after the incubation, wherein the sample is from an animal to which the drug had been administered prior to obtaining the sample,
   b) incubating the serum or plasma sample obtained in step a) at a pH value of about 2, and optionally centrifuging the incubated sample to remove formed precipitate,
   c) adjusting the pH value to about 7.4, adding capture antibody conjugated to a first member of a binding pair and tracer antibody conjugated to a detectable label to the serum or plasma sample obtained in step b) and incubating the mixture to form a capture antibody-anti-drug antibody-tracer antibody-complex,
   d) quantifying the complex formed in step c) and thereby quantifying the amount of anti-drug antibody in the serum or plasma sample.

16. The immunoassay according to claim 15, wherein the step of quantifying the capture antibody-anti-drug antibody-tracer antibody-complex (step d)) comprises the steps of
   d1) incubating the serum or plasma sample obtained in step c) with the second member of the binding pair conjugated to a solid surface to capture the capture antibody-anti-drug antibody-tracer antibody-complex, and optionally washing the surface,
   d2) quantifying the amount of anti-drug antibody by determining the detectable label in the complex formed in step d1).

17. The immunoassay according to claim 15, wherein the incubation at about the pI value of the target is at a pH value in the range of 0.5 pH units below the pI of the target to 0.5 pH units above the pI value of the target.

18. The immunoassay according to claim 15, wherein the incubating in step a) is with agitation.

19. The immunoassay according to claim 15, wherein the incubating in step a) is for 1.5 to 2.5 hours.

20. The immunoassay according to claim 15, wherein the incubating in step b) is for about 5 min.

21. The immunoassay according to claim 15, wherein the tracer antibody and the capture antibody is the drug antibody.

22. The immunoassay according to claim 15, wherein the immunoassay comprises a capture antibody, a tracer antibody and a detection antibody, wherein the capture antibody is the drug conjugated to a first member of a binding pair, the tracer antibody is the drug antibody conjugated to a detectable label and the detection antibody, which is further conjugated to an enzyme, is an antibody specifically binding to the detectable label.

23. The immunoassay according to claim 15, wherein the capture antibody and/or the tracer antibody is independently of each other selected from the group consisting of complete/full length drug antibody, F(ab')2, Fab and scFv.

24. The immunoassay according to claim 15, wherein the first member of the binding pair is selected from the group consisting of hapten, antigen and hormone.

25. The immunoassay according to claim 15, wherein the binding pair is selected from the group consisting of biotin/(strept)avidin, theophylline/anti-theophylline antibody, 5-bromo-desoxy-uridine/anti-5-bromo-deoxy-uridine antibody, digoxigenin/anti-digoxygenin antibody, and helicar/anti-helical antibody.

26. The immunoassay according to claim 15, wherein the drug is an anti-C5 antibody and the target is human C5.

27. The immunoassay according to claim 15, wherein the immunoassay for quantifying the amount of anti-drug antibody, which anti-drug antibody can specifically bind to a drug antibody, which drug antibody is an anti-C5 antibody that can specifically bind to human C5, in a serum or plasma sample comprises the following steps:
   a) incubating the serum or plasma sample at a pH value in the range of 4.7 to 5.5 for 1.5 to 2.5 hours, and optionally removing formed precipitate after the incubation,
   b) incubating the serum or plasma sample obtained in step a) at a pH value of about 2 for about 5 minutes, and optionally centrifuging the incubated sample to remove formed precipitate,
   c) adjusting the pH value to about 7.4, adding capture drug antibody conjugated to biotin and tracer drug antibody conjugated to digoxigenin to the serum or plasma sample obtained in step b) and incubating the mixture to form a capture antibody-anti-drug antibody-tracer antibody-complex,
   d) incubating the serum or plasma sample obtained in step c) with (strept)avidin conjugated to a solid surface to capture the capture antibody-anti-drug antibody-tracer antibody-complex, and optionally washing the surface,
   e) detecting anti-drug antibody by determining the digoxigenin in the complex formed in step d) by incubating with an anti-digoxigenin antibody conjugated to horseradish peroxidase and thereafter incubation with 3-(4-hydroxyphenyl) propionic acid (HPPA) or 3,3',5,5'-tetramethyl-benzidine (TMB), and thereby detecting anti-drug antibody in the serum or plasma sample (correlating the formed complex to the amount of the anti-drug antibody (ADA) in the sample)).

28. The immunoassay according to claim 15, wherein the sample is from a patient in need of a treatment with the drug to which the drug had been administered prior to obtaining the sample.

29. The immunoassay according to claim 15, wherein the complexes are non-covalent complexes.

30. The immunoassay according to claim 15, wherein the immunoassay comprises the following steps:
   a) immobilizing the capture antibody on a solid surface, and optionally washing the surface after the immobilization step to remove unbound and non-specifically bound capture antibody,
   b) incubating the immobilized capture antibody of step a) with a serum or plasma containing sample, which optionally has been diluted to have a concentration of the anti-drug antibody within the detection range of the immunoassay, to form a capture antibody-anti-drug antibody-complex, and optionally washing the surface after the incubation step to remove unbound and non-specifically bound sample,
   c) incubating the capture antibody-anti-drug antibody-complex of step b) with a labelled tracer antibody to form a capture antibody-anti-drug antibody-tracer antibody complex, and optionally washing the surface after the incubation step to remove unbound and non-specifically bound tracer antibody,
   d) incubating the capture antibody-anti-drug antibody-tracer antibody complex of step c) with an antibody specifically binding to the label of the tracer antibody conjugated to an enzyme to form a capture antibody-anti-drug antibody-tracer antibody-detection antibody complex, and optionally washing the surface after the incubation step to remove unbound and non-specifically bound detection antibody,
   e) incubating the capture antibody-anti-drug antibody-tracer antibody-detection antibody complex of step d) with a colorless substrate of the enzyme that upon action of the enzyme on the substrate is converted to a colored reaction product and determining the optical density after a predefined period of time,
   f) correlating the optical density determined in step e) with a calibration curve and thereby determining the amount of anti-drug antibody in the sample.

31. The immunoassay according to claim 15, wherein said animal is a human.

32. The immunoassay according to claim 15, wherein the pH value in step a) is in the range of pH 4.7 to pH 5.5.

33. The immunoassay according to claim 27, wherein the incubating in step d) is for about 60 min.

* * * * *

SEQUENCE LISTING

<160> NUMBER OF SEQ ID NOS: 116

<210> SEQ ID NO 1
<211> LENGTH: 121
<212> TYPE: PRT
<213> ORGANISM: Artificial Sequence
<220> FEATURE:
<223> OTHER INFORMATION: CFA0305 VH

<400> SEQUENCE: 1

```
Gln Ser Leu Glu Glu Ser Gly Gly Asp Leu Val Lys Pro Gly Ala Ser
1               5                   10                  15

Leu Ala Val Thr Cys Thr Ala Ser Gly Phe Ser Ser Ser Ser Ser Tyr
            20                  25                  30

Tyr Met Cys Trp Val Arg Gln Ala Pro Gly Lys Gly Leu Glu Trp Ile
        35                  40                  45

Gly Cys Ile Tyr Thr Gly Ser Gly Ala Thr Tyr Tyr Ala Ser Trp Ala
    50                  55                  60

Lys Gly Arg Phe Thr Ile Ser Lys Thr Ser Thr Thr Val Thr Leu
65                  70                  75                  80

Gln Met Thr Ser Leu Thr Val Ala Asp Thr Ala Thr Tyr Phe Cys Ala
                85                  90                  95

Ser Asp Gly Gly Tyr Val Thr Pro Thr His Ala Met Tyr Leu Trp Gly
            100                 105                 110

Pro Gly Thr Leu Val Thr Val Ser Ser
        115                 120
```

<210> SEQ ID NO 2
<211> LENGTH: 117
<212> TYPE: PRT
<213> ORGANISM: Artificial Sequence
<220> FEATURE:
<223> OTHER INFORMATION: CFA0307 VH

<400> SEQUENCE: 2

```
Gln Ser Leu Glu Glu Ser Gly Gly Gly Leu Val Lys Pro Gly Ala Ser
1               5                   10                  15

Leu Thr Leu Thr Cys Lys Ala Ser Gly Ile Asp Phe Ser Asn Phe Tyr
            20                  25                  30

Tyr Ile Cys Trp Val Arg Gln Ala Pro Gly Lys Gly Leu Asp Leu Ile
        35                  40                  45

Ala Cys Ile Tyr Thr Val Ser Gly Tyr Thr Tyr Tyr Ala Ser Trp Ala
    50                  55                  60

Lys Gly Arg Leu Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Leu His Ala Gly Ile Thr Asn Leu Trp Gly Pro Gly Thr Leu
            100                 105                 110

Val Thr Val Ser Ser
        115
```

<210> SEQ ID NO 3
<211> LENGTH: 122
<212> TYPE: PRT
<213> ORGANISM: Artificial Sequence
<220> FEATURE:
<223> OTHER INFORMATION: CFA0366 VH

<400> SEQUENCE: 3

```
Gln Ser Leu Glu Glu Ser Gly Gly Asp Leu Val Lys Pro Gly Ala Ser
1               5                   10                  15

Leu Ser Leu Thr Cys Thr Ala Ala Gly Leu Asp Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Ala Gly Ser Ser Gly Ile Ile Tyr Tyr Ala Asn Trp
    50                  55                  60

Ala Lys Gly Arg Phe Thr Ile Ser Arg Pro Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Thr Tyr Pro Thr Tyr Gly Asp Gly Gly His Ala Phe Asn Leu Trp
                100                 105                 110

Gly Pro Gly Thr Leu Val Thr Val Ser Ser
            115                 120

<210> SEQ ID NO 4
<211> LENGTH: 117
<212> TYPE: PRT
<213> ORGANISM: Artificial Sequence
<220> FEATURE:
<223> OTHER INFORMATION: CFA0501 VH

<400> SEQUENCE: 4

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Met Ile Tyr Gly Ser Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gln
                85                  90                  95

Ile Tyr Ser Gly Asp Asn Asn Asp Asn Phe Trp Gly Pro Gly Thr Leu
                100                 105                 110

Val Thr Val Ser Ser
            115

<210> SEQ ID NO 5
<211> LENGTH: 117
<212> TYPE: PRT
<213> ORGANISM: Artificial Sequence
<220> FEATURE:
<223> OTHER INFORMATION: CFA0538 VH

<400> SEQUENCE: 5

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Met Ile Tyr Gly Ser Gly Ala Thr Tyr Tyr Ala Ser Trp Ala Lys Gly
```

```
                    50                  55                  60
Arg Phe Thr Ile Ser Lys Thr Ser Ser Thr Thr Val Asp Leu Lys Met
 65                  70                  75                  80

Thr Ser Leu Thr Thr Glu Asp Thr Ala Thr Tyr Phe Cys Ala Arg Gln
                     85                  90                  95

Ile Tyr Ser Gly Asp Asn Asn Asp Asn Phe Trp Gly Pro Gly Thr Leu
                100                 105                 110

Val Thr Val Ser Ser
            115

<210> SEQ ID NO 6
<211> LENGTH: 117
<212> TYPE: PRT
<213> ORGANISM: Artificial Sequence
<220> FEATURE:
<223> OTHER INFORMATION: CFA0599 VH

<400> SEQUENCE: 6

Gln Ser Val Glu Glu Ser Gly Gly Arg Leu Val Thr Pro Gly Thr Pro
 1               5                  10                  15

Leu Thr Leu Thr Cys Thr Val Ser Gly Leu Ser Leu Ser Asp Asn Thr
                20                  25                  30

Met Thr Trp Val Arg Gln Ala Pro Gly Lys Gly Leu Glu Trp Ile Gly
            35                  40                  45

Ile Ile Ser Phe Gly Gly Asp Ala Tyr Tyr Ala Ser Trp Ala Lys Gly
        50                  55                  60

Arg Phe Pro Ile Ser Lys Thr Ser Thr Thr Val Asp Leu Arg Ile Thr
 65                  70                  75                  80

Ser Pro Thr Thr Glu Asp Thr Ala Thr Tyr Phe Cys Ala Arg Val Gly
                     85                  90                  95

Ala Gly Asn Ile Phe Trp Tyr Phe Asp Leu Trp Gly Pro Gly Thr Leu
                100                 105                 110

Val Thr Val Ser Ser
            115

<210> SEQ ID NO 7
<211> LENGTH: 116
<212> TYPE: PRT
<213> ORGANISM: Artificial Sequence
<220> FEATURE:
<223> OTHER INFORMATION: CFA0666 VH

<400> SEQUENCE: 7

Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Thr Tyr Ala
                20                  25                  30

Met Gly Trp Val Arg Gln Ala Pro Gly Lys Gly Leu Glu Trp Ile Gly
            35                  40                  45

Thr Ile Asp Thr Gly Asp Ser Phe Tyr Ala Asn Trp Ala Lys Gly
        50                  55                  60

Arg Phe Thr Ile Ser Lys Thr Ser Thr Thr Val Asp Leu Lys Ile Thr
 65                  70                  75                  80

Ser Pro Thr Ala Glu Asp Thr Ala Thr Tyr Phe Cys Ala Arg Asn Asp
                     85                  90                  95

Gly Ser Val Tyr Asn Leu Phe Asn Leu Trp Gly Pro Gly Thr Leu Val
                100                 105                 110
```

Thr Val Ser Ser
        115

<210> SEQ ID NO 8
<211> LENGTH: 110
<212> TYPE: PRT
<213> ORGANISM: Artificial Sequence
<220> FEATURE:
<223> OTHER INFORMATION: CFA0672 VH

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Asn Ala
            20                  25                  30

Ile Asn Trp Val Arg Gln Ala Pro Gly Lys Gly Leu Glu Trp Ile Gly
        35                  40                  45

Cys Ile Tyr Thr Gly Ser Asp Thr Thr Tyr Tyr Ala Thr Trp Ala Lys
    50                  55                  60

Gly Arg Phe Thr Ile Ser Lys Thr Ser Thr Thr Val Asp Leu Lys Ile
65                  70                  75                  80

Ala Ser Pro Thr Thr Glu Asp Thr Ala Thr Tyr Phe Cys Ala Arg Gly
                85                  90                  95

Ser Gly Leu Trp Gly Pro Gly Thr Leu Val Thr Val Ser Ser
            100                 105                 110

<210> SEQ ID NO 9
<211> LENGTH: 116
<212> TYPE: PRT
<213> ORGANISM: Artificial Sequence
<220> FEATURE:
<223> OTHER INFORMATION: CFA0675 VH

<400> SEQUENCE: 9

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Met Gly Trp Val Arg Gln Ala Pro Gly Lys Gly Leu Glu Trp Ile Gly
        35                  40                  45

Thr Ile Asp Thr Gly Asp Asn Ser Phe Tyr Ala Asn Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Ala Glu Asp Thr Ala Thr Tyr Phe Cys Ala Arg Asn Asp
                85                  90                  95

Gly Ser Val Tyr Asn Leu Phe Asn Leu Trp Gly Pro Gly Thr Leu Val
            100                 105                 110

Thr Val Ser Ser
        115

<210> SEQ ID NO 10
<211> LENGTH: 123
<212> TYPE: PRT
<213> ORGANISM: Artificial Sequence
<220> FEATURE:
<223> OTHER INFORMATION: 305L05 VH

<400> SEQUENCE: 10

Gln Val Gln Leu Val Glu Ser Gly Gly Gly Leu Val Gln Pro Gly Gly

```
1               5                   10                  15
Ser Leu Arg Leu Ser Cys Ala Ala Ser Gly Phe Thr Ser His Ser Ser
                20                  25                  30

Tyr Tyr Val Ala Trp Val Arg Gln Ala Pro Gly Lys Gly Leu Glu Trp
            35                  40                  45

Val Gly Ala Ile Tyr Thr Gly Ser Gly Ala Thr Tyr Lys Ala Ser Trp
        50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
                100                 105                 110

Trp Gly Gln Gly Thr Leu Val Thr Val Ser Ser
            115                 120
```

<210> SEQ ID NO 11
<211> LENGTH: 110
<212> TYPE: PRT
<213> ORGANISM: Artificial Sequence
<220> FEATURE:
<223> OTHER INFORMATION: CFA0305 VL

<400> SEQUENCE: 11

```
Asp Val Val Met Thr Gln Thr Pro Ala Ser Val Ser Ala Ala Val Gly
1               5                   10                  15

Gly Thr Val Thr Ile Lys Cys Gln Ala Ser Gln Asn Ile Gly Ser Asp
                20                  25                  30

Leu Ala Trp Tyr Gln Gln Lys Pro Gly Gln Pro Arg Leu Leu Ile
            35                  40                  45

Tyr Gly Ala Ser Lys Leu Ala Ser Gly Val Ser Ser Arg Phe Ser Gly
        50                  55                  60

Ser Gly Ser Gly Lys Glu Phe Thr Leu Thr Ile Ser Asp Leu Glu Cys
65                  70                  75                  80

Ala Asp Ala Val Thr Tyr Tyr Cys Gln Cys Thr Phe Val Gly Ser Ser
                85                  90                  95

Tyr Gly Asn Ala Phe Gly Gly Gly Thr Glu Val Val Val Lys
                100                 105                 110
```

<210> SEQ ID NO 12
<211> LENGTH: 110
<212> TYPE: PRT
<213> ORGANISM: Artificial Sequence
<220> FEATURE:
<223> OTHER INFORMATION: CFA0307 VL

<400> SEQUENCE: 12

```
Ala Ile Glu Met Thr Gln Thr Pro Phe Ser Val Ser Ala Ala Val Gly
1               5                   10                  15

Gly Thr Val Thr Ile Lys Cys Gln Ala Ser Gln Asn Ile Tyr Ser Asn
                20                  25                  30

Leu Ala Trp Tyr Gln Gln Lys Pro Gly Gln Arg Pro Lys Leu Leu Ile
            35                  40                  45

Tyr Gly Ala Ser Asn Leu Glu Ser Gly Val Pro Ser Arg Phe Lys Gly
        50                  55                  60

Ser Gly Ser Gly Thr Glu Tyr Thr Leu Thr Ile Ser Asp Leu Glu Cys
65                  70                  75                  80
```

Ala Asp Ala Ala Thr Tyr Tyr Cys Leu Gln Gly Tyr Ser Tyr Ser Asn
            85                  90                  95

Val Asp Asp Ala Phe Gly Gly Gly Thr Glu Val Val Val Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: CFA0366 VL

<400> SEQUENCE: 13

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Ser
            20                  25                  30

Asp Tyr Leu Ser Trp Tyr Gln Gln Lys Pro Gly Gln Pro Pro Lys Leu
            35                  40                  45

Leu Ile Tyr Glu Ala Ser Lys Leu Ala Ser Gly Val Pro Pro Arg Phe
        50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Thr Tyr Tyr Ser
            85                  90                  95

Ser Gly Trp Tyr Phe Ala Phe Gly Gly Gly Thr Glu Val Val Val Lys
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: CFA0501 VL

<400> SEQUENCE: 14

Ala Tyr Asp Met Thr Gln Thr Pro Ala Ser Val Glu Val Ala Val Gly
1               5                   10                  15

Gly Thr Val Thr Ile Asn Cys Gln Ala Ser Glu Ser Ile Ser Asn Trp
            20                  25                  30

Leu Ala Trp Tyr Gln Gln Lys Pro Gly Gln Arg Pro Lys Leu Leu Ile
            35                  40                  45

Tyr Arg Ala Ser Thr Leu Ala Ser Gly Val Ser Ser Arg Phe Lys Gly
        50                  55                  60

Ser Gly Ser Gly Thr Gln Phe Thr Leu Thr Ile Ser Gly Val Glu Cys
65                  70                  75                  80

Asp Asp Ala Ala Thr Tyr Tyr Cys Gln Gln Asp Tyr Ser Ser Ser Asn
            85                  90                  95

Val Asp Asn Thr Phe Gly Gly Gly Thr Lys Val Val Val Glu
            100                 105                 110

<210> SEQ ID NO 15
<211> LENGTH: 110
<212> TYPE: PRT
<213> ORGANISM: Artificial Sequence
<220> FEATURE:
<223> OTHER INFORMATION: CFA0538 VL

<400> SEQUENCE: 15

Ala Tyr Asp Met Thr Gln Thr Pro Ala Ser Val Glu Val Ala Val Gly

-continued

```
1               5                   10                  15
Gly Thr Val Thr Ile Asn Cys Gln Ala Ser Glu Ser Ile Ser Asn Trp
            20                  25                  30

Leu Ala Trp Tyr Gln Gln Lys Pro Gly Gln Arg Pro Lys Leu Leu Ile
            35                  40                  45

Tyr Arg Ala Ser Thr Leu Ala Ser Gly Val Ser Arg Phe Lys Gly
        50                  55                  60

Ser Gly Ser Gly Thr Gln Phe Thr Leu Thr Ile Ser Gly Val Glu Cys
65                  70                  75                  80

Asp Asp Ala Ala Thr Tyr Tyr Cys Gln Gln Asp Tyr Ser Ser Asn
                85                  90                  95

Val Asp Asn Thr Phe Gly Gly Gly Thr Thr Val Val Val Glu
            100                 105                 110
```

<210> SEQ ID NO 16
<211> LENGTH: 110
<212> TYPE: PRT
<213> ORGANISM: Artificial Sequence
<220> FEATURE:
<223> OTHER INFORMATION: CFA0599 VL

<400> SEQUENCE: 16

```
Ala Tyr Asp Met Thr Gln Thr Pro Ala Ser Val Glu Val Ser Val Gly
1               5                   10                  15

Gly Thr Val Thr Ile Lys Cys Gln Ala Ser Glu Ser Ile Tyr Ser Ala
            20                  25                  30

Leu Ala Trp Tyr Gln Gln Lys Pro Gly Gln Pro Pro Lys Leu Leu Ile
            35                  40                  45

Tyr Ser Ala Ser Thr Leu Ala Ser Gly Val Pro Ser Arg Phe Lys Gly
        50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Gln Tyr Tyr Ser Ser Thr Asn
                85                  90                  95

Val His Asn Ser Phe Gly Gly Gly Thr Thr Val Val Val Glu
            100                 105                 110
```

<210> SEQ ID NO 17
<211> LENGTH: 110
<212> TYPE: PRT
<213> ORGANISM: Artificial Sequence
<220> FEATURE:
<223> OTHER INFORMATION: CFA0666 VL

<400> SEQUENCE: 17

```
Asp Val Val Met Thr Gln Thr Pro Ala Ser Val Ser Ala Ala Val Gly
1               5                   10                  15

Gly Thr Val Thr Ile Lys Cys Gln Ala Ser Glu Asn Ile Tyr Ser Ala
            20                  25                  30

Leu Ser Trp Tyr Gln Gln Lys Pro Gly Leu Arg Pro Arg Leu Leu Ile
            35                  40                  45

Tyr Tyr Ala Ser Thr Leu Ala Ser Gly Val Pro Ser Arg Phe Lys Gly
        50                  55                  60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Gln Tyr Tyr Asp Ile Asn Ser
                85                  90                  95
```

```
Val Asp Asn Thr Phe Gly Gly Gly Thr Lys Val Val Glu
            100                 105                 110
```

<210> SEQ ID NO 18
<211> LENGTH: 111
<212> TYPE: PRT
<213> ORGANISM: Artificial Sequence
<220> FEATURE:
<223> OTHER INFORMATION: CFA0672 VL

<400> SEQUENCE: 18

```
Asp Val Val Met Thr Gln Thr Pro Ala Ser Val Ser Ala Pro Val Gly
1               5                   10                  15

Gly Thr Val Thr Ile Lys Cys Gln Ala Ser Gln Asn Ile Tyr Ser Leu
            20                  25                  30

Leu Ala Trp Tyr Gln Gln Lys Pro Gly Gln Pro Pro Lys Leu Leu Ile
        35                  40                  45

Tyr His Thr Ser Asp Leu Ala Ser Gly Val Pro Ser Arg Phe Arg Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Ala Tyr Gly Ser Ser
                85                  90                  95

Asp Val Gly Gly Thr Phe Gly Gly Gly Thr Thr Val Val Val Glu
            100                 105                 110
```

<210> SEQ ID NO 19
<211> LENGTH: 110
<212> TYPE: PRT
<213> ORGANISM: Artificial Sequence
<220> FEATURE:
<223> OTHER INFORMATION: CFA0675 VL

<400> SEQUENCE: 19

```
Asp Val Val Met Thr Gln Thr Pro Ala Ser Val Ser Ala Ala Val Gly
1               5                   10                  15

Gly Thr Val Thr Ile Lys Cys Gln Ala Ser Glu Asn Ile Tyr Ser Ala
            20                  25                  30

Leu Ser Trp Tyr Gln Gln Lys Pro Gly Leu Arg Pro Arg Leu Leu Ile
        35                  40                  45

Tyr Tyr Ala Ser Thr Leu Ala Ser Gly Val Pro Ser Arg Phe Lys Gly
    50                  55                  60

Ser Arg Ser Gly Thr Glu Phe Thr Leu Thr Ile Ser Asp Leu Glu Cys
65                  70                  75                  80

Ala Asp Ala Ala Ser Tyr Tyr Cys Gln Gln Tyr Tyr Asp Ile Asn Ser
                85                  90                  95

Val Asp Asn Thr Phe Gly Gly Gly Thr Lys Val Val Val Glu
            100                 105                 110
```

<210> SEQ ID NO 20
<211> LENGTH: 110
<212> TYPE: PRT
<213> ORGANISM: Artificial Sequence
<220> FEATURE:
<223> OTHER INFORMATION: 305L05 VL

<400> SEQUENCE: 20

```
Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
```

```
            20                  25                  30
Leu Ala Trp Tyr Gln Gln Lys Pro Gly Gln Ala Pro Arg Leu Leu Ile
            35                  40                  45

Tyr Gly Ala Ser Lys Thr His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Lys Val Gly Ser Ser
                    85                  90                  95

Tyr Gly Asn His Phe Gly Gly Gly Thr Lys Val Glu Ile Lys
            100                 105                 110

<210> SEQ ID NO 21
<211> LENGTH: 117
<212> TYPE: PRT
<213> ORGANISM: Artificial Sequence
<220> FEATURE:
<223> OTHER INFORMATION: CFA0330 VH

<400> SEQUENCE: 21

Gln Ser Leu Glu Glu Ser Gly Gly Asp Leu Val Glu Pro Gly Ala Ser
1               5                   10                  15

Leu Thr Leu Thr Cys Thr Ala Ser Gly Phe Ser Trp Asn Ser Gly Tyr
            20                  25                  30

Asp Met Cys Trp Val Arg Gln Ala Pro Gly Lys Gly Leu Glu Trp Ile
            35                  40                  45

Ala Cys Ile Tyr Thr Gly Ser Ser Ala Asn Thr Ala Tyr Ala Asn Trp
        50                  55                  60

Ala Lys Gly Arg Phe Thr Ile Ser Lys Thr Ser Ser Thr Thr Val Thr
65                  70                  75                  80

Leu Gln Met Thr Gly Leu Thr Ala Ala Asp Thr Ala Thr Tyr Phe Cys
                    85                  90                  95

Ala Arg His Asp Asp Tyr Phe Phe Asp Leu Trp Gly Pro Gly Thr Leu
            100                 105                 110

Val Thr Val Ser Ser
            115

<210> SEQ ID NO 22
<211> LENGTH: 115
<212> TYPE: PRT
<213> ORGANISM: Artificial Sequence
<220> FEATURE:
<223> OTHER INFORMATION: CFA0341 VH

<400> SEQUENCE: 22

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Thr
            20                  25                  30

Met Gly Trp Val Arg Gln Ala Pro Gly Lys Gly Leu Glu Cys Ile Gly
            35                  40                  45

Tyr Ile His Ser Phe Gly Ser Thr Tyr Tyr Ala Ser Trp Ala Lys Gly
        50                  55                  60

Arg Phe Thr Ile Ser Lys Thr Ser Thr Thr Val Asp Leu Glu Ile Thr
65                  70                  75                  80

Ser Pro Thr Thr Glu Asp Thr Ala Thr Tyr Phe Cys Ala Arg Asp Val
                    85                  90                  95
```

```
Gly Gly Ser Ser Gly Trp Asp Leu Trp Gly Gln Gly Thr Leu Val Thr
                100                 105                 110

Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: CFA0329 VH

<400> SEQUENCE: 23

Gln Ser Leu Glu Glu Ser Gly Gly Gly Leu Val Lys Pro Gly Ala Ser
1               5                   10                  15

Leu Thr Leu Thr Cys Thr Ala Ser Gly Phe Ser Phe Ser Ser Gly Tyr
                20                  25                  30

Tyr Met Cys Trp Val Arg Gln Ala Pro Gly Lys Gly Leu Glu Trp Ile
            35                  40                  45

Gly Cys Ile Gly Thr Ile Ser Asp Ser Thr Tyr Tyr Ala Ser Trp Ala
        50                  55                  60

Lys Gly Arg Phe Pro Ile Ser Lys Ala Ser Ser Thr Val Thr Leu
65                  70                  75                  80

Gln Met Thr Ser Leu Thr Ala Ala Asp Thr Ala Thr Tyr Phe Cys Ala
                85                  90                  95

Arg Asp Pro Tyr Ser Tyr Gly Asp Leu Trp Gly Pro Gly Thr Leu Val
                100                 105                 110

Thr Val Ser Ser
        115

<210> SEQ ID NO 24
<211> LENGTH: 114
<212> TYPE: PRT
<213> ORGANISM: Artificial Sequence
<220> FEATURE:
<223> OTHER INFORMATION: CFA0330 VL

<400> SEQUENCE: 24

Asp Val Val Met Thr Gln Thr Pro Ala Ser Val Ser Glu Ser Val Gly
1               5                   10                  15

Gly Thr Val Thr Ile Asn Cys Gln Ala Ser Gln Ser Ile Gly Asn Asn
                20                  25                  30

Leu Ala Trp Tyr Gln Gln Lys Pro Gly Gln Pro Pro Lys Leu Leu Ile
            35                  40                  45

Tyr Asp Ala Ser Asn Leu Ala Ser Gly Val Pro Ser Arg Phe Lys Gly
        50                  55                  60

Ser Arg Ser Gly Thr Glu Pro Thr Leu Thr Asn Thr Leu Thr Ile Ser
65                  70                  75                  80

Gly Val Gln Cys Ala Asp Val Ala Thr Tyr Tyr Cys Gln Ser Gly Trp
                85                  90                  95

Tyr Gly Asn Ser Tyr Val Ala Ala Phe Gly Gly Gly Thr Glu Val Val
                100                 105                 110

Val Lys

<210> SEQ ID NO 25
<211> LENGTH: 112
<212> TYPE: PRT
<213> ORGANISM: Artificial Sequence
<220> FEATURE:
```

<223> OTHER INFORMATION: CFA0341 VL

<400> SEQUENCE: 25

Asp Val Val Met Thr Gln Thr Pro Ser Ser Val Ser Ala Ala Val Gly
1               5                   10                  15

Gly Thr Val Thr Ile Lys Cys Gln Ala Ser Glu Asn Ile Tyr Ser Asn
            20                  25                  30

Leu Ala Trp Tyr Gln Gln Lys Pro Gly Gln Pro Pro Lys Arg Leu Ile
        35                  40                  45

Tyr Asp Ala Ser Asp Leu Ala Ser Gly Val Pro Ser Arg Phe Ser Gly
    50                  55                  60

Ser Gly Tyr Gly Thr Gln Phe Thr Leu Thr Ile Ser Gly Val Gln Cys
65                  70                  75                  80

Glu Asp Ala Ala Thr Tyr Tyr Cys Gln Ala Asn Tyr Asp Ser Thr Ser
                85                  90                  95

Ser Ser Phe Gly Asn Val Phe Gly Gly Gly Thr Glu Val Val Val Lys
            100                 105                 110

<210> SEQ ID NO 26
<211> LENGTH: 110
<212> TYPE: PRT
<213> ORGANISM: Artificial Sequence
<220> FEATURE:
<223> OTHER INFORMATION: CFA0329 VL

<400> SEQUENCE: 26

Asp Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Gly Thr Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Leu Gly Gly Tyr Tyr Gly Phe Ser
                85                  90                  95

Tyr Gly Asn Ala Phe Gly Gly Gly Thr Glu Val Val Val Lys
            100                 105                 110

<210> SEQ ID NO 27
<211> LENGTH: 325
<212> TYPE: PRT
<213> ORGANISM: Artificial Sequence
<220> FEATURE:
<223> OTHER INFORMATION: F760G4

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr

```
                65                  70                  75                  80
Tyr Thr Cys Asn Val Asp His Lys Pro Ser Asn Thr Lys Val Asp Lys
                        85                  90                  95
Arg Val Glu Ser Lys Tyr Gly Pro Pro Cys Pro Pro Cys Pro Ala Pro
                        100                 105                 110
Glu Phe Arg Gly Gly Pro Lys Val Phe Leu Phe Pro Pro Lys Pro Lys
                        115                 120                 125
Asp Thr Leu Met Ile Ser Arg Thr Pro Glu Val Thr Cys Val Val Val
                130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                        165                 170                 175
Asn Ser Thr Tyr Arg Val Val Ser Val Leu Thr Val Leu His Gln Asp
                        180                 185                 190
Trp Leu Asn Gly Lys Glu Tyr Lys Cys Lys Val Ser Asn Lys Gly Leu
                        195                 200                 205
Pro Ser Ser Ile Glu Lys Thr Ile Ser Lys Ala Lys Gly Gln Pro Arg
                210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                        245                 250                 255
Ile Ala Val Glu Trp Glu Ser Asn Gly Gln Pro Glu Asn Asn Tyr Lys
                        260                 265                 270
Thr Thr Pro Pro Val Leu Asp Ser Asp Gly Ser Phe Phe Leu Tyr Ser
                        275                 280                 285
Arg Leu Thr Val Asp Lys Ser Arg Trp Gln Glu Gly Asn Val Phe Ser
                        290                 295                 300
Cys Ser Val Met His Glu Ala Leu His Asn His Tyr Thr Gln Lys Ser
305                 310                 315                 320
Leu Ser Leu Ser Leu
                325

<210> SEQ ID NO 28
<211> LENGTH: 325
<212> TYPE: PRT
<213> ORGANISM: Artificial Sequence
<220> FEATURE:
<223> OTHER INFORMATION: F939G4

<400> SEQUENCE: 28

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                        85                  90                  95
Arg Val Glu Ser Lys Tyr Gly Pro Pro Cys Pro Pro Cys Pro Ala Pro
```

```
            100                 105                 110
Glu Phe Arg Gly Gly Pro Lys Val Phe Leu Phe Pro Pro Lys Pro Lys
            115                 120                 125

Asp Thr Leu Tyr Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Tyr His Val Thr Gln Lys Ser
305                 310                 315                 320

Leu Ser Leu Ser Leu
                325

<210> SEQ ID NO 29
<211> LENGTH: 325
<212> TYPE: PRT
<213> ORGANISM: Artificial Sequence
<220> FEATURE:
<223> OTHER INFORMATION: SG402

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Gly Gly Pro Lys Val Phe Leu Phe Pro Pro Lys Pro Lys
        115                 120                 125

Asp Thr Leu Met Ile Ser Arg Thr Pro Glu Val Thr Cys Val Val Val
```

-continued

```
            130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 30
<211> LENGTH: 1676
<212> TYPE: PRT
<213> ORGANISM: Artificial Sequence
<220> FEATURE:
<223> OTHER INFORMATION: human C5

<400> SEQUENCE: 30

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
            35                  40                  45

Ala Phe Asp Ala Thr Ile Ser Ile Lys Ser Tyr Pro Asp Lys Lys Phe
        50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
                100                 105                 110

Lys Ser Lys Arg Met Pro Ile Thr Tyr Asp Asn Gly Phe Leu Phe Ile
            115                 120                 125

His Thr Asp Lys Pro Val Tyr Thr Pro Asp Gln Ser Val Lys Val Arg
        130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
```

```
                165                 170                 175
Ile Asp His Ile Gly Ile Ile Ser Phe Pro Asp Phe Lys Ile Pro Ser
                    180                 185                 190

Asn Pro Arg Tyr Gly Met Trp Thr Ile Lys Ala Lys Tyr Lys Glu Asp
                    195                 200                 205

Phe Ser Thr Thr Gly Thr Ala Tyr Phe Glu Val Lys Glu Tyr Val Leu
                    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                    245                 250                 255

Asn Lys Val Val Thr Glu Ala Asp Val Tyr Ile Thr Phe Gly Ile Arg
                    260                 265                 270

Glu Asp Leu Lys Asp Asp Gln Lys Glu Met Met Gln Thr Ala Met Gln
                    275                 280                 285

Asn Thr Met Leu Ile Asn Gly Ile Ala Gln Val Thr Phe Asp Ser Glu
                    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                    325                 330                 335

Ser Glu Glu Ala Glu Ile Pro Gly Ile Lys Tyr Val Leu Ser Pro Tyr
                    340                 345                 350

Lys Leu Asn Leu Val Ala Thr Pro Leu Phe Leu Lys Pro Gly Ile Pro
                    355                 360                 365

Tyr Pro Ile Lys Val Gln Val Lys Asp Ser Leu Asp Gln Leu Val Gly
                    370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                    405                 410                 415

Val Ala Ser Phe Val Leu Asn Leu Pro Ser Gly Val Thr Val Leu Glu
                    420                 425                 430

Phe Asn Val Lys Thr Asp Ala Pro Asp Leu Pro Glu Glu Asn Gln Ala
                    435                 440                 445

Arg Glu Gly Tyr Arg Ala Ile Ala Tyr Ser Ser Leu Ser Gln Ser Tyr
                    450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                    485                 490                 495

Thr His Tyr Asn Tyr Leu Ile Leu Ser Lys Gly Lys Ile Ile His Phe
                    500                 505                 510

Gly Thr Arg Glu Lys Phe Ser Asp Ala Ser Tyr Gln Ser Ile Asn Ile
                    515                 520                 525

Pro Val Thr Gln Asn Met Val Pro Ser Ser Arg Leu Leu Val Tyr Tyr
                    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                    565                 570                 575

Pro Asp Ala Asp Ala Tyr Ser Pro Gly Gln Thr Val Ser Leu Asn Met
                    580                 585                 590
```

```
Ala Thr Gly Met Asp Ser Trp Val Ala Leu Ala Ala Val Asp Ser Ala
            595                 600                 605

Val Tyr Gly Val Gln Arg Gly Ala Lys Lys Pro Leu Glu Arg Val Phe
            610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
            645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
            675                 680                 685

Lys Tyr Lys His Ser Val Val Lys Lys Cys Cys Tyr Asp Gly Ala Cys
            690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
            755                 760                 765

Phe Pro Glu Ser Trp Leu Trp Glu Val His Leu Val Pro Arg Arg Lys
            770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
            835                 840                 845

Arg Thr Ser Gly Met Gln Phe Cys Val Lys Met Ser Ala Val Glu Gly
            850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
            915                 920                 925

Val Val Pro Glu Gly Val Lys Arg Glu Ser Tyr Ser Gly Val Thr Leu
            930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu  Thr His Leu Pro Lys  Gly Ser Ala
            995                 1000                1005
```

-continued

```
Glu Ala Glu Leu Met Ser Val Val Pro Val Phe Tyr Val Phe His
    1010                1015                1020

Tyr Leu Glu Thr Gly Asn His Trp Asn Ile Phe His Ser Asp Pro
    1025                1030                1035

Leu Ile Glu Lys Gln Lys Leu Lys Lys Lys Leu Lys Glu Gly Met
    1040                1045                1050

Leu Ser Ile Met Ser Tyr Arg Asn Ala Asp Tyr Ser Tyr Ser Val
    1055                1060                1065

Trp Lys Gly Gly Ser Ala Ser Thr Trp Leu Thr Ala Phe Ala Leu
    1070                1075                1080

Arg Val Leu Gly Gln Val Asn Lys Tyr Val Glu Gln Asn Gln Asn
    1085                1090                1095

Ser Ile Cys Asn Ser Leu Leu Trp Leu Val Glu Asn Tyr Gln Leu
    1100                1105                1110

Asp Asn Gly Ser Phe Lys Glu Asn Ser Gln Tyr Gln Pro Ile Lys
    1115                1120                1125

Leu Gln Gly Thr Leu Pro Val Glu Ala Arg Glu Asn Ser Leu Tyr
    1130                1135                1140

Leu Thr Ala Phe Thr Val Ile Gly Ile Arg Lys Ala Phe Asp Ile
    1145                1150                1155

Cys Pro Leu Val Lys Ile Asp Thr Ala Leu Ile Lys Ala Asp Asn
    1160                1165                1170

Phe Leu Leu Glu Asn Thr Leu Pro Ala Gln Ser Thr Phe Thr Leu
    1175                1180                1185

Ala Ile Ser Ala Tyr Ala Leu Ser Leu Gly Asp Lys Thr His Pro
    1190                1195                1200

Gln Phe Arg Ser Ile Val Ser Ala Leu Lys Arg Glu Ala Leu Val
    1205                1210                1215

Lys Gly Asn Pro Pro Ile Tyr Arg Phe Trp Lys Asp Asn Leu Gln
    1220                1225                1230

His Lys Asp Ser Ser Val Pro Asn Thr Gly Thr Ala Arg Met Val
    1235                1240                1245

Glu Thr Thr Ala Tyr Ala Leu Leu Thr Ser Leu Asn Leu Lys Asp
    1250                1255                1260

Ile Asn Tyr Val Asn Pro Val Ile Lys Trp Leu Ser Glu Glu Gln
    1265                1270                1275

Arg Tyr Gly Gly Gly Phe Tyr Ser Thr Gln Asp Thr Ile Asn Ala
    1280                1285                1290

Ile Glu Gly Leu Thr Glu Tyr Ser Leu Leu Val Lys Gln Leu Arg
    1295                1300                1305

Leu Ser Met Asp Ile Asp Val Ser Tyr Lys His Lys Gly Ala Leu
    1310                1315                1320

His Asn Tyr Lys Met Thr Asp Lys Asn Phe Leu Gly Arg Pro Val
    1325                1330                1335

Glu Val Leu Leu Asn Asp Asp Leu Ile Val Ser Thr Gly Phe Gly
    1340                1345                1350

Ser Gly Leu Ala Thr Val His Val Thr Thr Val Val His Lys Thr
    1355                1360                1365

Ser Thr Ser Glu Glu Val Cys Ser Phe Tyr Leu Lys Ile Asp Thr
    1370                1375                1380

Gln Asp Ile Glu Ala Ser His Tyr Arg Gly Tyr Gly Asn Ser Asp
    1385                1390                1395

Tyr Lys Arg Ile Val Ala Cys Ala Ser Tyr Lys Pro Ser Arg Glu
```

-continued

```
                1400                1405                1410

Glu Ser Ser Ser Gly Ser Ser His Ala Val Met Asp Ile Ser Leu
        1415                1420                1425

Pro Thr Gly Ile Ser Ala Asn Glu Glu Asp Leu Lys Ala Leu Val
        1430                1435                1440

Glu Gly Val Asp Gln Leu Phe Thr Asp Tyr Gln Ile Lys Asp Gly
        1445                1450                1455

His Val Ile Leu Gln Leu Asn Ser Ile Pro Ser Ser Asp Phe Leu
        1460                1465                1470

Cys Val Arg Phe Arg Ile Phe Glu Leu Phe Glu Val Gly Phe Leu
        1475                1480                1485

Ser Pro Ala Thr Phe Thr Val Tyr Glu Tyr His Arg Pro Asp Lys
        1490                1495                1500

Gln Cys Thr Met Phe Tyr Ser Thr Ser Asn Ile Lys Ile Gln Lys
        1505                1510                1515

Val Cys Glu Gly Ala Ala Cys Lys Cys Val Glu Ala Asp Cys Gly
        1520                1525                1530

Gln Met Gln Glu Glu Leu Asp Leu Thr Ile Ser Ala Glu Thr Arg
        1535                1540                1545

Lys Gln Thr Ala Cys Lys Pro Glu Ile Ala Tyr Ala Tyr Lys Val
        1550                1555                1560

Ser Ile Thr Ser Ile Thr Val Glu Asn Val Phe Val Lys Tyr Lys
        1565                1570                1575

Ala Thr Leu Leu Asp Ile Tyr Lys Thr Gly Glu Ala Val Ala Glu
        1580                1585                1590

Lys Asp Ser Glu Ile Thr Phe Ile Lys Lys Val Thr Cys Thr Asn
        1595                1600                1605

Ala Glu Leu Val Lys Gly Arg Gln Tyr Leu Ile Met Gly Lys Glu
        1610                1615                1620

Ala Leu Gln Ile Lys Tyr Asn Phe Ser Phe Arg Tyr Ile Tyr Pro
        1625                1630                1635

Leu Asp Ser Leu Thr Trp Ile Glu Tyr Trp Pro Arg Asp Thr Thr
        1640                1645                1650

Cys Ser Ser Cys Gln Ala Phe Leu Ala Asn Leu Asp Glu Phe Ala
        1655                1660                1665

Glu Asp Ile Phe Leu Asn Gly Cys
        1670                1675

<210> SEQ ID NO 31
<211> LENGTH: 673
<212> TYPE: PRT
<213> ORGANISM: Artificial Sequence
<220> FEATURE:
<223> OTHER INFORMATION: human C5, beta chain

<400> SEQUENCE: 31

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
```

```
                 65                  70                  75                  80
Asn Ser Ala Ile Leu Thr Ile Gln Pro Lys Gln Leu Pro Gly Gly Gln
                 85                  90                  95

Asn Pro Val Ser Tyr Val Tyr Leu Glu Val Ser Lys His Phe Ser
                100                 105                 110

Lys Ser Lys Arg Met Pro Ile Thr Tyr Asp Asn Gly Phe Leu Phe Ile
                115                 120                 125

His Thr Asp Lys Pro Val Tyr Thr Pro Asp Gln Ser Val Lys Val Arg
                130                 135                 140

Val Tyr Ser Leu Asn Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
                180                 185                 190

Asn Pro Arg Tyr Gly Met Trp Thr Ile Lys Ala Lys Tyr Lys Glu Asp
                195                 200                 205

Phe Ser Thr Thr Gly Thr Ala Tyr Phe Glu Val Lys Glu Tyr Val Leu
                210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
                260                 265                 270

Glu Asp Leu Lys Asp Asp Gln Lys Glu Met Met Gln Thr Ala Met Gln
                275                 280                 285

Asn Thr Met Leu Ile Asn Gly Ile Ala Gln Val Thr Phe Asp Ser Glu
                290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
                340                 345                 350

Lys Leu Asn Leu Val Ala Thr Pro Leu Phe Leu Lys Pro Gly Ile Pro
                355                 360                 365

Tyr Pro Ile Lys Val Gln Val Lys Asp Ser Leu Asp Gln Leu Val Gly
                370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
                420                 425                 430

Phe Asn Val Lys Thr Asp Ala Pro Asp Leu Pro Glu Glu Asn Gln Ala
                435                 440                 445

Arg Glu Gly Tyr Arg Ala Ile Ala Tyr Ser Ser Leu Ser Gln Ser Tyr
                450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495
```

```
Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
            515                 520                 525

Pro Val Thr Gln Asn Met Val Pro Ser Ser Arg Leu Leu Val Tyr Tyr
        530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
        580                 585                 590

Ala Thr Gly Met Asp Ser Trp Val Ala Leu Ala Val Asp Ser Ala
            595                 600                 605

Val Tyr Gly Val Gln Arg Gly Ala Lys Lys Pro Leu Glu Arg Val Phe
        610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu

<210> SEQ ID NO 32
<211> LENGTH: 105
<212> TYPE: PRT
<213> ORGANISM: Artificial Sequence
<220> FEATURE:
<223> OTHER INFORMATION: human C5, MG1

<400> SEQUENCE: 32

Glu Gln Thr Tyr Val Ile Ser Ala Pro Lys Ile Phe Arg Val Gly Ala
1               5                   10                  15

Ser Glu Asn Ile Val Ile Gln Val Tyr Gly Tyr Thr Glu Ala Phe Asp
            20                  25                  30

Ala Thr Ile Ser Ile Lys Ser Tyr Pro Asp Lys Lys Phe Ser Tyr Ser
        35                  40                  45

Ser Gly His Val His Leu Ser Ser Glu Asn Lys Phe Gln Asn Ser Ala
    50                  55                  60

Ile Leu Thr Ile Gln Pro Lys Gln Leu Pro Gly Gly Gln Asn Pro Val
65                  70                  75                  80

Ser Tyr Val Tyr Leu Glu Val Val Ser Lys His Phe Ser Lys Ser Lys
                85                  90                  95

Arg Met Pro Ile Thr Tyr Asp Asn Gly
            100                 105

<210> SEQ ID NO 33
<211> LENGTH: 101
<212> TYPE: PRT
<213> ORGANISM: Artificial Sequence
<220> FEATURE:
<223> OTHER INFORMATION: human C5, MG2

<400> SEQUENCE: 33

Phe Leu Phe Ile His Thr Asp Lys Pro Val Tyr Thr Pro Asp Gln Ser
1               5                   10                  15
```

```
Val Lys Val Arg Val Tyr Ser Leu Asn Asp Leu Lys Pro Ala Lys
         20                  25                  30

Arg Glu Thr Val Leu Thr Phe Ile Asp Pro Glu Gly Ser Glu Val Asp
             35                  40                  45

Met Val Glu Glu Ile Asp His Ile Gly Ile Ile Ser Phe Pro Asp Phe
 50                  55                  60

Lys Ile Pro Ser Asn Pro Arg Tyr Gly Met Trp Thr Ile Lys Ala Lys
 65                  70                  75                  80

Tyr Lys Glu Asp Phe Ser Thr Thr Gly Thr Ala Tyr Phe Glu Val Lys
                 85                  90                  95

Glu Tyr Val Leu Pro
                100

<210> SEQ ID NO 34
<211> LENGTH: 225
<212> TYPE: PRT
<213> ORGANISM: Artificial Sequence
<220> FEATURE:
<223> OTHER INFORMATION: human C5, MG1-MG2

<400> SEQUENCE: 34

Met Gly Leu Leu Gly Ile Leu Cys Phe Leu Ile Phe Leu Gly Lys Thr
 1               5                  10                  15

Trp Gly Gln Glu Gln Thr Tyr Val Ile Ser Ala Pro Lys Ile Phe Arg
             20                  25                  30

Val Gly Ala Ser Glu Asn Ile Val Ile Gln Val Tyr Gly Tyr Thr Glu
         35                  40                  45

Ala Phe Asp Ala Thr Ile Ser Ile Lys Ser Tyr Pro Asp Lys Lys Phe
 50                  55                  60

Ser Tyr Ser Ser Gly His Val His Leu Ser Ser Glu Asn Lys Phe Gln
 65                  70                  75                  80

Asn Ser Ala Ile Leu Thr Ile Gln Pro Lys Gln Leu Pro Gly Gly Gln
                 85                  90                  95

Asn Pro Val Ser Tyr Val Tyr Leu Glu Val Val Ser Lys His Phe Ser
                100                 105                 110

Lys Ser Lys Arg Met Pro Ile Thr Tyr Asp Asn Gly Phe Leu Phe Ile
             115                 120                 125

His Thr Asp Lys Pro Val Tyr Thr Pro Asp Gln Ser Val Lys Val Arg
         130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro
225

<210> SEQ ID NO 35
<211> LENGTH: 1676
<212> TYPE: PRT
<213> ORGANISM: Artificial Sequence
```

<220> FEATURE:
<223> OTHER INFORMATION: cynomolgus C5

<400> SEQUENCE: 35

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Val Leu Thr Ile Gln Pro Lys Gln Leu Pro Gly Gly Gln
                85                  90                  95

Asn Gln Val Ser Tyr Val Tyr Leu Glu Val Val Ser Lys His Phe Ser
            100                 105                 110

Lys Ser Lys Lys Ile Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Ile Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Gln Ala Lys Tyr Lys Glu Asp
        195                 200                 205

Phe Ser Thr Thr Gly Thr Ala Phe Phe Glu Val Lys Glu Tyr Val Leu
    210                 215                 220

Pro His Phe Ser Val Ser Val Glu Pro Glu Ser Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Glu Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Ser Ile Lys Val Gln Val Lys Asp Ala Leu Asp Gln Leu Val Gly
    370                 375                 380

Gly Val Pro Val Thr Leu Asn Ala Gln Thr Ile Asp Val Asn Gln Glu
385                 390                 395                 400
```

```
Thr Ser Asp Leu Glu Pro Arg Lys Ser Val Thr Arg Val Asp Asp Gly
            405                 410                 415

Val Ala Ser Phe Val Val Asn Leu Pro Ser Gly Val Thr Val Leu Glu
        420                 425                 430

Phe Asn Val Lys Thr Asp Ala Pro Asp Leu Pro Asp Glu Asn Gln Ala
            435                 440                 445

Arg Glu Gly Tyr Arg Ala Ile Ala Tyr Ser Ser Leu Ser Gln Ser Tyr
        450                 455                 460

Leu Tyr Ile Asp Trp Thr Asp Asn His Lys Ala Leu Leu Val Gly Glu
465                 470                 475                 480

Tyr Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Leu Ser Asp Ala Ser Tyr Gln Ser Ile Asn Ile
        515                 520                 525

Pro Val Thr Gln Asn Met Val Pro Ser Ser Arg Leu Leu Val Tyr Tyr
        530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Thr Tyr Ser Pro Gly Gln Thr Val Ser Leu Asn Met
            580                 585                 590

Val Thr Gly Met Asp Ser Trp Val Ala Leu Thr Ala Val Asp Ser Ala
        595                 600                 605

Val Tyr Gly Val Gln Arg Arg Ala Lys Lys Pro Leu Glu Arg Val Phe
        610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Ile Arg Pro Arg Arg Met Leu Gln Glu Lys Ile Glu Glu Ile Ala Ala
        675                 680                 685

Lys Tyr Lys His Leu Val Val Lys Cys Cys Tyr Asp Gly Val Arg
        690                 695                 700

Ile Asn His Asp Glu Thr Cys Glu Gln Arg Ala Ala Arg Ile Ser Val
705                 710                 715                 720

Gly Pro Arg Cys Val Lys Ala Phe Thr Glu Cys Cys Val Val Ala Ser
                725                 730                 735

Gln Leu Arg Ala Asn Asn Ser His Lys Asp Leu Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
        770                 775                 780

Gln Leu Gln Phe Ala Leu Pro Asp Ser Val Thr Thr Trp Glu Ile Gln
785                 790                 795                 800

Gly Val Gly Ile Ser Asn Ser Gly Ile Cys Val Ala Asp Thr Ile Lys
                805                 810                 815
```

```
Ala Lys Val Phe Lys Asp Val Phe Leu Glu Met Asn Ile Pro Tyr Ser
            820                 825                 830

Val Val Arg Gly Glu Gln Val Gln Leu Lys Gly Thr Val Tyr Asn Tyr
            835                 840                 845

Arg Thr Ser Gly Met Gln Phe Cys Val Lys Met Ser Ala Val Glu Gly
            850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser Asn His Leu Val
                885                 890                 895

Thr Phe Thr Val Leu Pro Leu Glu Ile Gly Leu Gln Asn Ile Asn Phe
            900                 905                 910

Ser Leu Glu Thr Ser Phe Gly Lys Glu Ile Leu Val Lys Ser Leu Arg
            915                 920                 925

Val Val Pro Glu Gly Val Lys Arg Glu Ser Tyr Ser Gly Ile Thr Leu
            930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Arg Glu Gly Ile Asn Ile Leu Thr His Leu Pro Lys Gly Ser Ala
            995                 1000                1005

Glu Ala Glu Leu Met Ser Val Val Pro Val Phe Tyr Val Phe His
            1010                1015                1020

Tyr Leu Glu Thr Gly Asn His Trp Asn Ile Phe His Ser Asp Pro
            1025                1030                1035

Leu Ile Glu Lys Arg Asn Leu Glu Lys Lys Leu Lys Glu Gly Met
            1040                1045                1050

Val Ser Ile Met Ser Tyr Arg Asn Ala Asp Tyr Ser Tyr Ser Val
            1055                1060                1065

Trp Lys Gly Gly Ser Ala Ser Thr Trp Leu Thr Ala Phe Ala Leu
            1070                1075                1080

Arg Val Leu Gly Gln Val His Lys Tyr Val Glu Gln Asn Gln Asn
            1085                1090                1095

Ser Ile Cys Asn Ser Leu Leu Trp Leu Val Glu Asn Tyr Gln Leu
            1100                1105                1110

Asp Asn Gly Ser Phe Lys Glu Asn Ser Gln Tyr Gln Pro Ile Lys
            1115                1120                1125

Leu Gln Gly Thr Leu Pro Val Glu Ala Arg Glu Asn Ser Leu Tyr
            1130                1135                1140

Leu Thr Ala Phe Thr Val Ile Gly Ile Arg Lys Ala Phe Asp Ile
            1145                1150                1155

Cys Pro Leu Val Lys Ile Asn Thr Ala Leu Ile Lys Ala Asp Thr
            1160                1165                1170

Phe Leu Leu Glu Asn Thr Leu Pro Ala Gln Ser Thr Phe Thr Leu
            1175                1180                1185

Ala Ile Ser Ala Tyr Ala Leu Ser Leu Gly Asp Lys Thr His Pro
            1190                1195                1200

Gln Phe Arg Ser Ile Val Ser Ala Leu Lys Arg Glu Ala Leu Val
            1205                1210                1215

Lys Gly Asn Pro Pro Ile Tyr Arg Phe Trp Lys Asp Ser Leu Gln
```

-continued

```
            1220                1225                1230
His Lys Asp Ser Ser Val Pro Asn Thr Gly Thr Ala Arg Met Val
        1235                1240                1245
Glu Thr Thr Ala Tyr Ala Leu Leu Thr Ser Leu Asn Leu Lys Asp
        1250                1255                1260
Ile Asn Tyr Val Asn Pro Ile Ile Lys Trp Leu Ser Glu Glu Gln
        1265                1270                1275
Arg Tyr Gly Gly Gly Phe Tyr Ser Thr Gln Asp Thr Ile Asn Ala
        1280                1285                1290
Ile Glu Gly Leu Thr Glu Tyr Ser Leu Leu Val Lys Gln Leu Arg
        1295                1300                1305
Leu Asn Met Asp Ile Asp Val Ala Tyr Lys His Lys Gly Pro Leu
        1310                1315                1320
His Asn Tyr Lys Met Thr Asp Lys Asn Phe Leu Gly Arg Pro Val
        1325                1330                1335
Glu Val Leu Leu Asn Asp Asp Leu Val Val Ser Thr Gly Phe Gly
        1340                1345                1350
Ser Gly Leu Ala Thr Val His Val Thr Thr Val His Lys Thr
        1355                1360                1365
Ser Thr Ser Glu Glu Val Cys Ser Phe Tyr Leu Lys Ile Asp Thr
        1370                1375                1380
Gln Asp Ile Glu Ala Ser His Tyr Arg Gly Tyr Gly Asn Ser Asp
        1385                1390                1395
Tyr Lys Arg Ile Val Ala Cys Ala Ser Tyr Lys Pro Ser Lys Glu
        1400                1405                1410
Glu Ser Ser Ser Gly Ser Ser His Ala Val Met Asp Ile Ser Leu
        1415                1420                1425
Pro Thr Gly Ile Asn Ala Asn Glu Glu Asp Leu Lys Ala Leu Val
        1430                1435                1440
Glu Gly Val Asp Gln Leu Phe Thr Asp Tyr Gln Ile Lys Asp Gly
        1445                1450                1455
His Val Ile Leu Gln Leu Asn Ser Ile Pro Ser Ser Asp Phe Leu
        1460                1465                1470
Cys Val Arg Phe Arg Ile Phe Glu Leu Phe Glu Val Gly Phe Leu
        1475                1480                1485
Ser Pro Ala Thr Phe Thr Val Tyr Glu Tyr His Arg Pro Asp Lys
        1490                1495                1500
Gln Cys Thr Met Phe Tyr Ser Thr Ser Asn Ile Lys Ile Gln Lys
        1505                1510                1515
Val Cys Glu Gly Ala Thr Cys Lys Cys Ile Glu Ala Asp Cys Gly
        1520                1525                1530
Gln Met Gln Lys Glu Leu Asp Leu Thr Ile Ser Ala Glu Thr Arg
        1535                1540                1545
Lys Gln Thr Ala Cys Asn Pro Glu Ile Ala Tyr Ala Tyr Lys Val
        1550                1555                1560
Ile Ile Thr Ser Ile Thr Thr Glu Asn Val Phe Val Lys Tyr Lys
        1565                1570                1575
Ala Thr Leu Leu Asp Ile Tyr Lys Thr Gly Glu Ala Val Ala Glu
        1580                1585                1590
Lys Asp Ser Glu Ile Thr Phe Ile Lys Lys Val Thr Cys Thr Asn
        1595                1600                1605
Ala Glu Leu Val Lys Gly Arg Gln Tyr Leu Ile Met Gly Lys Glu
        1610                1615                1620
```

```
Ala Leu Gln Ile Lys Tyr Asn Phe Thr Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670            1675

<210> SEQ ID NO 36
<211> LENGTH: 6
<212> TYPE: PRT
<213> ORGANISM: Artificial Sequence
<220> FEATURE:
<223> OTHER INFORMATION: CFA0305 HVR-H1

<400> SEQUENCE: 36

Ser Ser Tyr Tyr Met Cys
1               5

<210> SEQ ID NO 37
<211> LENGTH: 6
<212> TYPE: PRT
<213> ORGANISM: Artificial Sequence
<220> FEATURE:
<223> OTHER INFORMATION: CFA0307 HVR-H1

<400> SEQUENCE: 37

Asn Phe Tyr Tyr Ile Cys
1               5

<210> SEQ ID NO 38
<211> LENGTH: 6
<212> TYPE: PRT
<213> ORGANISM: Artificial Sequence
<220> FEATURE:
<223> OTHER INFORMATION: CFA0366 HVR-H1

<400> SEQUENCE: 38

Ser Ser Tyr Tyr Met Cys
1               5

<210> SEQ ID NO 39
<211> LENGTH: 6
<212> TYPE: PRT
<213> ORGANISM: Artificial Sequence
<220> FEATURE:
<223> OTHER INFORMATION: CFA0501 HVR-H1

<400> SEQUENCE: 39

Ser Ser Tyr Tyr Met Asn
1               5

<210> SEQ ID NO 40
<211> LENGTH: 6
<212> TYPE: PRT
<213> ORGANISM: Artificial Sequence
<220> FEATURE:
<223> OTHER INFORMATION: CFA0538 HVR-H1

<400> SEQUENCE: 40

Ser Ser Tyr Tyr Met Asn
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: CFA0599 HVR-H1

<400> SEQUENCE: 41

Asp Asn Thr Met Thr
1               5

<210> SEQ ID NO 42
<211> LENGTH: 5
<212> TYPE: PRT
<213> ORGANISM: Artificial Sequence
<220> FEATURE:
<223> OTHER INFORMATION: CFA0666 HVR-H1

<400> SEQUENCE: 42

Thr Tyr Ala Met Gly
1               5

<210> SEQ ID NO 43
<211> LENGTH: 5
<212> TYPE: PRT
<213> ORGANISM: Artificial Sequence
<220> FEATURE:
<223> OTHER INFORMATION: CFA0672 HVR-H1

<400> SEQUENCE: 43

Gly Asn Ala Ile Asn
1               5

<210> SEQ ID NO 44
<211> LENGTH: 5
<212> TYPE: PRT
<213> ORGANISM: Artificial Sequence
<220> FEATURE:
<223> OTHER INFORMATION: CFA0675 HVR-H1

<400> SEQUENCE: 44

Thr Tyr Ala Met Gly
1               5

<210> SEQ ID NO 45
<211> LENGTH: 6
<212> TYPE: PRT
<213> ORGANISM: Artificial Sequence
<220> FEATURE:
<223> OTHER INFORMATION: 305L05 HVR-H1

<400> SEQUENCE: 45

Ser Ser Tyr Tyr Val Ala
1               5

<210> SEQ ID NO 46
<211> LENGTH: 17
<212> TYPE: PRT
<213> ORGANISM: Artificial Sequence
<220> FEATURE:
<223> OTHER INFORMATION: CFA0305 HVR-H2

<400> SEQUENCE: 46

Cys Ile Tyr Thr Gly Ser Gly Ala Thr Tyr Tyr Ala Ser Trp Ala Lys
1               5                   10                  15
Gly
```

<210> SEQ ID NO 47
<211> LENGTH: 17
<212> TYPE: PRT
<213> ORGANISM: Artificial Sequence
<220> FEATURE:
<223> OTHER INFORMATION: CFA0307 HVR-H2

<400> SEQUENCE: 47

Cys Ile Tyr Thr Val Ser Gly Tyr Thr Tyr Tyr Ala Ser Trp Ala Lys
1               5                   10                  15

Gly

<210> SEQ ID NO 48
<211> LENGTH: 18
<212> TYPE: PRT
<213> ORGANISM: Artificial Sequence
<220> FEATURE:
<223> OTHER INFORMATION: CFA0366 HVR-H2

<400> SEQUENCE: 48

Cys Ile Tyr Ala Gly Ser Ser Gly Ile Ile Tyr Tyr Ala Asn Trp Ala
1               5                   10                  15

Lys Gly

<210> SEQ ID NO 49
<211> LENGTH: 16
<212> TYPE: PRT
<213> ORGANISM: Artificial Sequence
<220> FEATURE:
<223> OTHER INFORMATION: CFA0501 HVR-H2

<400> SEQUENCE: 49

Met Ile Tyr Gly Ser Gly Ala Thr Tyr Tyr Ala Ser Trp Ala Lys Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: CFA0538 HVR-H2

<400> SEQUENCE: 50

Met Ile Tyr Gly Ser Gly Ala Thr Tyr Tyr Ala Ser Trp Ala Lys Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: CFA0599 HVR-H2

<400> SEQUENCE: 51

Ile Ile Ser Phe Gly Gly Asp Ala Tyr Tyr Ala Ser Trp Ala Lys Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: CFA0666 HVR-H2

<400> SEQUENCE: 52

```
Thr Ile Asp Thr Gly Asp Asn Ser Phe Tyr Ala Asn Trp Ala Lys Gly
1               5                   10                  15
```

<210> SEQ ID NO 53
<211> LENGTH: 17
<212> TYPE: PRT
<213> ORGANISM: Artificial Sequence
<220> FEATURE:
<223> OTHER INFORMATION: CFA0672 HVR-H2

<400> SEQUENCE: 53

```
Cys Ile Tyr Thr Gly Ser Asp Thr Thr Tyr Tyr Ala Thr Trp Ala Lys
1               5                   10                  15

Gly
```

<210> SEQ ID NO 54
<211> LENGTH: 16
<212> TYPE: PRT
<213> ORGANISM: Artificial Sequence
<220> FEATURE:
<223> OTHER INFORMATION: CFA0675 HVR-H2

<400> SEQUENCE: 54

```
Thr Ile Asp Thr Gly Asp Asn Ser Phe Tyr Ala Asn Trp Ala Lys Gly
1               5                   10                  15
```

<210> SEQ ID NO 55
<211> LENGTH: 17
<212> TYPE: PRT
<213> ORGANISM: Artificial Sequence
<220> FEATURE:
<223> OTHER INFORMATION: 305L05 HVR-H2

<400> SEQUENCE: 55

```
Ala Ile Tyr Thr Gly Ser Gly Ala Thr Tyr Lys Ala Ser Trp Ala Lys
1               5                   10                  15

Gly
```

<210> SEQ ID NO 56
<211> LENGTH: 13
<212> TYPE: PRT
<213> ORGANISM: Artificial Sequence
<220> FEATURE:
<223> OTHER INFORMATION: CFA0305 HVR-H3

<400> SEQUENCE: 56

```
Asp Gly Gly Tyr Val Thr Pro Thr His Ala Met Tyr Leu
1               5                   10
```

<210> SEQ ID NO 57
<211> LENGTH: 9
<212> TYPE: PRT
<213> ORGANISM: Artificial Sequence
<220> FEATURE:
<223> OTHER INFORMATION: CFA0307 HVR-H3

<400> SEQUENCE: 57

```
Asp Leu His Ala Gly Ile Thr Asn Leu
1               5
```

<210> SEQ ID NO 58
<211> LENGTH: 13
<212> TYPE: PRT
<213> ORGANISM: Artificial Sequence
<220> FEATURE:
<223> OTHER INFORMATION: CFA0366 HVR-H3

```
<400> SEQUENCE: 58

Tyr Pro Thr Tyr Gly Asp Gly Gly His Ala Phe Asn Leu
1               5                   10

<210> SEQ ID NO 59
<211> LENGTH: 11
<212> TYPE: PRT
<213> ORGANISM: Artificial Sequence
<220> FEATURE:
<223> OTHER INFORMATION: CFA0501 HVR-H3

<400> SEQUENCE: 59

Gln Ile Tyr Ser Gly Asp Asn Asn Asp Asn Phe
1               5                   10

<210> SEQ ID NO 60
<211> LENGTH: 11
<212> TYPE: PRT
<213> ORGANISM: Artificial Sequence
<220> FEATURE:
<223> OTHER INFORMATION: CFA0538 HVR-H3

<400> SEQUENCE: 60

Gln Ile Tyr Ser Gly Asp Asn Asn Asp Asn Phe
1               5                   10

<210> SEQ ID NO 61
<211> LENGTH: 12
<212> TYPE: PRT
<213> ORGANISM: Artificial Sequence
<220> FEATURE:
<223> OTHER INFORMATION: CFA0599 HVR-H3

<400> SEQUENCE: 61

Val Gly Ala Gly Asn Ile Phe Trp Tyr Phe Asp Leu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: CFA0666 HVR-H3

<400> SEQUENCE: 62

Asn Asp Gly Ser Val Tyr Asn Leu Phe Asn Leu
1               5                   10

<210> SEQ ID NO 63
<211> LENGTH: 4
<212> TYPE: PRT
<213> ORGANISM: Artificial Sequence
<220> FEATURE:
<223> OTHER INFORMATION: CFA0672 HVR-H3

<400> SEQUENCE: 63

Gly Ser Gly Leu
1

<210> SEQ ID NO 64
<211> LENGTH: 11
<212> TYPE: PRT
<213> ORGANISM: Artificial Sequence
<220> FEATURE:
<223> OTHER INFORMATION: CFA0675 HVR-H3
```

```
<400> SEQUENCE: 64

Asn Asp Gly Ser Val Tyr Asn Leu Phe Asn Leu
1               5                   10

<210> SEQ ID NO 65
<211> LENGTH: 13
<212> TYPE: PRT
<213> ORGANISM: Artificial Sequence
<220> FEATURE:
<223> OTHER INFORMATION: 305L05 HVR-H3

<400> SEQUENCE: 65

Asp Gly Gly Tyr Asp Tyr Pro Thr His Ala Met His Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: CFA0305 HVR-L1

<400> SEQUENCE: 66

Gln Ala Ser Gln Asn Ile Gly Ser Asp Leu Ala
1               5                   10

<210> SEQ ID NO 67
<211> LENGTH: 11
<212> TYPE: PRT
<213> ORGANISM: Artificial Sequence
<220> FEATURE:
<223> OTHER INFORMATION: CFA0307 HVR-L1

<400> SEQUENCE: 67

Gln Ala Ser Gln Asn Ile Tyr Ser Asn Leu Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: CFA0366 HVR-L1

<400> SEQUENCE: 68

Gln Ser Ser Gln Ser Val Tyr Ser Ser Asp Tyr Leu Ser
1               5                   10

<210> SEQ ID NO 69
<211> LENGTH: 11
<212> TYPE: PRT
<213> ORGANISM: Artificial Sequence
<220> FEATURE:
<223> OTHER INFORMATION: CFA0501 HVR-L1

<400> SEQUENCE: 69

Gln Ala Ser Glu Ser Ile Ser Asn Trp Leu Ala
1               5                   10

<210> SEQ ID NO 70
<211> LENGTH: 11
<212> TYPE: PRT
<213> ORGANISM: Artificial Sequence
<220> FEATURE:
<223> OTHER INFORMATION: CFA0538 HVR-L1

<400> SEQUENCE: 70
```

```
Gln Ala Ser Glu Ser Ile Ser Asn Trp Leu Ala
1               5                   10

<210> SEQ ID NO 71
<211> LENGTH: 11
<212> TYPE: PRT
<213> ORGANISM: Artificial Sequence
<220> FEATURE:
<223> OTHER INFORMATION: CFA0599 HVR-L1

<400> SEQUENCE: 71

Gln Ala Ser Glu Ser Ile Tyr Ser Ala Leu Ala
1               5                   10

<210> SEQ ID NO 72
<211> LENGTH: 11
<212> TYPE: PRT
<213> ORGANISM: Artificial Sequence
<220> FEATURE:
<223> OTHER INFORMATION: CFA0666 HVR-L1

<400> SEQUENCE: 72

Gln Ala Ser Glu Asn Ile Tyr Ser Ala Leu Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: CFA0672 HVR-L1

<400> SEQUENCE: 73

Gln Ala Ser Gln Asn Ile Tyr Ser Leu Leu Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: CFA0675 HVR-L1

<400> SEQUENCE: 74

Gln Ala Ser Glu Asn Ile Tyr Ser Ala Leu Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: 305L05 HVR-L1

<400> SEQUENCE: 75

Gln Ala Ser Gln Asn Ile Gly Ser Ser Leu Ala
1               5                   10

<210> SEQ ID NO 76
<211> LENGTH: 7
<212> TYPE: PRT
<213> ORGANISM: Artificial Sequence
<220> FEATURE:
<223> OTHER INFORMATION: CFA0305 HVR-L2

<400> SEQUENCE: 76
```

Gly Ala Ser Lys Leu Ala Ser
1               5

<210> SEQ ID NO 77
<211> LENGTH: 7
<212> TYPE: PRT
<213> ORGANISM: Artificial Sequence
<220> FEATURE:
<223> OTHER INFORMATION: CFA0307 HVR-L2

<400> SEQUENCE: 77

Gly Ala Ser Asn Leu Glu Ser
1               5

<210> SEQ ID NO 78
<211> LENGTH: 7
<212> TYPE: PRT
<213> ORGANISM: Artificial Sequence
<220> FEATURE:
<223> OTHER INFORMATION: CFA0366 HVR-L2

<400> SEQUENCE: 78

Glu Ala Ser Lys Leu Ala Ser
1               5

<210> SEQ ID NO 79
<211> LENGTH: 7
<212> TYPE: PRT
<213> ORGANISM: Artificial Sequence
<220> FEATURE:
<223> OTHER INFORMATION: CFA0501 HVR-L2

<400> SEQUENCE: 79

Arg Ala Ser Thr Leu Ala Ser
1               5

<210> SEQ ID NO 80
<211> LENGTH: 7
<212> TYPE: PRT
<213> ORGANISM: Artificial Sequence
<220> FEATURE:
<223> OTHER INFORMATION: CFA0538 HVR-L2

<400> SEQUENCE: 80

Arg Ala Ser Thr Leu Ala Ser
1               5

<210> SEQ ID NO 81
<211> LENGTH: 7
<212> TYPE: PRT
<213> ORGANISM: Artificial Sequence
<220> FEATURE:
<223> OTHER INFORMATION: CFA0599 HVR-L2

<400> SEQUENCE: 81

Ser Ala Ser Thr Leu Ala Ser
1               5

<210> SEQ ID NO 82
<211> LENGTH: 7
<212> TYPE: PRT
<213> ORGANISM: Artificial Sequence
<220> FEATURE:
<223> OTHER INFORMATION: CFA0666 HVR-L2

<400> SEQUENCE: 82

Tyr Ala Ser Thr Leu Ala Ser

```
<210> SEQ ID NO 83
<211> LENGTH: 7
<212> TYPE: PRT
<213> ORGANISM: Artificial Sequence
<220> FEATURE:
<223> OTHER INFORMATION: CFA0672 HVR-L2

<400> SEQUENCE: 83

His Thr Ser Asp Leu Ala Ser
1               5

<210> SEQ ID NO 84
<211> LENGTH: 7
<212> TYPE: PRT
<213> ORGANISM: Artificial Sequence
<220> FEATURE:
<223> OTHER INFORMATION: CFA0675 HVR-L2

<400> SEQUENCE: 84

Tyr Ala Ser Thr Leu Ala Ser
1               5

<210> SEQ ID NO 85
<211> LENGTH: 7
<212> TYPE: PRT
<213> ORGANISM: Artificial Sequence
<220> FEATURE:
<223> OTHER INFORMATION: 305L05 HVR-L2

<400> SEQUENCE: 85

Gly Ala Ser Lys Thr His Ser
1               5

<210> SEQ ID NO 86
<211> LENGTH: 12
<212> TYPE: PRT
<213> ORGANISM: Artificial Sequence
<220> FEATURE:
<223> OTHER INFORMATION: CFA0305 HVR-L3

<400> SEQUENCE: 86

Gln Cys Thr Phe Val Gly Ser Ser Tyr Gly Asn Ala
1               5                   10

<210> SEQ ID NO 87
<211> LENGTH: 12
<212> TYPE: PRT
<213> ORGANISM: Artificial Sequence
<220> FEATURE:
<223> OTHER INFORMATION: CFA0307 HVR-L3

<400> SEQUENCE: 87

Leu Gln Gly Tyr Ser Tyr Ser Asn Val Asp Asp Ala
1               5                   10

<210> SEQ ID NO 88
<211> LENGTH: 12
<212> TYPE: PRT
<213> ORGANISM: Artificial Sequence
<220> FEATURE:
<223> OTHER INFORMATION: CFA0366 HVR-L3

<400> SEQUENCE: 88

Gln Gly Thr Tyr Tyr Ser Ser Gly Trp Tyr Phe Ala
1               5                   10
```

```
<210> SEQ ID NO 89
<211> LENGTH: 12
<212> TYPE: PRT
<213> ORGANISM: Artificial Sequence
<220> FEATURE:
<223> OTHER INFORMATION: CFA0501 HVR-L3

<400> SEQUENCE: 89

Gln Gln Asp Tyr Ser Ser Ser Asn Val Asp Asn Thr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: CFA0538 HVR-L3

<400> SEQUENCE: 90

Gln Gln Asp Tyr Ser Ser Ser Asn Val Asp Asn Thr
1               5                   10

<210> SEQ ID NO 91
<211> LENGTH: 12
<212> TYPE: PRT
<213> ORGANISM: Artificial Sequence
<220> FEATURE:
<223> OTHER INFORMATION: CFA0599 HVR-L3

<400> SEQUENCE: 91

Gln Gln Tyr Tyr Ser Ser Thr Asn Val His Asn Ser
1               5                   10

<210> SEQ ID NO 92
<211> LENGTH: 12
<212> TYPE: PRT
<213> ORGANISM: Artificial Sequence
<220> FEATURE:
<223> OTHER INFORMATION: CFA0666 HVR-L3

<400> SEQUENCE: 92

Gln Gln Tyr Tyr Asp Ile Asn Ser Val Asp Asn Thr
1               5                   10

<210> SEQ ID NO 93
<211> LENGTH: 13
<212> TYPE: PRT
<213> ORGANISM: Artificial Sequence
<220> FEATURE:
<223> OTHER INFORMATION: CFA0672 HVR-L3

<400> SEQUENCE: 93

Gln Cys Thr Ala Tyr Gly Ser Ser Asp Val Gly Gly Thr
1               5                   10

<210> SEQ ID NO 94
<211> LENGTH: 12
<212> TYPE: PRT
<213> ORGANISM: Artificial Sequence
<220> FEATURE:
<223> OTHER INFORMATION: CFA0675 HVR-L3

<400> SEQUENCE: 94

Gln Gln Tyr Tyr Asp Ile Asn Ser Val Asp Asn Thr
1               5                   10
```

<210> SEQ ID NO 95
<211> LENGTH: 12
<212> TYPE: PRT
<213> ORGANISM: Artificial Sequence
<220> FEATURE:
<223> OTHER INFORMATION: 305L05 HVR-L3

<400> SEQUENCE: 95

```
Gln Ser Thr Lys Val Gly Ser Ser Tyr Gly Asn His
1               5                   10
```

<210> SEQ ID NO 96
<211> LENGTH: 1680
<212> TYPE: PRT
<213> ORGANISM: Artificial Sequence
<220> FEATURE:
<223> OTHER INFORMATION: mouse C5

<400> SEQUENCE: 96

```
Met Gly Leu Trp Gly Ile Leu Cys Leu Leu Ile Phe Leu Asp Lys Thr
1               5                   10                  15

Trp Gly Gln Glu Gln Thr Tyr Val Ile Ser Ala Pro Lys Ile Leu Arg
                20                  25                  30

Val Gly Ser Ser Glu Asn Val Val Ile Gln Val His Gly Tyr Thr Glu
            35                  40                  45

Ala Phe Asp Ala Thr Leu Ser Leu Lys Ser Tyr Pro Asp Lys Lys Val
        50                  55                  60

Thr Phe Ser Ser Gly Tyr Val Asn Leu Ser Pro Glu Asn Lys Phe Gln
65                  70                  75                  80

Asn Ala Ala Leu Leu Thr Leu Gln Pro Asn Gln Val Pro Arg Glu Glu
                85                  90                  95

Ser Pro Val Ser His Val Tyr Leu Glu Val Val Ser Lys His Phe Ser
            100                 105                 110

Lys Ser Lys Lys Ile Pro Ile Thr Tyr Asn Asn Gly Ile Leu Phe Ile
        115                 120                 125

His Thr Asp Lys Pro Val Tyr Thr Pro Asp Gln Ser Val Lys Ile Arg
130                 135                 140

Val Tyr Ser Leu Gly Asp Asp Leu Lys Pro Ala Lys Arg Glu Thr Val
145                 150                 155                 160

Leu Thr Phe Ile Asp Pro Glu Gly Ser Glu Val Asp Ile Val Glu Glu
                165                 170                 175

Asn Asp Tyr Thr Gly Ile Ile Ser Phe Pro Asp Phe Lys Ile Pro Ser
            180                 185                 190

Asn Pro Lys Tyr Gly Val Trp Thr Ile Lys Ala Asn Tyr Lys Lys Asp
        195                 200                 205

Phe Thr Thr Thr Gly Thr Ala Tyr Phe Glu Ile Lys Glu Tyr Val Leu
    210                 215                 220

Pro Arg Phe Ser Val Ser Ile Glu Leu Glu Arg Thr Phe Ile Gly Tyr
225                 230                 235                 240

Lys Asn Phe Lys Asn Phe Glu Ile Thr Val Lys Ala Arg Tyr Phe Tyr
                245                 250                 255

Asn Lys Val Val Pro Asp Ala Glu Val Tyr Ala Phe Phe Gly Leu Arg
            260                 265                 270

Glu Asp Ile Lys Asp Glu Glu Lys Gln Met Met His Lys Ala Thr Gln
        275                 280                 285

Ala Ala Lys Leu Val Asp Gly Val Ala Gln Ile Ser Phe Asp Ser Glu
    290                 295                 300
```

```
Thr Ala Val Lys Glu Leu Ser Tyr Asn Ser Leu Glu Asp Leu Asn Asn
305                 310                 315                 320

Lys Tyr Leu Tyr Ile Ala Val Thr Val Thr Glu Ser Ser Gly Gly Phe
                325                 330                 335

Ser Glu Glu Ala Glu Ile Pro Gly Val Lys Tyr Val Leu Ser Pro Tyr
            340                 345                 350

Thr Leu Asn Leu Val Ala Thr Pro Leu Phe Val Lys Pro Gly Ile Pro
            355                 360                 365

Phe Ser Ile Lys Ala Gln Val Lys Asp Ser Leu Glu Gln Ala Val Gly
        370                 375                 380

Gly Val Pro Val Thr Leu Met Ala Gln Thr Val Asp Val Asn Gln Glu
385                 390                 395                 400

Thr Ser Asp Leu Glu Thr Lys Arg Ser Ile Thr His Asp Thr Asp Gly
                405                 410                 415

Val Ala Val Phe Val Leu Asn Leu Pro Ser Asn Val Thr Val Leu Lys
                420                 425                 430

Phe Glu Ile Arg Thr Asp Asp Pro Glu Leu Pro Glu Glu Asn Gln Ala
            435                 440                 445

Ser Lys Glu Tyr Glu Ala Val Ala Tyr Ser Ser Leu Ser Gln Ser Tyr
        450                 455                 460

Ile Tyr Ile Ala Trp Thr Glu Asn Tyr Lys Pro Met Leu Val Gly Glu
465                 470                 475                 480

Tyr Leu Asn Ile Met Val Thr Pro Lys Ser Pro Tyr Ile Asp Lys Ile
                485                 490                 495

Thr His Tyr Asn Tyr Leu Ile Leu Ser Lys Gly Lys Ile Val Gln Tyr
                500                 505                 510

Gly Thr Arg Glu Lys Leu Phe Ser Ser Thr Tyr Gln Asn Ile Asn Ile
            515                 520                 525

Pro Val Thr Gln Asn Met Val Pro Ser Ala Arg Leu Leu Val Tyr Tyr
        530                 535                 540

Ile Val Thr Gly Glu Gln Thr Ala Glu Leu Val Ala Asp Ala Val Trp
545                 550                 555                 560

Ile Asn Ile Glu Glu Lys Cys Gly Asn Gln Leu Gln Val His Leu Ser
                565                 570                 575

Pro Asp Glu Tyr Val Tyr Ser Pro Gly Gln Thr Val Ser Leu Asp Met
                580                 585                 590

Val Thr Glu Ala Asp Ser Trp Val Ala Leu Ser Ala Val Asp Arg Ala
            595                 600                 605

Val Tyr Lys Val Gln Gly Asn Ala Lys Arg Ala Met Gln Arg Val Phe
        610                 615                 620

Gln Ala Leu Asp Glu Lys Ser Asp Leu Gly Cys Gly Ala Gly Gly Gly
625                 630                 635                 640

His Asp Asn Ala Asp Val Phe His Leu Ala Gly Leu Thr Phe Leu Thr
                645                 650                 655

Asn Ala Asn Ala Asp Asp Ser His Tyr Arg Asp Asp Ser Cys Lys Glu
                660                 665                 670

Ile Leu Arg Ser Lys Arg Asn Leu His Leu Leu Arg Gln Lys Ile Glu
            675                 680                 685

Glu Gln Ala Ala Lys Tyr Lys His Ser Val Pro Lys Lys Cys Cys Tyr
        690                 695                 700

Asp Gly Ala Arg Val Asn Phe Tyr Glu Thr Cys Glu Glu Arg Val Ala
705                 710                 715                 720
```

-continued

Arg Val Thr Ile Gly Pro Leu Cys Ile Arg Ala Phe Asn Glu Cys Cys
            725                 730                 735

Thr Ile Ala Asn Lys Ile Arg Lys Glu Ser Pro His Lys Pro Val Gln
            740                 745                 750

Leu Gly Arg Ile His Ile Lys Thr Leu Leu Pro Val Met Lys Ala Asp
            755                 760                 765

Ile Arg Ser Tyr Phe Pro Glu Ser Trp Leu Trp Glu Ile His Arg Val
            770                 775                 780

Pro Lys Arg Lys Gln Leu Gln Val Thr Leu Pro Asp Ser Leu Thr Thr
785                 790                 795                 800

Trp Glu Ile Gln Gly Ile Gly Ile Ser Asp Asn Gly Ile Cys Val Ala
                    805                 810                 815

Asp Thr Leu Lys Ala Lys Val Phe Lys Glu Val Phe Leu Glu Met Asn
            820                 825                 830

Ile Pro Tyr Ser Val Val Arg Gly Glu Gln Ile Gln Leu Lys Gly Thr
            835                 840                 845

Val Tyr Asn Tyr Met Thr Ser Gly Thr Lys Phe Cys Val Lys Met Ser
850                 855                 860

Ala Val Glu Gly Ile Cys Thr Ser Gly Ser Ala Ala Ser Leu His
865                 870                 875                 880

Thr Ser Arg Pro Ser Arg Cys Val Phe Gln Arg Ile Glu Gly Ser Ser
            885                 890                 895

Ser His Leu Val Thr Phe Thr Leu Leu Pro Leu Glu Ile Gly Leu His
            900                 905                 910

Ser Ile Asn Phe Ser Leu Glu Thr Ser Phe Gly Lys Asp Ile Leu Val
            915                 920                 925

Lys Thr Leu Arg Val Val Pro Glu Gly Val Lys Arg Glu Ser Tyr Ala
930                 935                 940

Gly Val Ile Leu Asp Pro Lys Gly Ile Arg Gly Ile Val Asn Arg Arg
945                 950                 955                 960

Lys Glu Phe Pro Tyr Arg Ile Pro Leu Asp Leu Val Pro Lys Thr Lys
            965                 970                 975

Val Glu Arg Ile Leu Ser Val Lys Gly Leu Leu Val Gly Glu Phe Leu
            980                 985                 990

Ser Thr Val Leu Ser Lys Glu Gly Ile Asn Ile Leu Thr His Leu Pro
            995                 1000                1005

Lys Gly Ser Ala Glu Ala Glu Leu Met Ser Ile Ala Pro Val Phe
            1010                1015                1020

Tyr Val Phe His Tyr Leu Glu Ala Gly Asn His Trp Asn Ile Phe
            1025                1030                1035

Tyr Pro Asp Thr Leu Ser Lys Arg Gln Ser Leu Glu Lys Lys Ile
            1040                1045                1050

Lys Gln Gly Val Val Ser Val Met Ser Tyr Arg Asn Ala Asp Tyr
            1055                1060                1065

Ser Tyr Ser Met Trp Lys Gly Ala Ser Ala Ser Thr Trp Leu Thr
            1070                1075                1080

Ala Phe Ala Leu Arg Val Leu Gly Gln Val Ala Lys Tyr Val Lys
            1085                1090                1095

Gln Asp Glu Asn Ser Ile Cys Asn Ser Leu Leu Trp Leu Val Glu
            1100                1105                1110

Lys Cys Gln Leu Glu Asn Gly Ser Phe Lys Glu Asn Ser Gln Tyr
            1115                1120                1125

Leu Pro Ile Lys Leu Gln Gly Thr Leu Pro Ala Glu Ala Gln Glu

-continued

```
                1130                1135                1140
Lys Thr Leu Tyr Leu Thr Ala Phe Ser Val Ile Gly Ile Arg Lys
                1145                1150                1155
Ala Val Asp Ile Cys Pro Thr Met Lys Ile His Thr Ala Leu Asp
                1160                1165                1170
Lys Ala Asp Ser Phe Leu Leu Glu Asn Thr Leu Pro Ser Lys Ser
                1175                1180                1185
Thr Phe Thr Leu Ala Ile Val Ala Tyr Ala Leu Ser Leu Gly Asp
                1190                1195                1200
Arg Thr His Pro Arg Phe Arg Leu Ile Val Ser Ala Leu Arg Lys
                1205                1210                1215
Glu Ala Phe Val Lys Gly Asp Pro Pro Ile Tyr Arg Tyr Trp Arg
                1220                1225                1230
Asp Thr Leu Lys Arg Pro Asp Ser Ser Val Pro Ser Ser Gly Thr
                1235                1240                1245
Ala Gly Met Val Glu Thr Thr Ala Tyr Ala Leu Leu Ala Ser Leu
                1250                1255                1260
Lys Leu Lys Asp Met Asn Tyr Ala Asn Pro Ile Ile Lys Trp Leu
                1265                1270                1275
Ser Glu Glu Gln Arg Tyr Gly Gly Gly Phe Tyr Ser Thr Gln Asp
                1280                1285                1290
Thr Ile Asn Ala Ile Glu Gly Leu Thr Glu Tyr Ser Leu Leu Leu
                1295                1300                1305
Lys Gln Ile His Leu Asp Met Asp Ile Asn Val Ala Tyr Lys His
                1310                1315                1320
Glu Gly Asp Phe His Lys Tyr Lys Val Thr Glu Lys His Phe Leu
                1325                1330                1335
Gly Arg Pro Val Glu Val Ser Leu Asn Asp Asp Leu Val Val Ser
                1340                1345                1350
Thr Gly Tyr Ser Ser Gly Leu Ala Thr Val Tyr Val Lys Thr Val
                1355                1360                1365
Val His Lys Ile Ser Val Ser Glu Glu Phe Cys Ser Phe Tyr Leu
                1370                1375                1380
Lys Ile Asp Thr Gln Asp Ile Glu Ala Ser His Phe Arg Leu
                1385                1390                1395
Ser Asp Ser Gly Phe Lys Arg Ile Ile Ala Cys Ala Ser Tyr Lys
                1400                1405                1410
Pro Ser Lys Glu Glu Ser Thr Ser Gly Ser Ser His Ala Val Met
                1415                1420                1425
Asp Ile Ser Leu Pro Thr Gly Ile Gly Ala Asn Glu Glu Asp Leu
                1430                1435                1440
Arg Ala Leu Val Glu Gly Val Asp Gln Leu Leu Thr Asp Tyr Gln
                1445                1450                1455
Ile Lys Asp Gly His Val Ile Leu Gln Leu Asn Ser Ile Pro Ser
                1460                1465                1470
Arg Asp Phe Leu Cys Val Arg Phe Arg Ile Phe Glu Leu Phe Gln
                1475                1480                1485
Val Gly Phe Leu Asn Pro Ala Thr Phe Thr Val Tyr Glu Tyr His
                1490                1495                1500
Arg Pro Asp Lys Gln Cys Thr Met Ile Tyr Ser Ile Ser Asp Thr
                1505                1510                1515
Arg Leu Gln Lys Val Cys Glu Gly Ala Ala Cys Thr Cys Val Glu
                1520                1525                1530
```

Ala Asp Cys Ala Gln Leu Gln Ala Glu Val Asp Leu Ala Ile Ser
    1535                1540                1545

Ala Asp Ser Arg Lys Glu Lys Ala Cys Lys Pro Glu Thr Ala Tyr
    1550                1555                1560

Ala Tyr Lys Val Arg Ile Thr Ser Ala Thr Glu Glu Asn Val Phe
    1565                1570                1575

Val Lys Tyr Thr Ala Thr Leu Leu Val Thr Tyr Lys Thr Gly Glu
    1580                1585                1590

Ala Ala Asp Glu Asn Ser Glu Val Thr Phe Ile Lys Lys Met Ser
    1595                1600                1605

Cys Thr Asn Ala Asn Leu Val Lys Gly Lys Gln Tyr Leu Ile Met
    1610                1615                1620

Gly Lys Glu Val Leu Gln Ile Lys His Asn Phe Ser Phe Lys Tyr
    1625                1630                1635

Ile Tyr Pro Leu Asp Ser Ser Thr Trp Ile Glu Tyr Trp Pro Thr
    1640                1645                1650

Asp Thr Thr Cys Pro Ser Cys Gln Ala Phe Val Glu Asn Leu Asn
    1655                1660                1665

Asn Phe Ala Glu Asp Leu Phe Leu Asn Ser Cys Glu
    1670                1675                1680

<210> SEQ ID NO 97
<211> LENGTH: 123
<212> TYPE: PRT
<213> ORGANISM: Artificial Sequence
<220> FEATURE:
<223> OTHER INFORMATION: 305LO15 VH

<400> SEQUENCE: 97

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
        115                 120

<210> SEQ ID NO 98
<211> LENGTH: 123
<212> TYPE: PRT
<213> ORGANISM: Artificial Sequence
<220> FEATURE:
<223> OTHER INFORMATION: 305LO16 VH

<400> SEQUENCE: 98

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser

```
                    20                  25                  30
Tyr Tyr Met Ala Trp Val Arg Gln Ala Pro Gly Lys Gly Leu Glu Trp
            35                  40                  45

Val Gly Ala Ile Phe Thr Gly Ser Gly Ala Glu Tyr Lys Ala Glu Trp
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Asp Ala Gly Tyr Asp Tyr Pro Thr His Ala Met His Tyr
            100                 105                 110

Trp Gly Arg Gly Thr Leu Val Thr Val Ser Ser
        115                 120

<210> SEQ ID NO 99
<211> LENGTH: 123
<212> TYPE: PRT
<213> ORGANISM: Artificial Sequence
<220> FEATURE:
<223> OTHER INFORMATION: 305L018 VH

<400> SEQUENCE: 99

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Arg Gly Thr Leu Val Thr Val Ser Ser
        115                 120

<210> SEQ ID NO 100
<211> LENGTH: 123
<212> TYPE: PRT
<213> ORGANISM: Artificial Sequence
<220> FEATURE:
<223> OTHER INFORMATION: 305L019, 20, 22 VH

<400> SEQUENCE: 100

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80
```

```
Val Leu Thr Met Thr Asn Met Asp Pro Val Asp Ala Thr Tyr Tyr
                 85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
        115                 120
```

<210> SEQ ID NO 101
<211> LENGTH: 123
<212> TYPE: PRT
<213> ORGANISM: Artificial Sequence
<220> FEATURE:
<223> OTHER INFORMATION: 305LO23 VH

<400> SEQUENCE: 101

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Ser Gly Ile Phe Thr Gly Ser Gly Ala Thr Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Ala Thr Tyr Tyr
                 85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
        115                 120
```

<210> SEQ ID NO 102
<211> LENGTH: 110
<212> TYPE: PRT
<213> ORGANISM: Artificial Sequence
<220> FEATURE:
<223> OTHER INFORMATION: 305LO15, 16, 18, 19 VL

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110
```

<210> SEQ ID NO 103
<211> LENGTH: 110
<212> TYPE: PRT
<213> ORGANISM: Artificial Sequence

```
<220> FEATURE:
<223> OTHER INFORMATION: 305LO20 VL

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110

<210> SEQ ID NO 104
<211> LENGTH: 110
<212> TYPE: PRT
<213> ORGANISM: Artificial Sequence
<220> FEATURE:
<223> OTHER INFORMATION: 305LO22, 23 VL

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Thr Thr Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110

<210> SEQ ID NO 105
<211> LENGTH: 328
<212> TYPE: PRT
<213> ORGANISM: Artificial Sequence
<220> FEATURE:
<223> OTHER INFORMATION: SG115

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Arg Arg Gly Pro Lys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ala His Tyr Thr
305                 310                 315                 320

Arg Lys Glu Leu Ser Leu Ser Pro
                325

<210> SEQ ID NO 106
<211> LENGTH: 325
<212> TYPE: PRT
<213> ORGANISM: Artificial Sequence
<220> FEATURE:
<223> OTHER INFORMATION: SG422

<400> SEQUENCE: 106

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95
```

Arg Val Glu Ser Lys Tyr Gly Pro Pro Cys Pro Cys Pro Ala Pro
            100                 105                 110

Glu Phe Arg Arg Gly Pro Lys Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Leu His Glu Ala Leu His Ala His Tyr Thr Arg Lys Glu
305                 310                 315                 320

Leu Ser Leu Ser Pro
                325

<210> SEQ ID NO 107
<211> LENGTH: 325
<212> TYPE: PRT
<213> ORGANISM: Artificial Sequence
<220> FEATURE:
<223> OTHER INFORMATION: SG429

<400> SEQUENCE: 107

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Arg Gly Pro Lys Val Phe Leu Phe Pro Pro Lys Pro Lys
            115                 120                 125

```
Asp Thr Leu Met Ile Ser Arg Thr Pro Glu Val Thr Cys Val Val Val
    130                 135                 140
Asp Val Ser His Glu Asp Pro Glu Val Lys Phe Asn Trp Tyr Val Asp
145                 150                 155                 160
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Arg Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Gln Gly Asn Val Phe Ser
290                 295                 300
Cys Ser Val Leu His Glu Ala Leu His Ala His Tyr Thr Arg Lys Glu
305                 310                 315                 320
Leu Ser Leu Ser Pro
                325

<210> SEQ ID NO 108
<211> LENGTH: 6
<212> TYPE: PRT
<213> ORGANISM: Artificial Sequence
<220> FEATURE:
<223> OTHER INFORMATION: 305L015, 16, 18, 19, 20, 22, 23 HVR-H1

<400> SEQUENCE: 108

Ser Ser Tyr Tyr Met Ala
1               5

<210> SEQ ID NO 109
<211> LENGTH: 17
<212> TYPE: PRT
<213> ORGANISM: Artificial Sequence
<220> FEATURE:
<223> OTHER INFORMATION: 305L015, 18, 19, 20, 22 HVR-H2

<400> SEQUENCE: 109

Ala Ile Phe Thr Gly Ser Gly Ala Glu Tyr Lys Ala Glu Trp Ala Lys
1               5                   10                  15
Gly

<210> SEQ ID NO 110
<211> LENGTH: 17
<212> TYPE: PRT
<213> ORGANISM: Artificial Sequence
<220> FEATURE:
<223> OTHER INFORMATION: 305L016 HVR-H2

<400> SEQUENCE: 110

Ala Ile Phe Thr Gly Ser Gly Ala Glu Tyr Lys Ala Glu Trp Val Lys
1               5                   10                  15
```

Gly

<210> SEQ ID NO 111
<211> LENGTH: 17
<212> TYPE: PRT
<213> ORGANISM: Artificial Sequence
<220> FEATURE:
<223> OTHER INFORMATION: 305LO23 HVR-H2

<400> SEQUENCE: 111

Gly Ile Phe Thr Gly Ser Gly Ala Thr Tyr Lys Ala Glu Trp Ala Lys
1               5                   10                  15

Gly

<210> SEQ ID NO 112
<211> LENGTH: 13
<212> TYPE: PRT
<213> ORGANISM: Artificial Sequence
<220> FEATURE:
<223> OTHER INFORMATION: 305LO15, 16, 18, 19, 20, 22, 23 HVR-H3

<400> SEQUENCE: 112

Asp Ala Gly Tyr Asp Tyr Pro Thr His Ala Met His Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: 305LO15, 16, 18, 19, 20, 22, 23 HVR-L1

<400> SEQUENCE: 113

Arg Ala Ser Gln Gly Ile Ser Ser Ser Leu Ala
1               5                   10

<210> SEQ ID NO 114
<211> LENGTH: 7
<212> TYPE: PRT
<213> ORGANISM: Artificial Sequence
<220> FEATURE:
<223> OTHER INFORMATION: 305LO15, 16, 18, 19, 20 HVR-L2

<400> SEQUENCE: 114

Gly Ala Ser Glu Thr Glu Ser
1               5

<210> SEQ ID NO 115
<211> LENGTH: 7
<212> TYPE: PRT
<213> ORGANISM: Artificial Sequence
<220> FEATURE:
<223> OTHER INFORMATION: 305LO22, 23 HVR-L2

<400> SEQUENCE: 115

Gly Ala Ser Thr Thr Gln Ser
1               5

<210> SEQ ID NO 116
<211> LENGTH: 12
<212> TYPE: PRT

```
<213> ORGANISM: Artificial Sequence
<220> FEATURE:
<223> OTHER INFORMATION: 305LO15, 16, 18, 19, 20, 22, 23 HVR-L3

<400> SEQUENCE: 116

Gln Asn Thr Lys Val Gly Ser Ser Tyr Gly Asn Thr
1               5                   10
```